(12) United States Patent
Dennis et al.

(10) Patent No.: US 7,084,109 B2
(45) Date of Patent: Aug. 1, 2006

(54) FVIIA ANTAGONISTS

(75) Inventors: Mark S. Dennis, San Carlos, CA (US); Charles Eigenbrot, South San Francisco, CA (US); Robert A. Lazarus, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 264 days.

(21) Appl. No.: 10/202,915

(22) Filed: Jul. 25, 2002

(65) Prior Publication Data

US 2003/0119727 A1 Jun. 26, 2003

Related U.S. Application Data

(63) Continuation of application No. 09/609,574, filed on Jun. 30, 2000, now abandoned.
(60) Provisional application No. 60/142,211, filed on Jul. 2, 1999.

(51) Int. Cl.
*A61K 38/00* (2006.01)
*C07K 14/00* (2006.01)

(52) U.S. Cl. .................. 514/2; 514/824; 435/7.1; 530/300; 530/326; 530/325; 530/324

(58) Field of Classification Search .............. 530/300, 530/326, 325, 324; 435/7.1; 514/2, 824
See application file for complete search history.

(56) References Cited

U.S. PATENT DOCUMENTS

| | | | |
|---|---|---|---|
| 5,116,964 A | 5/1992 | Capon et al. | 536/27 |
| 5,336,603 A | 8/1994 | Capon et al. | 435/69.7 |
| 5,714,147 A | 2/1998 | Capon et al. | 424/178.1 |
| 5,759,954 A | 6/1998 | Taguchi et al. | 503/227 |
| 5,834,244 A | 11/1998 | Dennis et al. | 435/69.2 |
| 5,863,893 A | 1/1999 | Dennis et al. | 514/12 |
| 5,880,256 A | 3/1999 | Dennis et al. | 530/324 |

FOREIGN PATENT DOCUMENTS

| | | |
|---|---|---|
| WO | WO 90/03390 | 4/1990 |
| WO | WO 91/11514 | 8/1991 |
| WO | WO 95/00541 | 1/1995 |
| WO | WO 96/40779 | 12/1996 |
| WO | WO 97/20939 | 6/1997 |
| WO | WO 00/24782 | 5/2000 |

OTHER PUBLICATIONS

Adams et al., "The genome sequence of *Drosophila melanogaster*" *Science* (abstract only) 287(5461):2185–2195 (2000).
Badimon et al., "Hirudin and Other Thrombin Inhibitors: Experimental Results and Potential Clinical Applications" *Trends Cardiovasc. Med.* 1(6):261–267 (1991).
Banner et al., "The crystal structure of the complex of blood coagulation factor VIIa with soluble tissue factor" *Nature* 380:41–46 (1996).
Bone, R. C., "Modulators of Coagulation: A Critical Appraisal of Their Role In Sepsis" *Arch Intern Med* 152:1381–1389 (1992).
Carson and Brozna, "The role of tissue factor in the production of thrombin" *Blood. Coag. Fibrinol* 4:281–292 (1993).
Clackson and Wells, "In vitro selection from protein and peptide libraries" *Trends Biotechnol.* 12:173–184 (1994).
Colman, R. W., "The Role of Plasma Proteases In Septic Shock" *The New England J. of Med.* 320(18):1207–1209 (1989).
Creasey et al., "Tissue Factor Pathway Inhibitor Reduces Mortality from *Escherichia coli* Septic Shock" *J. Clin. Invest.* 91:2850–2860 (1993).
Davie et al., "The Coagulation Cascade: Initiation, Maitenance, and Regulation" *Biochemistry* 30(43):10363–10370 (1991).
Dennis et al., "Peptide exosite inhibitors of factor VIIa as anticoagulants" *Nature* 404:465–470 (2000).
Dickinson et al., "Influence of Cofactor Binding and Active Site Occupancy on the Conformation of the Macromolecular Substrate Exosite of Factor VIIa" *J. Mol. Biol.* 277:959–971 (1998).
Hagen et al., "Characterization of a cDNA coding for human factor VII" *Proc. Natl. Acad. Sci. USA* 83:2412–2416 (1986).
Harlos et al., "Crystal structure of the extracellular region of human tissue factor" *Nature* 370:662–666 (1994).
Haskel et al., "Prevention of Arterial Reocclusion After Thrombolysis With Recombinant Lipoprotein–Associated Coagulation Inhibitor" *Circulation* 84(2):821–827 (1991).
Higashi et al., "Identification of Regions of Bovine Factor VII Essential for Binding Tissue Factor" *Journal of Biological Chemistry* 269:18891–18898 (1994).
Holst et al., "Antithrombotic Properties of a Truncated Recombinant Tissue Factor Pathway Inhibitor in an Experimental Venous Thrombosis Model" *Haemostasis* 23(Suppl. 1):112–117 (1993).

(Continued)

*Primary Examiner*—Jon Weber
*Assistant Examiner*—Holly Schnizer
(74) *Attorney, Agent, or Firm*—Merchant & Gould P.C.

(57) ABSTRACT

This invention provides novel compounds which prevent or block a FVIIa mediated or associated process or event such as the catalytic conversion of FX to FXa, FVII to FVIIa or FIX to FIXa. In particular aspects, the compounds of the invention bind Factor VIIa (FVIIa), its zymogen Factor VII (FVII) and/or block the association of FVII or FVIIa with a peptide compound of the present invention. The invention also provides pharmaceutical compositions comprising the novel compounds as well as their use in diagnostic, therapeutic, and prophylactic methods.

63 Claims, 12 Drawing Sheets

OTHER PUBLICATIONS

Husbyn et al., "Peptides corresponding to the second epidermal growth factor–like domain of human blood coagulation factor VII: synthesis, folding and biological activity" *J. Peptide Res.* 50:475–482 (1997).

Kelly et al., "Ca$^{2+}$Binding to the First Epidermal Growth Factor Module Coagulation Factor VIIa Is Important for Cofactor Interaction and Proteolytic Function" *Journal of Biological Chemistry* 272:17467–17472 (1997).

Lee et al., "Potent Bifunctional Anticoagulants: Kunitz Domain–Tissue Factor Fusion Proteins" *Biochemistry* 36(19):5607–5611 (1997).

Lowman et al., "Molecular Mimics of Insulin–Like Growth Factor 1 (IGF–1) for Inhibiting IGF–1: IGF–Binding protein Interactions." *Biochemistry* 37(25):8870–8878 (1998).

Lowman, H., "Bacteriophage display and discovery of peptide leads for drug development" *Annual Review of Biophysics and Biomolecular Structure* 26:401–424 (1997).

Mori et al., "Analysis of promoter activity of 5'–upstream regions of zebrafish olfactory receptor genes" *Biol. Pharm. Bull.* (abstract only) 23(2):165–173 (2000).

Muller et al., "Structure of the Extracellular Domain of Human Tissue Factor: Location of the Factor VIIa Binding Site" *Biochemistry* 33(36):10864–10870 (1994).

O'Brien et al., "Factor VIII–Bypassing Activity of Bovine Tissue Factor Using the Canine Hemophilic Model" *J. Clin. Invest.* 82:206–211 (1988).

Paborsky et al., "Lipid Association, but Not the Transmembrane Domain, Is Required for Tissue Factor Activity" *Journal of Biological Chemistry* 266:21911–21916 (1991).

Rapaport and Rao, "Initiation and Regulation of Tissue Factor–Dependent Blood Coagulation" *Arterioscler. Thromb.* 12(10):1111–1121 (1992).

Roy et al., "Self–association of Tissue Factor as Revealed by Chemical Cross–linking" *Journal of Biological Chemistry* 266(8):4665–4668 (1991).

Rudinger, J., "Characteristics of the Amino Acids as Components of a Peptide Hormone Sequence" *Peptide Hormones*, J.A. Parsons, Baltimore:University Park Press pp. 1–7 (1976).

Sawyer, T.K., "Peptidomimetic Design and Chemical Approaches to Peptide Metabolism" *Peptide–Based Drug Design: Controlling Transport and Metabolism*, Taylor and Amidon, Washington, DC:American Chemical Society pps. 387–422 (1995).

Scott and Smith, "Searching for peptide ligands with an epitope library" *Science* 249:386–390 (1990).

Smith, G. P., "Surface presentation of protein epitopes using bacteriophage expression systems" *Curr. Opin. Biotechnol.* 2(5):668–673 (1991).

Wells and Lowman, "Rapid evolution of peptide and protein binding properties in vitro" *Curr. Opin. Biotechnol.* 3:355–362 (1992).

Wildgoose et al., "Identification of a Calcium Binding Site in the Protease Domain of Human Blood Coagulation Factor VII: Evidence for Its Role in Factor VII–Tissue Factor Interaction" *Biochemistry* 32:114–119 (1993).

Dennis et al., 1994, *The Journal of Biological Chemistry*, 269(2) Issue of Sep. 2:22129–22136 "Kunitz Domain Inhibitors of Tissue Factor–Factor VIIa.".

Lowman, *Methods in Molecular Biology*, 87:249–264 "Phage Display of Peptide Libraries on Protein Scaffolds.".

Sidhu et al., 2000, *Methods in Enzymology*, 328:333–363 "[21] Phage Display for Selection of Novel Binding Peptides.".

Singson et al., 1998, *Cell*, 93:71–79 "The C. elegans spe–9 Gene Encodes a Sperm Transmembrane Protein that contains EGF–like Repeats and Is Required for Fertilization.".

Lane

1 = Control Fc (no peptide fusion)

3 = TF151-Fc fusion

| Peptide Name | FX Activation IC50 (nM) | FVIIa Binding ELISA IC50 (nM) | TF-FVIIa Binding ELISA IC50 (nM) | Sequence |
|---|---|---|---|---|
| TF56 | 11867 | 2298 | | EAALCDDPRLDRWYCFAGE-amide |
| TF58 | 260 | 250000 | | EGTLCDDPRIDRWYCWFSGV-acid |
| TF61 | 80000 | 100000 | | LCDDPRIDRWYCWF-acid |
| TF62 | 15500 | 100000 | | LCDDPRVDRWYCF-acid |
| TF63 | 18000 | 100000 | | LCDDPRIDRWYCF-acid |
| TF74 | 0.7 | 5 | 12 | VGALCDDPRVDRWYCQFVE-amide |
| TF75 | 3.2 | 6 | 14 | VGALCDDPRVDRWYCQFVE-amide |
| TF76 | 1.0 | 21 | 28 | Ac-LCDDPRVDRWYCQFVE-amide |
| TF77 | 32 | 248 | 478 | Ac-LCDDPRVDRWYCQFVEG-amide |
| TF83 | 500 | 1760 | | Suc-LCDDPRVDRWYCQF-amide |
| TF84 | 0.42 | | | Biotin-aoaALCDDPRVDRWYCQFVEG-amide |
| TF86 | 1.4 | | | Suc-ALCDDPRVDRWYCQFVE-amide |
| TF87 | 2.7 | 6 | 14 | Ac-ALCDDPRVDRWYCQFVE-amide |
| TF88 | 34 | 19 | 77 | ALCDDPRVDRWYCQFVE-amide |
| TF89 | 5.1 | 76 | 675 | Ac-ALCDDPRVDRWYCQFVEG-amide |
| TF90 | 37 | 298 | 385 | Ac-ALCDDPRVDRWYCQFV-amide |
| TF92 | 2000 | 168 | | Ac-ALCDDPRVDRWYCEXYFG-amide |
| TF95 | 37 | 123 | 186 | Ac-ALCDDPEVDRWYCQFVEG-amide |
| TF96 | 161 | 257 | 531 | Ac-ALCDDPRVNRWYCQFVEG-amide |
| TF97 | 3024 | 1204 | 3102 | Ac-ALCDDPRVDQWYCQFVEG-amide |
| TF98 | 330 | 2563 | 548 | Ac-ALCDDPRVDRWYCQFVEG-amide |
| TF106 | 0.49 | 2 | 8 | Ac-ALCDNPRVDRWYCQFVEG-amide |
| TF107 | 6.3 | 10 | 28 | Ac-ALCADPRVDRWYCQFVEG-amide |
| TF108 | 58 | 104 | 186 | Ac-ALCDDAPRVDRWYCQFVEG-amide |
| TF109 | 65 | 110 | 287 | Ac-ALCDDPAVDRWYCQFVEG-amide |
| TF110 | 225 | 330 | 410 | Ac-ALCDDPRVARWYCQFVEG-amide |
| TF111 | 81 | 147 | 488 | Ac-ALCDDPRVERWYCQFVEG-amide |
| TF112 | 157 | 396 | 477 | Ac-ALCDDPRVDAWYCQFVEG-amide |
| TF113 | 2870 | 10489 | 10267 | Ac-ALCDDPRVDRAYCQFVEG-amide |
| TF114 | 84800 | >50000 | >100000 | Ac-ALCDDPRVDRWACQFVEG-amide |
| TF115 | 20700 | 20000 | 100000 | Ac-ALCDDPRVDRWYAQFVEG-amide |
| TF119 | 5380 | >100000 | 48707 | Ac-ALADDPRVDRWYCQFVEG-amide |
| TF120 | 127 | 109 | 464 | Ac-ALCDEPRVDRWYCQFVEG-amide |
| TF121 | 0.13 | 3 | 7 | Ac-ALCRDPRVDRWYCQFVEG-amide |
| TF127 | 8.3 | 28 | 88 | Ac-ALCDDPRLDRWYCQFVEG-amide |
| TF128 | 38 | 141 | 454 | Ac-ALCDDPRADRWYCQFVEG-amide |
| TF129 | 830 | 716 | 2078 | Ac-ALCDDPRVDKWYCQFVEG-amide |
| TF130 | 38 | 93 | 177 | Ac-ALCDDPRVDRWFCQFVEG-amide |

FIG. 8A

| Peptide Name | FX Activation IC50 (nM) | FVIIa Binding ELISA IC50 (nM) | TF-FVIIa Binding ELISA IC50 (nM) | Sequence |
|---|---|---|---|---|
| TF131 | 1050 | 4955 | 4217 | Ac-ALCDDPRVDRFYCQFVEG-amide |
| TF132 | 19 | 85 | 220 | Ac-ALCDDPRVDRWYCYFVEG-amide |
| TF144 | 314 | 485 | 1332 | Ac-ALCDDPRVDRWFCQFVEG-amide |
| TF145 | 95000 | >50000 | >100000 | Ac-ALCDDPRVDRWACQFVEG-amide |
| TF146 | 282 | 698 | 1477 | Ac-ALCDDPRVDRWYCQYVEG-amide |
| TF147b | 6.4 | | | Ac-ALCDDPRVDRWYCQFVEGSK*acB-amide |
| TF148 | >400000 | | | Ac-ALCDDPRVDRXYCQKVEX-amide |
| TF149 | 1200 | | 6250 | Ac-ALCDDPRVDXWYCQFVX-amide |
| TF150 | | | | Ac-ALCDDPRVDRWYCQFVEGSK-amide |
| TF151 | 0.65 | 2 | 6 | Ac-ALCDDNPFIDRWYCQFVEG-amide |
| TF152 | >40000 | >100000 | >100000 | Ac-ALCDDPRVDRHYCQFVEG-amide |
| TF155 | 4000 | 9778 | | Ac-AACDDPRVDRWYCQFVEG-amide |
| TF156 | 12000 | 90336 | | Ac-CDDPRVDRWYCQFVEG-amide |
| TF160 | 140000 | >1000000 | | Ac-ALCDDPRVQRWYCQFVEG-amide |
| TF161 | 6117 | 8622 | | Ac-ALCDDPRVSRWYCQFVEG-amide |
| TF182 | 434 | 359 | | Ac-ALCDDPRVDRNaYCQFVEG-amide |
| TF183 | 43 | 20 | | Ac-ALCDDPRVDARVCQFVEG-amide |
| TF178 | 21 | 20 | | Ac-ALCDDPRVDRWYCQFVEG-amide |
| TF179 | 32 | 32 | | Ac-ALCDDPRVDRWYCAFVEG-amide |
| TF180 | | 100000 | | Ac-ALCDDPRVDRWYC-amide |
| TF189 | | 438 | | Ac-ALCDDPRVDRWYCQLVEG-amide |
| TF190 | | 263 | | Ac-ALCDDPRVDRWYCOnLVEG-amide |
| TF191 | | 20346 | | Ac-ALCDDPRVDRWYCQQVEG-amide |
| TF192 | 0.9 | 7 | | Ac-ALCDDPRVDRWYCOmYVEG-amide |
| TF304 | | 2315 | | Ac-ALCDDPRVgaRWYCQFVEG-amide |
| TF305 | 1500 | 1798 | | Ac-ALCDDPRVDRWmYCQFVEG-amide |
| TF306 | | >100000 | | Ac-ALCDDPRVgaRWmYCQFVEG-amide |
| TF307 | | >100000 | | Ac-ALCDDPRVDRWgaCQFVEG-amide |
| TF312 | | 8889 | | Ac-ALCDDPRVXCCQFVEG-amide |
| TF313 | | >100000 | | Ac-ALCDDPRVXCQFVEG-amide |
| TF315 | 370 | 535 | | Ac-ALCDDPRVDXWYCQXFVEG-amide |
| TF316 | | 31500 | | Ac-ALCDDPRVDRWXCQFVEG-amide |
| TF317 | | 988 | | Ac-AVCDDPRVDRWXCQFVEG-amide |
| TF318 | | 75000 | | Ac-ATCDDPRVDRWXCQFVEG-amide |
| TF319 | | 24000 | | Ac-AMCDDPRVDRWXCQFVEG-amide |
| TF320 | | 42000 | | Ac-AKCDDPRVDRWXCQFVEG-amide |
| TF321 | | 3685 | | Ac-ALCDDPRVDXWYCXFVEG-amide |

SEQUENCE LISTING

<160> NUMBER OF SEQ ID NOS: 119

<210> SEQ ID NO 1
<211> LENGTH: 20
<212> TYPE: PRT
<213> ORGANISM: Artificial
<220> FEATURE:
<223> OTHER INFORMATION: Synthetic peptide sequence

<400> SEQUENCE: 1

Glu Ala Ala Leu Cys Asp Asp Pro Arg Leu Asp Arg Trp Tyr Cys Ile
1               5                   10                  15

Phe Ala Gly Glu
            20

<210> SEQ ID NO 2
<211> LENGTH: 20
<212> TYPE: PRT
<213> ORGANISM: Artificial
<220> FEATURE:
<223> OTHER INFORMATION: Synthetic peptide sequence

<400> SEQUENCE: 2

Glu Gly Thr Leu Cys Asp Asp Pro Arg Ile Asp Arg Trp Tyr Cys Met
1               5                   10                  15

Phe Ser Gly Val
            20

<210> SEQ ID NO 3
<211> LENGTH: 14
<212> TYPE: PRT
<213> ORGANISM: Artificial
<220> FEATURE:
<223> OTHER INFORMATION: Synthetic peptide sequence

<400> SEQUENCE: 3

Leu Cys Asp Asp Pro Arg Ile Asp Arg Trp Tyr Cys Met Phe
1               5                   10

<210> SEQ ID NO 4
<211> LENGTH: 14

-continued

```
<212> TYPE: PRT
<213> ORGANISM: Artificial
<220> FEATURE:
<223> OTHER INFORMATION: Synthetic peptide sequence

<400> SEQUENCE: 4

Leu Cys Asp Asp Pro Arg Val Asp Arg Trp Tyr Cys Gln Phe
1               5                   10

<210> SEQ ID NO 5
<211> LENGTH: 14
<212> TYPE: PRT
<213> ORGANISM: Artificial
<220> FEATURE:
<223> OTHER INFORMATION: Synthetic peptide sequence

<400> SEQUENCE: 5

Leu Cys Asp Asp Pro Arg Ile Asp Arg Trp Tyr Cys Gln Phe
1               5                   10

<210> SEQ ID NO 6
<211> LENGTH: 20
<212> TYPE: PRT
<213> ORGANISM: Artificial
<220> FEATURE:
<223> OTHER INFORMATION: Synthetic peptide sequence

<400> SEQUENCE: 6

Val Gly Ala Leu Cys Asp Asp Pro Arg Val Asp Arg Trp Tyr Cys Gln
1               5                   10                  15

Phe Val Glu Gly
            20

<210> SEQ ID NO 7
<211> LENGTH: 19
<212> TYPE: PRT
<213> ORGANISM: Artificial
<220> FEATURE:
<223> OTHER INFORMATION: Synthetic peptide sequence

<400> SEQUENCE: 7

Val Gly Ala Leu Cys Asp Asp Pro Arg Val Asp Arg Trp Tyr Cys Gln
1               5                   10                  15

Phe Val Glu

<210> SEQ ID NO 8
<211> LENGTH: 18
<212> TYPE: PRT
<213> ORGANISM: Artificial
<220> FEATURE:
<223> OTHER INFORMATION: Synthetic peptide sequence

<400> SEQUENCE: 8

Ala Leu Cys Asp Asp Pro Arg Val Asp Arg Trp Tyr Cys Gln Phe Val
1               5                   10                  15

Glu Gly

<210> SEQ ID NO 9
<211> LENGTH: 17
<212> TYPE: PRT
<213> ORGANISM: Artificial
<220> FEATURE:
<223> OTHER INFORMATION: Synthetic peptide sequence

<400> SEQUENCE: 9
```

```
Leu Cys Asp Asp Pro Arg Val Asp Arg Trp Tyr Cys Gln Phe Val Glu
1               5                   10                  15

Gly

<210> SEQ ID NO 10
<211> LENGTH: 17
<212> TYPE: PRT
<213> ORGANISM: Artificial
<220> FEATURE:
<223> OTHER INFORMATION: Synthetic peptide sequence

<400> SEQUENCE: 10

Ala Leu Cys Asp Asp Pro Arg Val Asp Arg Trp Tyr Cys Gln Phe Val
1               5                   10                  15

Glu

<210> SEQ ID NO 11
<211> LENGTH: 16
<212> TYPE: PRT
<213> ORGANISM: Artificial
<220> FEATURE:
<223> OTHER INFORMATION: Synthetic peptide sequence

<400> SEQUENCE: 11

Ala Leu Cys Asp Asp Pro Arg Val Asp Arg Trp Tyr Cys Gln Phe Val
1               5                   10                  15

<210> SEQ ID NO 12
<211> LENGTH: 15
<212> TYPE: PRT
<213> ORGANISM: Artificial
<220> FEATURE:
<223> OTHER INFORMATION: Synthetic peptide sequence

<400> SEQUENCE: 12

Ala Leu Cys Asp Asp Pro Arg Val Asp Arg Trp Tyr Cys Gln Phe
1               5                   10                  15

<210> SEQ ID NO 13
<211> LENGTH: 18
<212> TYPE: PRT
<213> ORGANISM: Artificial
<220> FEATURE:
<223> OTHER INFORMATION: Synthetic peptide sequence

<400> SEQUENCE: 13

Ala Leu Cys Asp Asp Pro Arg Val Asp Arg Trp Tyr Cys Glu Lys Tyr
1               5                   10                  15

Phe Gly

<210> SEQ ID NO 14
<211> LENGTH: 18
<212> TYPE: PRT
<213> ORGANISM: Artificial
<220> FEATURE:
<223> OTHER INFORMATION: Synthetic peptide sequence

<400> SEQUENCE: 14

Ala Leu Cys Asp Arg Pro Arg Val Asp Arg Trp Tyr Cys Gln Phe Val
1               5                   10                  15

Glu Gly

<210> SEQ ID NO 15
<211> LENGTH: 18
```

```
<212> TYPE: PRT
<213> ORGANISM: Artificial
<220> FEATURE:
<223> OTHER INFORMATION: Synthetic peptide sequence

<400> SEQUENCE: 15

Ala Leu Cys Asp Asp Pro Glu Val Asp Arg Trp Tyr Cys Gln Phe Val
1               5                   10                  15
Glu Gly

<210> SEQ ID NO 16
<211> LENGTH: 18
<212> TYPE: PRT
<213> ORGANISM: Artificial
<220> FEATURE:
<223> OTHER INFORMATION: Synthetic peptide sequence

<400> SEQUENCE: 16

Ala Leu Cys Asp Asp Pro Arg Val Asn Arg Trp Tyr Cys Gln Phe Val
1               5                   10                  15
Glu Gly

<210> SEQ ID NO 17
<211> LENGTH: 18
<212> TYPE: PRT
<213> ORGANISM: Artificial
<220> FEATURE:
<223> OTHER INFORMATION: Synthetic peptide sequence

<400> SEQUENCE: 17

Ala Leu Cys Asp Asp Pro Arg Val Asp Gln Trp Tyr Cys Gln Phe Val
1               5                   10                  15
Glu Gly

<210> SEQ ID NO 18
<211> LENGTH: 18
<212> TYPE: PRT
<213> ORGANISM: Artificial
<220> FEATURE:
<223> OTHER INFORMATION: Synthetic peptide sequence

<400> SEQUENCE: 18

Ala Leu Cys Asp Asn Pro Arg Val Asp Arg Trp Tyr Cys Gln Phe Val
1               5                   10                  15
Glu Gly

<210> SEQ ID NO 19
<211> LENGTH: 18
<212> TYPE: PRT
<213> ORGANISM: Artificial
<220> FEATURE:
<223> OTHER INFORMATION: Synthetic peptide sequence

<400> SEQUENCE: 19

Ala Leu Cys Ala Asp Pro Arg Val Asp Arg Trp Tyr Cys Gln Phe Val
1               5                   10                  15
Glu Gly

<210> SEQ ID NO 20
<211> LENGTH: 18
<212> TYPE: PRT
<213> ORGANISM: Artificial
<220> FEATURE:
<223> OTHER INFORMATION: Synthetic peptide sequence
```

```
<400> SEQUENCE: 20

Ala Leu Cys Asp Ala Pro Arg Val Asp Arg Trp Tyr Cys Gln Phe Val
1               5                   10                  15

Glu Gly

<210> SEQ ID NO 21
<211> LENGTH: 18
<212> TYPE: PRT
<213> ORGANISM: Artificial
<220> FEATURE:
<223> OTHER INFORMATION: Synthetic peptide sequence

<400> SEQUENCE: 21

Ala Leu Cys Asp Asp Pro Ala Val Asp Arg Trp Tyr Cys Gln Phe Val
1               5                   10                  15

Glu Gly

<210> SEQ ID NO 22
<211> LENGTH: 18
<212> TYPE: PRT
<213> ORGANISM: Artificial
<220> FEATURE:
<223> OTHER INFORMATION: Synthetic peptide sequence

<400> SEQUENCE: 22

Ala Leu Cys Asp Asp Pro Arg Val Ala Arg Trp Tyr Cys Gln Phe Val
1               5                   10                  15

Glu Gly

<210> SEQ ID NO 23
<211> LENGTH: 18
<212> TYPE: PRT
<213> ORGANISM: Artificial
<220> FEATURE:
<223> OTHER INFORMATION: Synthetic peptide sequence

<400> SEQUENCE: 23

Ala Leu Cys Asp Asp Pro Arg Val Glu Arg Trp Tyr Cys Gln Phe Val
1               5                   10                  15

Glu Gly

<210> SEQ ID NO 24
<211> LENGTH: 18
<212> TYPE: PRT
<213> ORGANISM: Artificial
<220> FEATURE:
<223> OTHER INFORMATION: Synthetic peptide sequence

<400> SEQUENCE: 24

Ala Leu Cys Asp Asp Pro Arg Val Asp Ala Trp Tyr Cys Gln Phe Val
1               5                   10                  15

Glu Gly

<210> SEQ ID NO 25
<211> LENGTH: 18
<212> TYPE: PRT
<213> ORGANISM: Artificial
<220> FEATURE:
<223> OTHER INFORMATION: Synthetic peptide sequence

<400> SEQUENCE: 25

Ala Leu Cys Asp Asp Pro Arg Val Asp Pro Trp Tyr Cys Gln Phe Val
```

```
1               5                   10                  15
Glu Gly

<210> SEQ ID NO 26
<211> LENGTH: 18
<212> TYPE: PRT
<213> ORGANISM: Artificial
<220> FEATURE:
<223> OTHER INFORMATION: Synthetic peptide sequence

<400> SEQUENCE: 26

Ala Leu Cys Asp Asp Pro Arg Val Asp Arg Ala Tyr Cys Gln Phe Val
1               5                   10                  15
Glu Gly

<210> SEQ ID NO 27
<211> LENGTH: 18
<212> TYPE: PRT
<213> ORGANISM: Artificial
<220> FEATURE:
<223> OTHER INFORMATION: Synthetic peptide sequence

<400> SEQUENCE: 27

Ala Leu Cys Asp Asp Pro Arg Val Asp Arg Trp Tyr Cys Gln Ala Val
1               5                   10                  15
Glu Gly

<210> SEQ ID NO 28
<211> LENGTH: 18
<212> TYPE: PRT
<213> ORGANISM: Artificial
<220> FEATURE:
<223> OTHER INFORMATION: Synthetic peptide sequence

<400> SEQUENCE: 28

Ala Leu Ala Asp Asp Pro Arg Val Asp Arg Trp Tyr Ala Gln Phe Val
1               5                   10                  15
Glu Gly

<210> SEQ ID NO 29
<211> LENGTH: 18
<212> TYPE: PRT
<213> ORGANISM: Artificial
<220> FEATURE:
<223> OTHER INFORMATION: Synthetic peptide sequence

<400> SEQUENCE: 29

Ala Leu Cys Asp Glu Pro Arg Val Asp Arg Trp Tyr Cys Gln Phe Val
1               5                   10                  15
Glu Gly

<210> SEQ ID NO 30
<211> LENGTH: 18
<212> TYPE: PRT
<213> ORGANISM: Artificial
<220> FEATURE:
<223> OTHER INFORMATION: Synthetic peptide sequence

<400> SEQUENCE: 30

Ala Leu Cys Asp Asp Pro Arg Ile Asp Arg Trp Tyr Cys Gln Phe Val
1               5                   10                  15
Glu Gly
```

```
<210> SEQ ID NO 31
<211> LENGTH: 18
<212> TYPE: PRT
<213> ORGANISM: Artificial
<220> FEATURE:
<223> OTHER INFORMATION: Synthetic peptide sequence

<400> SEQUENCE: 31

Ala Leu Cys Arg Asp Pro Arg Val Asp Arg Trp Tyr Cys Gln Phe Val
1               5                   10                  15

Glu Gly

<210> SEQ ID NO 32
<211> LENGTH: 18
<212> TYPE: PRT
<213> ORGANISM: Artificial
<220> FEATURE:
<223> OTHER INFORMATION: Synthetic peptide sequence

<400> SEQUENCE: 32

Ala Leu Cys Asp Asp Pro Arg Leu Asp Arg Trp Tyr Cys Gln Phe Val
1               5                   10                  15

Glu Gly

<210> SEQ ID NO 33
<211> LENGTH: 18
<212> TYPE: PRT
<213> ORGANISM: Artificial
<220> FEATURE:
<223> OTHER INFORMATION: Synthetic peptide sequence

<400> SEQUENCE: 33

Ala Leu Cys Asp Asp Pro Arg Ala Asp Arg Trp Tyr Cys Gln Phe Val
1               5                   10                  15

Glu Gly

<210> SEQ ID NO 34
<211> LENGTH: 18
<212> TYPE: PRT
<213> ORGANISM: Artificial
<220> FEATURE:
<223> OTHER INFORMATION: Synthetic peptide sequence

<400> SEQUENCE: 34

Ala Leu Cys Asp Asp Pro Arg Val Asp Lys Trp Tyr Cys Gln Phe Val
1               5                   10                  15

Glu Gly

<210> SEQ ID NO 35
<211> LENGTH: 18
<212> TYPE: PRT
<213> ORGANISM: Artificial
<220> FEATURE:
<223> OTHER INFORMATION: Synthetic peptide sequence

<400> SEQUENCE: 35

Ala Leu Cys Asp Asp Pro Arg Val Asp Arg Phe Tyr Cys Gln Phe Val
1               5                   10                  15

Glu Gly

<210> SEQ ID NO 36
<211> LENGTH: 18
<212> TYPE: PRT
```

```
<213> ORGANISM: Artificial
<220> FEATURE:
<223> OTHER INFORMATION: Synthetic peptide sequence

<400> SEQUENCE: 36

Ala Leu Cys Asp Asp Pro Arg Val Asp Arg Trp Tyr Cys Tyr Phe Val
1               5                   10                  15

Glu Gly

<210> SEQ ID NO 37
<211> LENGTH: 18
<212> TYPE: PRT
<213> ORGANISM: Artificial
<220> FEATURE:
<223> OTHER INFORMATION: Synthetic peptide sequence

<400> SEQUENCE: 37

Ala Leu Cys Asp Asp Pro Arg Val Asp Arg Trp Phe Cys Gln Phe Val
1               5                   10                  15

Glu Gly

<210> SEQ ID NO 38
<211> LENGTH: 18
<212> TYPE: PRT
<213> ORGANISM: Artificial
<220> FEATURE:
<223> OTHER INFORMATION: Synthetic peptide sequence

<400> SEQUENCE: 38

Ala Leu Cys Asp Asp Pro Arg Val Asp Arg Trp Ala Cys Gln Phe Val
1               5                   10                  15

Glu Gly

<210> SEQ ID NO 39
<211> LENGTH: 18
<212> TYPE: PRT
<213> ORGANISM: Artificial
<220> FEATURE:
<223> OTHER INFORMATION: Synthetic peptide sequence

<400> SEQUENCE: 39

Ala Leu Cys Asp Asp Pro Arg Val Asp Arg Trp Tyr Cys Gln Tyr Val
1               5                   10                  15

Glu Gly

<210> SEQ ID NO 40
<211> LENGTH: 20
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (20)..(20)
<223> OTHER INFORMATION: Lys has a derivatized side chain

<400> SEQUENCE: 40

Ala Leu Cys Asp Asp Pro Arg Val Asp Arg Trp Tyr Cys Gln Phe Val
1               5                   10                  15

Glu Gly Ser Lys
            20

<210> SEQ ID NO 41
<211> LENGTH: 18
```

```
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (11)..(11)
<223> OTHER INFORMATION: Xaa is 4-methylphenylalanine and wherein the
      side chains may interact as a helical lock
<220> FEATURE:
<221> NAME/KEY: MISC_FEATURE
<222> LOCATION: (18)..(18)
<223> OTHER INFORMATION: Xaa is 4-methylphenylalanine and wherein the
      side chains may interact as a helical lock

<400> SEQUENCE: 41

Ala Leu Cys Asp Asp Pro Arg Val Asp Arg Xaa Trp Cys Gln Lys Val
1               5                   10                  15

Glu Xaa

<210> SEQ ID NO 42
<211> LENGTH: 17
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (10)..(10)
<223> OTHER INFORMATION: Xaa is 4-methylphenylalanine and wherein the
      side chains may interact as a helical lock
<220> FEATURE:
<221> NAME/KEY: MISC_FEATURE
<222> LOCATION: (17)..(17)
<223> OTHER INFORMATION: Xaa is 4-methylphenylalanine and wherein the
      side chains may interact as a helical lock

<400> SEQUENCE: 42

Ala Leu Cys Asp Asp Pro Arg Val Asp Xaa Trp Tyr Cys Gln Phe Val
1               5                   10                  15

Xaa

<210> SEQ ID NO 43
<211> LENGTH: 18
<212> TYPE: PRT
<213> ORGANISM: Artificial
<220> FEATURE:
<223> OTHER INFORMATION: Synthetic peptide sequence

<400> SEQUENCE: 43

Ala Leu Cys Asp Asn Pro Arg Ile Asp Arg Trp Tyr Cys Gln Phe Val
1               5                   10                  15

Glu Gly

<210> SEQ ID NO 44
<211> LENGTH: 18
<212> TYPE: PRT
<213> ORGANISM: Artificial
<220> FEATURE:
<223> OTHER INFORMATION: Synthetic peptide sequence

<400> SEQUENCE: 44

Ala Leu Cys Asp Asp Pro Arg Val Asp Arg His Tyr Cys Gln Phe Val
1               5                   10                  15

Glu Gly

<210> SEQ ID NO 45
```

```
<211> LENGTH: 18
<212> TYPE: PRT
<213> ORGANISM: Artificial
<220> FEATURE:
<223> OTHER INFORMATION: Synthetic peptide sequence

<400> SEQUENCE: 45

Ala Ala Cys Asp Asp Pro Arg Val Asp Arg Trp Tyr Cys Gln Phe Val
1               5                   10                  15

Glu Gly

<210> SEQ ID NO 46
<211> LENGTH: 16
<212> TYPE: PRT
<213> ORGANISM: Artificial
<220> FEATURE:
<223> OTHER INFORMATION: Synthetic peptide sequence

<400> SEQUENCE: 46

Cys Asp Asp Pro Arg Val Asp Arg Trp Tyr Cys Gln Phe Val Glu Gly
1               5                   10                  15

<210> SEQ ID NO 47
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (9)..(9)
<223> OTHER INFORMATION: Xaa is ornithine

<400> SEQUENCE: 47

Ala Leu Cys Asp Asp Pro Arg Val Xaa Arg Trp Tyr Cys Gln Phe Val
1               5                   10                  15

Glu Gly

<210> SEQ ID NO 48
<211> LENGTH: 18
<212> TYPE: PRT
<213> ORGANISM: Artificial
<220> FEATURE:
<223> OTHER INFORMATION: Synthetic peptide sequence

<400> SEQUENCE: 48

Ala Leu Cys Asp Asp Pro Arg Val Gln Arg Trp Tyr Cys Gln Phe Val
1               5                   10                  15

Glu Gly

<210> SEQ ID NO 49
<211> LENGTH: 18
<212> TYPE: PRT
<213> ORGANISM: Artificial
<220> FEATURE:
<223> OTHER INFORMATION: Synthetic peptide sequence

<400> SEQUENCE: 49

Ala Leu Cys Asp Asp Pro Arg Val Ser Arg Trp Tyr Cys Gln Phe Val
1               5                   10                  15

Glu Gly

<210> SEQ ID NO 50
<211> LENGTH: 18
<212> TYPE: PRT
```

<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (11)..(11)
<223> OTHER INFORMATION: Xaa is Beta-Napthylalanine

<400> SEQUENCE: 50

Ala Leu Cys Asp Asp Pro Arg Val Asp Arg Xaa Tyr Cys Gln Phe Val
1               5                   10                  15

Glu Gly

<210> SEQ ID NO 51
<211> LENGTH: 18
<212> TYPE: PRT
<213> ORGANISM: Artificial
<220> FEATURE:
<223> OTHER INFORMATION: Synthetic peptide sequence

<400> SEQUENCE: 51

Ala Leu Cys Asp Asp Ala Arg Val Asp Arg Trp Tyr Cys Gln Phe Val
1               5                   10                  15

Glu Gly

<210> SEQ ID NO 52
<211> LENGTH: 18
<212> TYPE: PRT
<213> ORGANISM: Artificial
<220> FEATURE:
<223> OTHER INFORMATION: Synthetic peptide sequence

<400> SEQUENCE: 52

Ala Leu Cys Asp Asp Pro Arg Val Asp Arg Trp Tyr Cys Ala Phe Val
1               5                   10                  15

Glu Gly

<210> SEQ ID NO 53
<211> LENGTH: 13
<212> TYPE: PRT
<213> ORGANISM: Artificial
<220> FEATURE:
<223> OTHER INFORMATION: Synthetic peptide sequence

<400> SEQUENCE: 53

Ala Leu Cys Asp Asp Pro Arg Val Asp Arg Trp Tyr Cys
1               5                   10

<210> SEQ ID NO 54
<211> LENGTH: 18
<212> TYPE: PRT
<213> ORGANISM: Artificial
<220> FEATURE:
<223> OTHER INFORMATION: Synthetic peptide sequence

<400> SEQUENCE: 54

Ala Leu Cys Asp Asp Pro Arg Val Asp Arg Trp Tyr Cys Gln Leu Val
1               5                   10                  15

Glu Gly

<210> SEQ ID NO 55
<211> LENGTH: 18
<212> TYPE: PRT
<213> ORGANISM: Artificial
<220> FEATURE:

```
<223> OTHER INFORMATION: Synthetic peptide sequence
<220> FEATURE:
<221> NAME/KEY: MISC_FEATURE
<222> LOCATION: (15)..(15)
<223> OTHER INFORMATION: Xaa is norleucine

<400> SEQUENCE: 55

Ala Leu Cys Asp Asp Pro Arg Val Asp Arg Trp Tyr Cys Gln Xaa Val
1               5                   10                  15

Glu Gly

<210> SEQ ID NO 56
<211> LENGTH: 18
<212> TYPE: PRT
<213> ORGANISM: Artificial
<220> FEATURE:
<223> OTHER INFORMATION: Synthetic peptide sequence

<400> SEQUENCE: 56

Ala Leu Cys Asp Asp Pro Arg Val Asp Arg Trp Tyr Cys Gln Gln Val
1               5                   10                  15

Glu Gly

<210> SEQ ID NO 57
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa is metatyrosine

<400> SEQUENCE: 57

Ala Leu Cys Asp Asp Pro Arg Val Asp Arg Trp Xaa Cys Gln Phe Val
1               5                   10                  15

Glu Gly

<210> SEQ ID NO 58
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa is gamma-carboxyglutamic acid

<400> SEQUENCE: 58

Ala Leu Cys Asp Asp Pro Arg Val Asp Arg Trp Xaa Cys Gln Phe Val
1               5                   10                  15

Glu Gly

<210> SEQ ID NO 59
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (9)..(9)
<223> OTHER INFORMATION: Xaa is gamma-carboxyglutamic acid
<220> FEATURE:
<221> NAME/KEY: MISC_FEATURE
```

-continued

```
<222> LOCATION: (12)..(12)
<223> OTHER INFORMATION: Xaa is metatyrosine

<400> SEQUENCE: 59

Ala Leu Cys Asp Asp Pro Arg Val Xaa Arg Trp Xaa Cys Gln Phe Val
1               5                   10                  15

Glu Gly

<210> SEQ ID NO 60
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (10)..(10)
<223> OTHER INFORMATION: A helical lock between side chains of residues
      Glu 10 and Lys 14
<220> FEATURE:
<221> NAME/KEY: MISC_FEATURE
<222> LOCATION: (14)..(14)
<223> OTHER INFORMATION: A helical lock between side chains of residues
      Glu 10 and Lys 14

<400> SEQUENCE: 60

Ala Leu Cys Asp Asp Pro Arg Val Asp Glu Trp Tyr Cys Lys Phe Val
1               5                   10                  15

Glu Gly

<210> SEQ ID NO 61
<211> LENGTH: 18
<212> TYPE: PRT
<213> ORGANISM: Artificial
<220> FEATURE:
<223> OTHER INFORMATION: Synthetic peptide sequence

<400> SEQUENCE: 61

Ala Val Cys Asp Asp Pro Arg Val Asp Arg Trp Tyr Cys Gln Phe Val
1               5                   10                  15

Glu Gly

<210> SEQ ID NO 62
<211> LENGTH: 18
<212> TYPE: PRT
<213> ORGANISM: Artificial
<220> FEATURE:
<223> OTHER INFORMATION: Synthetic peptide sequence

<400> SEQUENCE: 62

Ala Thr Cys Asp Asp Pro Arg Val Asp Arg Trp Tyr Cys Gln Phe Val
1               5                   10                  15

Glu Gly

<210> SEQ ID NO 63
<211> LENGTH: 18
<212> TYPE: PRT
<213> ORGANISM: Artificial
<220> FEATURE:
<223> OTHER INFORMATION: Synthetic peptide sequence

<400> SEQUENCE: 63

Ala Met Cys Asp Asp Pro Arg Val Asp Arg Trp Tyr Cys Gln Phe Val
1               5                   10                  15

Glu Gly
```

<210> SEQ ID NO 64
<211> LENGTH: 18
<212> TYPE: PRT
<213> ORGANISM: Artificial
<220> FEATURE:
<223> OTHER INFORMATION: Synthetic peptide sequence

<400> SEQUENCE: 64

Ala Lys Cys Asp Asp Pro Arg Val Asp Arg Trp Tyr Cys Gln Phe Val
1               5                   10                  15

Glu Gly

<210> SEQ ID NO 65
<211> LENGTH: 20
<212> TYPE: PRT
<213> ORGANISM: Artificial
<220> FEATURE:
<223> OTHER INFORMATION: Synthetic peptide sequence

<400> SEQUENCE: 65

Glu Ala Ala Leu Cys Glu Asp Pro Arg Val Asp Arg Trp Tyr Cys Ile
1               5                   10                  15

Phe Ala Gly Glu
            20

<210> SEQ ID NO 66
<211> LENGTH: 20
<212> TYPE: PRT
<213> ORGANISM: Artificial
<220> FEATURE:
<223> OTHER INFORMATION: Synthetic peptide sequence

<400> SEQUENCE: 66

Glu Ser Ala Leu Cys Asp Asp Pro Arg Val Asp Arg Trp Tyr Cys Ile
1               5                   10                  15

Phe Ala Gly Asp
            20

<210> SEQ ID NO 67
<211> LENGTH: 20
<212> TYPE: PRT
<213> ORGANISM: Artificial
<220> FEATURE:
<223> OTHER INFORMATION: Synthetic peptide sequence

<400> SEQUENCE: 67

Glu Val Ala Leu Cys Ser Asp Pro Arg Val Asp Arg Trp Tyr Cys Met
1               5                   10                  15

Phe Ala Thr Asp
            20

<210> SEQ ID NO 68
<211> LENGTH: 20
<212> TYPE: PRT
<213> ORGANISM: Artificial
<220> FEATURE:
<223> OTHER INFORMATION: Synthetic peptide sequence

<400> SEQUENCE: 68

Ala Ala Ala Leu Cys Asp Asp Pro Arg Ile Asp Arg Trp Tyr Cys Ser
1               5                   10                  15

Phe Leu Gly Val
            20

```
<210> SEQ ID NO 69
<211> LENGTH: 20
<212> TYPE: PRT
<213> ORGANISM: Artificial
<220> FEATURE:
<223> OTHER INFORMATION: Synthetic peptide sequence

<400> SEQUENCE: 69

Glu Ala Ala Leu Cys Asp Asp Pro Arg Phe Asp Arg Trp Tyr Cys Thr
1               5                   10                  15

Phe Val Gly Glu
            20

<210> SEQ ID NO 70
<211> LENGTH: 20
<212> TYPE: PRT
<213> ORGANISM: Artificial
<220> FEATURE:
<223> OTHER INFORMATION: Synthetic peptide sequence

<400> SEQUENCE: 70

Glu Ala Ala Leu Cys Asp Asp Pro Arg Val Asp Arg Trp Tyr Cys Thr
1               5                   10                  15

Phe Val Gly Glu
            20

<210> SEQ ID NO 71
<211> LENGTH: 18
<212> TYPE: PRT
<213> ORGANISM: Artificial
<220> FEATURE:
<223> OTHER INFORMATION: Synthetic peptide sequence

<400> SEQUENCE: 71

Asn Arg Ser Leu Cys Asn Asp Pro Arg Val Asp Arg Trp Tyr Cys Asn
1               5                   10                  15

Phe Ser

<210> SEQ ID NO 72
<211> LENGTH: 18
<212> TYPE: PRT
<213> ORGANISM: Artificial
<220> FEATURE:
<223> OTHER INFORMATION: Synthetic peptide sequence

<400> SEQUENCE: 72

Gln Ser Arg Leu Cys Asp Asp Pro Arg Ile Asp Arg Trp Tyr Cys Gln
1               5                   10                  15

Phe Gly

<210> SEQ ID NO 73
<211> LENGTH: 18
<212> TYPE: PRT
<213> ORGANISM: Artificial
<220> FEATURE:
<223> OTHER INFORMATION: Synthetic peptide sequence

<400> SEQUENCE: 73

Glu Ala Ala Leu Cys Asp Asp Pro Arg Ile Asp Arg Trp Tyr Cys Gly
1               5                   10                  15

Phe Leu
```

-continued

```
<210> SEQ ID NO 74
<211> LENGTH: 18
<212> TYPE: PRT
<213> ORGANISM: Artificial
<220> FEATURE:
<223> OTHER INFORMATION: Synthetic peptide sequence

<400> SEQUENCE: 74

Tyr Gln Phe Leu Cys Asp Asp Pro Arg Ile Asp Arg Trp Tyr Cys Lys
1               5                   10                  15

Phe Val

<210> SEQ ID NO 75
<211> LENGTH: 18
<212> TYPE: PRT
<213> ORGANISM: Artificial
<220> FEATURE:
<223> OTHER INFORMATION: Synthetic peptide sequence

<400> SEQUENCE: 75

Trp Gly Thr Leu Cys Asp Asp Pro Arg Ile Asp Arg Trp Tyr Cys Arg
1               5                   10                  15

Phe Ser

<210> SEQ ID NO 76
<211> LENGTH: 18
<212> TYPE: PRT
<213> ORGANISM: Artificial
<220> FEATURE:
<223> OTHER INFORMATION: Synthetic peptide sequence

<400> SEQUENCE: 76

Val Lys Ala Leu Cys Val Asp Pro Arg Ile Asp Arg Trp Tyr Cys Gln
1               5                   10                  15

Phe Thr

<210> SEQ ID NO 77
<211> LENGTH: 18
<212> TYPE: PRT
<213> ORGANISM: Artificial
<220> FEATURE:
<223> OTHER INFORMATION: Synthetic peptide sequence

<400> SEQUENCE: 77

Gly Leu Cys Asp Asp Pro Arg Val Asp Arg Trp Tyr Cys Gln Phe Gln
1               5                   10                  15

Val Leu

<210> SEQ ID NO 78
<211> LENGTH: 17
<212> TYPE: PRT
<213> ORGANISM: Artificial
<220> FEATURE:
<223> OTHER INFORMATION: Synthetic peptide sequence

<400> SEQUENCE: 78

Asn Leu Cys Ser Asp Pro Arg Val Asp Arg Trp Tyr Cys Gln Phe Ile
1               5                   10                  15

Arg

<210> SEQ ID NO 79
<211> LENGTH: 18
<212> TYPE: PRT
<213> ORGANISM: Artificial
```

```
<220> FEATURE:
<223> OTHER INFORMATION: Synthetic peptide sequence

<400> SEQUENCE: 79

Ser Leu Cys Asp Asp Pro Arg Val Asp Arg Trp Tyr Cys Gly Phe Val
1               5                   10                  15

Glu Val

<210> SEQ ID NO 80
<211> LENGTH: 18
<212> TYPE: PRT
<213> ORGANISM: Artificial
<220> FEATURE:
<223> OTHER INFORMATION: Synthetic peptide sequence

<400> SEQUENCE: 80

Ala Leu Cys Asp Asp Pro Arg Val Asp Arg Trp Tyr Cys Leu Phe Val
1               5                   10                  15

Glu Gly

<210> SEQ ID NO 81
<211> LENGTH: 18
<212> TYPE: PRT
<213> ORGANISM: Artificial
<220> FEATURE:
<223> OTHER INFORMATION: Synthetic peptide sequence

<400> SEQUENCE: 81

Ala Leu Cys His Asp Pro Arg Val Asp Arg Trp Tyr Cys Met Phe Met
1               5                   10                  15

Glu Asp

<210> SEQ ID NO 82
<211> LENGTH: 18
<212> TYPE: PRT
<213> ORGANISM: Artificial
<220> FEATURE:
<223> OTHER INFORMATION: Synthetic peptide sequence

<400> SEQUENCE: 82

Thr Leu Cys Ser Asp Pro Arg Val Asp Arg Trp Tyr Cys Arg Phe Ala
1               5                   10                  15

Glu Gly

<210> SEQ ID NO 83
<211> LENGTH: 16
<212> TYPE: PRT
<213> ORGANISM: Artificial
<220> FEATURE:
<223> OTHER INFORMATION: Synthetic peptide sequence

<400> SEQUENCE: 83

Thr Leu Cys Ala Asp Pro Arg Val Asp Arg Trp Tyr Cys Gln Phe Thr
1               5                   10                  15

<210> SEQ ID NO 84
<211> LENGTH: 16
<212> TYPE: PRT
<213> ORGANISM: Artificial
<220> FEATURE:
<223> OTHER INFORMATION: Synthetic peptide sequence

<400> SEQUENCE: 84

Asn Leu Cys Ala Asp Pro Arg Val Asp Arg Trp Tyr Cys Lys Phe Val
```

```
                1               5                   10                  15
```

<210> SEQ ID NO 85
<211> LENGTH: 16
<212> TYPE: PRT
<213> ORGANISM: Artificial
<220> FEATURE:
<223> OTHER INFORMATION: Synthetic peptide sequence

<400> SEQUENCE: 85

```
Arg Leu Cys Asp Asp Pro Arg Val Asp Arg Trp Tyr Cys Gln Phe Gly
1               5                   10                  15
```

<210> SEQ ID NO 86
<211> LENGTH: 16
<212> TYPE: PRT
<213> ORGANISM: Artificial
<220> FEATURE:
<223> OTHER INFORMATION: Synthetic peptide sequence

<400> SEQUENCE: 86

```
Ser Leu Cys Glu Asp Pro Arg Val Asp Arg Trp Tyr Cys Gln Phe Thr
1               5                   10                  15
```

<210> SEQ ID NO 87
<211> LENGTH: 16
<212> TYPE: PRT
<213> ORGANISM: Artificial
<220> FEATURE:
<223> OTHER INFORMATION: Synthetic peptide sequence

<400> SEQUENCE: 87

```
Thr Leu Cys Glu Asp Pro Arg Val Asp Arg Trp Tyr Cys Gln Phe Val
1               5                   10                  15
```

<210> SEQ ID NO 88
<211> LENGTH: 16
<212> TYPE: PRT
<213> ORGANISM: Artificial
<220> FEATURE:
<223> OTHER INFORMATION: Synthetic peptide sequence

<400> SEQUENCE: 88

```
Ser Leu Cys Asp Asp Pro Arg Val Asp Arg Trp Tyr Cys Gln Phe Ala
1               5                   10                  15
```

<210> SEQ ID NO 89
<211> LENGTH: 16
<212> TYPE: PRT
<213> ORGANISM: Artificial
<220> FEATURE:
<223> OTHER INFORMATION: Synthetic peptide sequence

<400> SEQUENCE: 89

```
Pro Leu Cys Ser Asp Pro Arg Val Asp Arg Trp Tyr Cys Gln Phe Ser
1               5                   10                  15
```

<210> SEQ ID NO 90
<211> LENGTH: 16
<212> TYPE: PRT
<213> ORGANISM: Artificial
<220> FEATURE:
<223> OTHER INFORMATION: Synthetic peptide sequence

<400> SEQUENCE: 90

```
Ser Leu Cys Met Asp Pro Arg Ile Asp Arg Trp Tyr Cys Thr Phe Val
1               5                   10                  15
```

<210> SEQ ID NO 91
<211> LENGTH: 16
<212> TYPE: PRT
<213> ORGANISM: Artificial
<220> FEATURE:
<223> OTHER INFORMATION: Synthetic peptide sequence

<400> SEQUENCE: 91

Thr Leu Cys Asp Asp Pro Arg Val Asp Arg Trp Tyr Cys Gln Phe Thr
1               5                   10                  15

<210> SEQ ID NO 92
<211> LENGTH: 20
<212> TYPE: PRT
<213> ORGANISM: Artificial
<220> FEATURE:
<223> OTHER INFORMATION: Synthetic peptide sequence

<400> SEQUENCE: 92

Gly Glu Ala Leu Cys Thr Asp Pro Arg Val Asp Arg Trp Tyr Cys Gln
1               5                   10                  15

Phe His Val His
            20

<210> SEQ ID NO 93
<211> LENGTH: 20
<212> TYPE: PRT
<213> ORGANISM: Artificial
<220> FEATURE:
<223> OTHER INFORMATION: Synthetic peptide sequence

<400> SEQUENCE: 93

Tyr Arg Ser Leu Cys Ser Asp Pro Arg Ile Asp Arg Trp Tyr Cys Gln
1               5                   10                  15

Phe Ile Gly Asp
            20

<210> SEQ ID NO 94
<211> LENGTH: 20
<212> TYPE: PRT
<213> ORGANISM: Artificial
<220> FEATURE:
<223> OTHER INFORMATION: Synthetic peptide sequence

<400> SEQUENCE: 94

Thr Gly Ala Leu Cys Glu Asp Pro Arg Val Asp Arg Trp Tyr Cys Ala
1               5                   10                  15

Phe Val Glu Gln
            20

<210> SEQ ID NO 95
<211> LENGTH: 20
<212> TYPE: PRT
<213> ORGANISM: Artificial
<220> FEATURE:
<223> OTHER INFORMATION: Synthetic peptide sequence

<400> SEQUENCE: 95

Met Thr Ala Leu Cys Glu Asp Pro Arg Val Asp Arg Trp Tyr Cys Ser
1               5                   10                  15

Phe Met Pro Gly
            20

```
<210> SEQ ID NO 96
<211> LENGTH: 20
<212> TYPE: PRT
<213> ORGANISM: Artificial
<220> FEATURE:
<223> OTHER INFORMATION: Synthetic peptide sequence

<400> SEQUENCE: 96

Val Thr Ser Leu Cys Ser Asp Pro Arg Val Asp Arg Trp Tyr Cys Ser
1               5                   10                  15

Phe Leu Ser Glu
            20

<210> SEQ ID NO 97
<211> LENGTH: 20
<212> TYPE: PRT
<213> ORGANISM: Artificial
<220> FEATURE:
<223> OTHER INFORMATION: Synthetic peptide sequence

<400> SEQUENCE: 97

Gly Ala Ala Leu Cys Asp Asp Pro Arg Val Asp Arg Trp Tyr Cys Gln
1               5                   10                  15

Phe Ser Ile Gly
            20

<210> SEQ ID NO 98
<211> LENGTH: 20
<212> TYPE: PRT
<213> ORGANISM: Artificial
<220> FEATURE:
<223> OTHER INFORMATION: Synthetic peptide sequence

<400> SEQUENCE: 98

Val Arg Ala Leu Cys Glu Asp Pro Arg Val Asp Arg Trp Tyr Cys Arg
1               5                   10                  15

Phe Val Asp Ile
            20

<210> SEQ ID NO 99
<211> LENGTH: 20
<212> TYPE: PRT
<213> ORGANISM: Artificial
<220> FEATURE:
<223> OTHER INFORMATION: Synthetic peptide sequence

<400> SEQUENCE: 99

Thr Val Ala Leu Cys Glu Asp Pro Arg Val Asp Arg Trp Tyr Cys Gln
1               5                   10                  15

Phe Phe Glu Tyr
            20

<210> SEQ ID NO 100
<211> LENGTH: 20
<212> TYPE: PRT
<213> ORGANISM: Artificial
<220> FEATURE:
<223> OTHER INFORMATION: Synthetic peptide sequence

<400> SEQUENCE: 100

Ile Val Gln Leu Cys Asp Asp Pro Arg Val Asp Arg Trp Tyr Cys Gln
1               5                   10                  15

Phe Ala Lys Pro
            20
```

```
<210> SEQ ID NO 101
<211> LENGTH: 20
<212> TYPE: PRT
<213> ORGANISM: Artificial
<220> FEATURE:
<223> OTHER INFORMATION: Synthetic peptide sequence

<400> SEQUENCE: 101

Asn Gly Ser Leu Cys Asp Asp Pro Arg Ile Asp Arg Trp Tyr Cys Gly
1               5                   10                  15

Phe Ile Glu Tyr
            20

<210> SEQ ID NO 102
<211> LENGTH: 84
<212> TYPE: DNA
<213> ORGANISM: Artificial
<220> FEATURE:
<223> OTHER INFORMATION: Synthetic Oligonucleotide

<400> SEQUENCE: 102
cgcgcccagg tgtacgagtc ctggggatgc atcggccccg gctgcgcctg cctgcaggcc      60
tgcctgggag gcgggagctc cggc                                            84

<210> SEQ ID NO 103
<211> LENGTH: 80
<212> TYPE: DNA
<213> ORGANISM: Artificial
<220> FEATURE:
<223> OTHER INFORMATION: Synthetic Oligonucleotide

<400> SEQUENCE: 103
gccggagctc ccgcctccca ggcaggcctg caggcaggcg cagccggggc cgatgcatcc      60
ccaggactcg tacacctggg                                                 80

<210> SEQ ID NO 104
<211> LENGTH: 6
<212> TYPE: PRT
<213> ORGANISM: Artificial
<220> FEATURE:
<223> OTHER INFORMATION: Peptide linker

<400> SEQUENCE: 104

Gly Gly Gly Ser Ser Gly
1               5

<210> SEQ ID NO 105
<211> LENGTH: 17
<212> TYPE: PRT
<213> ORGANISM: Artificial
<220> FEATURE:
<223> OTHER INFORMATION: Synthetic peptide sequence
<220> FEATURE:
<221> NAME/KEY: MUTAGEN
<222> LOCATION: (1)..(1)
<223> OTHER INFORMATION: absent or more than one amino acid possible
<220> FEATURE:
<221> NAME/KEY: MUTAGEN
<222> LOCATION: (5)..(6)
<223> OTHER INFORMATION: more than one amino acid possible
<220> FEATURE:
<221> NAME/KEY: MUTAGEN
<222> LOCATION: (9)..(9)
<223> OTHER INFORMATION: more than one amino acid possible
<220> FEATURE:
<221> NAME/KEY: MUTAGEN
<222> LOCATION: (12)..(12)
```

```
<223> OTHER INFORMATION: more than one amino acid possible
<220> FEATURE:
<221> NAME/KEY: MUTAGEN
<222> LOCATION: (15)..(15)
<223> OTHER INFORMATION: more than one amino acid possible
<220> FEATURE:
<221> NAME/KEY: MUTAGEN
<222> LOCATION: (17)..(17)
<223> OTHER INFORMATION: more than one amino acid possible

<400> SEQUENCE: 105

Xaa Ala Leu Cys Xaa Xaa Pro Arg Xaa Asp Arg Xaa Tyr Cys Xaa Phe
1               5                   10                  15

Xaa

<210> SEQ ID NO 106
<211> LENGTH: 17
<212> TYPE: PRT
<213> ORGANISM: Artificial
<220> FEATURE:
<223> OTHER INFORMATION: Synthetic peptide sequence
<220> FEATURE:
<221> NAME/KEY: MUTAGEN
<222> LOCATION: (1)..(1)
<223> OTHER INFORMATION: absent or more than one amino acid possible
<220> FEATURE:
<221> NAME/KEY: MUTAGEN
<222> LOCATION: (2)..(5)
<223> OTHER INFORMATION: more than one amino acid possible
<220> FEATURE:
<221> NAME/KEY: MUTAGEN
<222> LOCATION: (9)..(9)
<223> OTHER INFORMATION: more than one amino acid possible
<220> FEATURE:
<221> NAME/KEY: MUTAGEN
<222> LOCATION: (14)..(17)
<223> OTHER INFORMATION: more than one amino acid possible

<400> SEQUENCE: 106

Xaa Xaa Xaa Xaa Xaa Asp Pro Arg Xaa Asp Arg Trp Tyr Xaa Xaa Xaa
1               5                   10                  15

Xaa

<210> SEQ ID NO 107
<211> LENGTH: 17
<212> TYPE: PRT
<213> ORGANISM: Artificial
<220> FEATURE:
<223> OTHER INFORMATION: Synthetic peptide sequence
<220> FEATURE:
<221> NAME/KEY: MUTAGEN
<222> LOCATION: (1)..(1)
<223> OTHER INFORMATION: absent or more than one amino acid possible
<220> FEATURE:
<221> NAME/KEY: MUTAGEN
<222> LOCATION: (2)..(2)
<223> OTHER INFORMATION: more than one amino acid possible
<220> FEATURE:
<221> NAME/KEY: MUTAGEN
<222> LOCATION: (5)..(5)
<223> OTHER INFORMATION: more than one amino acid possible
<220> FEATURE:
<221> NAME/KEY: MUTAGEN
<222> LOCATION: (9)..(9)
<223> OTHER INFORMATION: more than one amino acid possible
<220> FEATURE:
<221> NAME/KEY: MUTAGEN
<222> LOCATION: (15)..(17)
<223> OTHER INFORMATION: more than one amino acid possible

<400> SEQUENCE: 107

Xaa Xaa Leu Cys Xaa Asp Pro Arg Xaa Asp Arg Trp Tyr Cys Xaa Xaa
```

```
1               5                  10                 15

Xaa

<210> SEQ ID NO 108
<211> LENGTH: 19
<212> TYPE: PRT
<213> ORGANISM: Artificial
<220> FEATURE:
<223> OTHER INFORMATION: Synthetic peptide sequence
<220> FEATURE:
<221> NAME/KEY: MUTAGEN
<222> LOCATION: (1)..(1)
<223> OTHER INFORMATION: absent or more than one amino acid possible
<220> FEATURE:
<221> NAME/KEY: MUTAGEN
<222> LOCATION: (5)..(5)
<223> OTHER INFORMATION: more than one amino acid possible
<220> FEATURE:
<221> NAME/KEY: MUTAGEN
<222> LOCATION: (9)..(9)
<223> OTHER INFORMATION: more than one amino acid possible
<220> FEATURE:
<221> NAME/KEY: MUTAGEN
<222> LOCATION: (15)..(15)
<223> OTHER INFORMATION: more than one amino acid possible
<220> FEATURE:
<221> NAME/KEY: MUTAGEN
<222> LOCATION: (17)..(19)
<223> OTHER INFORMATION: more than one amino acid possible

<400> SEQUENCE: 108

Xaa Ala Leu Cys Xaa Asp Pro Arg Xaa Asp Arg Trp Tyr Cys Xaa Phe
1               5                  10                 15

Xaa Xaa Xaa

<210> SEQ ID NO 109
<211> LENGTH: 14
<212> TYPE: PRT
<213> ORGANISM: Artificial
<220> FEATURE:
<223> OTHER INFORMATION: Synthetic peptide sequence

<400> SEQUENCE: 109

Leu Cys Asp Asp Pro Arg Val Asp Arg Trp Tyr Cys Gln Phe
1               5                  10

<210> SEQ ID NO 110
<211> LENGTH: 19
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (1)..(1)
<223> OTHER INFORMATION: Xaa is aminocaproic acid

<400> SEQUENCE: 110

Xaa Ala Leu Cys Asp Asp Pro Arg Val Asp Arg Trp Tyr Cys Gln Phe
1               5                  10                 15

Val Glu Gly

<210> SEQ ID NO 111
<211> LENGTH: 17
<212> TYPE: PRT
<213> ORGANISM: Artificial
<220> FEATURE:
<223> OTHER INFORMATION: Synthetic peptide sequence
```

-continued

```
<400> SEQUENCE: 111

Ala Leu Cys Asp Asp Pro Arg Val Asp Arg Trp Tyr Cys Gln Phe Val
1               5                   10                  15

Glu

<210> SEQ ID NO 112
<211> LENGTH: 17
<212> TYPE: PRT
<213> ORGANISM: Artificial
<220> FEATURE:
<223> OTHER INFORMATION: Synthetic peptide sequence

<400> SEQUENCE: 112

Ala Leu Cys Asp Asp Pro Arg Val Asp Arg Trp Tyr Cys Gln Phe Val
1               5                   10                  15

Glu

<210> SEQ ID NO 113
<211> LENGTH: 20
<212> TYPE: PRT
<213> ORGANISM: Artificial
<220> FEATURE:
<223> OTHER INFORMATION: Synthetic peptide sequence

<400> SEQUENCE: 113

Ala Leu Cys Asp Asp Pro Arg Val Asp Arg Trp Tyr Cys Gln Phe Val
1               5                   10                  15

Glu Gly Ser Lys
            20

<210> SEQ ID NO 114
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (15)..(15)
<223> OTHER INFORMATION: Xaa is metatyrosine

<400> SEQUENCE: 114

Ala Leu Cys Asp Asp Pro Arg Val Asp Arg Trp Tyr Cys Gln Xaa Val
1               5                   10                  15

Glu Gly

<210> SEQ ID NO 115
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (9)..(9)
<223> OTHER INFORMATION: Xaa is gamma-carboxyglutamic acid

<400> SEQUENCE: 115

Ala Leu Cys Asp Asp Pro Arg Val Xaa Arg Trp Tyr Cys Gln Phe Val
1               5                   10                  15

Glu Gly

<210> SEQ ID NO 116
<211> LENGTH: 18
```

```
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa is 4-methyl phenylalanine

<400> SEQUENCE: 116

Ala Leu Cys Asp Asp Pro Arg Val Asp Arg Trp Xaa Cys Gln Phe Val
1               5                   10                  15

Glu Gly

<210> SEQ ID NO 117
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa is 4-amino phenylalanine

<400> SEQUENCE: 117

Ala Leu Cys Asp Asp Pro Arg Val Asp Arg Trp Xaa Cys Gln Phe Val
1               5                   10                  15

Glu Gly

<210> SEQ ID NO 118
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (12)..(12)
<223> OTHER INFORMATION: Xaa is 3-(3,4-dihydroxphenyl) alanine

<400> SEQUENCE: 118

Ala Leu Cys Asp Asp Pro Arg Val Asp Arg Trp Xaa Cys Gln Phe Val
1               5                   10                  15

Glu Gly

<210> SEQ ID NO 119
<211> LENGTH: 18
<212> TYPE: PRT
<213> ORGANISM: Artificial
<220> FEATURE:
<223> OTHER INFORMATION: Synthetic peptide sequence
<220> FEATURE:
<221> NAME/KEY: MISC_FEATURE
<222> LOCATION: (10)..(10)
<223> OTHER INFORMATION: Sidechains of Lys interact as a helical lock
<220> FEATURE:
<221> NAME/KEY: MISC_FEATURE
<222> LOCATION: (14)..(14)
<223> OTHER INFORMATION: Sidechains of Glu interact as a helical lock

<400> SEQUENCE: 119

Ala Leu Cys Asp Asp Pro Arg Val Asp Lys Trp Tyr Cys Glu Phe Val
1               5                   10                  15

Glu Gly
```

FVIIA ANTAGONISTS

RELATED APPLICATIONS

This is a continuation of application Ser. No. 09/609,574 filed Jun. 30, 2000 which is a non-provisional application filed under 37 CFR 1.53(b), now abandoned claiming priority under USC Section 119(e) to provisional Application Ser. No. 60/142,211, filed on Jul. 2, 1999, both disclosures of which are hereby incorporated by reference.

BACKGROUND OF THE INVENTION

1. Field of the Invention

This invention relates to novel compounds which prevent or block a FVIIa mediated or associated process or event such as the catalytic conversion of FX to FXa, FVII to FVIIa or FIX to FIXa. In particular aspects, the compounds of the invention bind Factor VIIa (FVIIa), its zymogen Factor VII (FVII) and/or block the association of FVII or FVIIa with a peptide compound of the present invention. The invention also relates to pharmaceutical compositions comprising the novel compounds as well as their use in research, diagnostic, therapeutic, and prophylactic methods.

2. Description of Related Disclosures

Factor VIIa (FVIIa) is a trypsin-like plasma serine protease that participates in hemostasis through the extrinsic pathway of the coagulation cascade (Davie et al., (1991) Biochem. 30(43):10363–10370). FVIIa is converted from its zymogen factor VII (FVII) by proteolysis of a single internal peptide bond. Circulating FVII is a globular protein with an N-terminal γ-carboxyglutamic acid (Gla)-domain, two epidermal growth factor (EGF) domains, and a C-terminal protease domain. Prior to conversion to FVIIa, FVII associates with tissue factor (TF) constitutively expressed on cells separated from plasma by the vascular endothelium (Carson, S. D. and J. P. Brozna, (1993) Blood Coag. Fibrinol. 4:281–292). TF and FVII form a one-to-one protein complex (TF-FVIIa) in the presence of calcium ions (Wildgoose et al., (1993) Biochem. 32:114–119). This association facilitates the proteolysis of FVII to FVIIa at a site (Arg152-Ile153 for human FVII (hFVII)) located between the C-terminal EGF domain (EGF2) and the protease domain (Hagen et al., (1986) Proc. Natl. Acad. Sci USA, 83:2412–2416). While a number of serine proteases activate FVII in vitro, the protease responsible for in vivo activation of FVII is not known (Wildgoose et al., supra).

TF functions as a cofactor for FVIIa with the FVIIa Gla domain interacting at the C-terminal end of TF near the membrane and the FVIIa protease domain situated over the N-terminal domain (Higashi et al., (1994) J. Biol. Chem. 269:18891–18898). The structures of the human TF (hTF) extracellular domain and its complex with active site inhibited FVIIa have recently been determined by x-ray crystallography (Harlos et al., (1994) Nature 370:662–666; Muller et al., (1994) Biochemistry 33:10864; Banner et al., (1996) Nature 380:41–46).

The TF-FVIIa complex constitutes the primary initiator of the extrinsic pathway of blood coagulation (Carson, S. D. and Brozna, J. P., (1993) Blood Coag. Fibrinol. 4:281–292; Davie, E. W. et al., (1991) Biochemistry 30:10363–10370; Rapaport, S. I. and L. V. M. Rao, (1992) Arterioscler. Thromb. 12:1111–1121). The complex initiates the extrinsic pathway by activation of FX to Factor Xa (FXa), FIX to Factor IXa (FIXa), and additional FVII to FVIIa. The action of TF-FVIIa leads ultimately to the conversion of prothrombin to thrombin, which carries out many biological functions (Badimon, L. et al., (1991) Trends Cardiovasc. Med. 1:261–267). Among the most important functions of thrombin is the conversion of fibrinogen to fibrin, which polymerizes to form a clot. The TF-FVIIa complex also participates as a secondary factor in extending the physiological effects of the contact activation system.

The involvement of these plasma protease systems have been suggested to play a significant role in a variety of clinical manifestations including arterial and venous thrombosis, septic shock, adult respiratory distress syndrome (ARDS), disseminated intravascular coagulation (DIC) and various other disease states (Haskel, E. J. et al., (1991) Circulation 84:821–827); Holst, J. et al., (1993) Haemostasis 23 (suppl. 1):112–117; Creasey, A. A. et al., (1993) J. Clin. Invest. 91:2850–2860; see also, Colman R. W. (1989) N. Engl. J. Med 320:1207–1209; Bone, R. C. (1992) Arch. Intern. Med. 152:1381–1389).

Antibodies reactive with the protease domain of FVII have been shown to inhibit TF-FVIIa proteolytic function (Dickinson et al., (1998) J. Mol. Biol. 277:959–971). Peptides corresponding to the EGF2 domain of factor VII are potent inhibitors of TF-FVIIa mediated activation of FX (Husbyn et al., J. Peptide Res. (1997) 50:475–482). Several peptides corresponding to various regions of FVII (for example, amino acid sequence residues 372–337 and 103–112 of hFVII) have been proposed as therapeutic anticoagulants based upon their ability to inhibit TF-FVIIa mediated coagulation (International Publication No. WO 90/03390; International Publication No. WO95/00541). Active site modified FVII variants capable of binding TF have been proposed as pharmaceutical compositions for the prevention of TF/FVIIa mediated coagulation (International Publication No. WO 91/11514). International Publication No: WO 96/40779 describes peptide fragments of TF that inhibit FX activation. U.S. Pat. Nos. 5,759,954, 5,863,893, 5,880,256 and 5,834,244 describes variant Kunitz-type serine protease inhibitors that inhibit TF-FVIIa activity and have been shown to prolong tissue factor initiated prothrombin time (PT). This is consistent with the ability of these TF-FVIIa active site inhibitors to prevent FX activation through inhibition of the TF-FVIIa complex.

SUMMARY OF THE INVENTION

The present invention provides compounds and compositions which inhibit a FVII/FVIIa mediated or associated process such as the catalytic conversion of FVII to FVIIa, FIX to FIXa, or FX to FXa and thereby block initial events of the extrinsic pathway of blood coagulation. In addition, the compositions of the present invention are capable of neutralizing the thrombotic effects of endogenous TF by binding to FVII or FVIIa and preventing the TF-FVIIa mediated activation of FX. The compositions of the present invention are therefore useful in therapeutic and prophylactic methods for inhibiting TF-FVIIa mediated or associated processes. Advantageously, the compositions allow for a potent inhibition of FVIIa and the TF-FVIIa complex providing, in preferred embodiments, for low dose pharmaceutical formulations.

Accordingly, the invention provides compounds which, by virtue of binding FVII or FVIIa, inhibit a FVII or FVIIa mediated coagulation event. Such compounds preferably bind FVII or FVIIa with a Kd less than about 100 µM, preferably less than about 100 nM, and preferably do not substantially inhibit the activity of other proteases of the coagulation cascade. The compounds of the present invention can be, for example, peptides or peptide derivatives such as peptide mimetics. Specific examples of such compounds include linear or cyclic peptides and combinations thereof, preferably between about 10 and 100 amino acid residues in length, optionally modified at the N-terminus or C-terminus or both, as well as their salts and derivatives, functional analogues thereof and extended peptide chains carrying amino acids or polypeptides at the termini of the sequences for use in the inhibition of FVIIa mediated activation of FX.

The invention further provides a method for identifying a compound which blocks FVII/FVIIa mediated activation of FX comprising the steps of:

(1) contacting FVII/FVIIa with a peptide compound of the invention in the presence and absence of a candidate compound under conditions which allow specific binding of the peptide compound of the invention to FVII/FVIIa to occur;

(2) detecting the amount of specific binding of the peptide compound of the invention to FVII/FVIIa that occurs in the presence and absence of the candidate compound wherein a decrease in the amount of binding of the peptide compound in the presence of the candidate compound relative to the amount of binding in the absence of the candidate compound is indicative of the ability of the candidate compound to block FVII/FVIIa mediated activation of FX.

The invention further provides a peptide crystal including but not limited to the peptide crystal of TF76 (SEQ ID NO: 8) and their use in various methods described herein. According to one aspect, the invention provides a method of identifying peptidomimetics or peptide analogs of the peptides of the present invention comprising the step of screening a small molecule database with structural parameters derived from peptide crystals of the invention such as those described for TF76. Therefore, according to a particular aspect, the invention relates to the identification of compounds such as peptide analogs and peptidomimetics identified using the structural parameters of the peptide compounds provided herein.

The invention further provides a method of inhibiting the activation of FX to FXa comprising contacting FVII with TF under conditions which allow formation of a TF-FVIIa complex in the presence of a peptide compound of the invention (or, according to certain aspects, a compound that prevents the interaction of FVII/FVIIa with a peptide compound of the invention) and further contacting the TF-FVIIa complex with FX. According to this aspect of the invention, the contacting steps may occur in vivo or in vitro.

In particular aspects, the invention is directed to combinations of peptide compounds with other peptide compounds or with other proteins, especially serum proteins or peptides. The combinations are prepared with various objectives in mind, including; increasing the affinity or avidity of the peptide compound for FVII/FVIIa, as for example, by the use of various multimerization domains as described herein; increasing the stability of the peptide compound or facilitating its recovery and purification, as for example, by expressing the peptide compound as a Z protein fusion; and improving the therapeutic efficacy of the peptide compound in aspects of the invention involving in vivo use of the peptide compound, by for example, increasing or decreasing the serum half life, by for example, fusing the peptide compound to a plasma protein such as serum albumin, an immunoglobulin, apolipoproteins or transferrin (such fusion being made conveniently in recombinant host cells or by the use of bifunctional crosslinking agents).

The invention includes compositions, including pharmaceutical compositions, comprising compounds such as peptides for the treatment of a FVII/FVIIa mediated disorder as well as kits and articles of manufacture. Kits and articles of manufacture preferably include:

(a) a container;

(b) a label on or associated with said container; and (c) a composition comprising a compound of the present invention contained within said container; wherein the composition is effective for treating a FVII/FVIIa mediated disorder. Preferably, the label on said container indicates that the composition can be used for treating a FVII/FVIIa mediated disorder and the compound in said composition comprises a compound which binds FVII/FVIIa and prevents FVII/FVIIa mediated activation of FX. The kits optionally include accessory components such as a second container comprising a pharmaceutically-acceptable buffer and instructions for using the composition to treat a disorder.

Also disclosed are methods useful in the treatment of coagulopathic disorders, especially those characterized by the involvement of FVII/FVIIa or the TF-FVIIa complex. Therefore, the invention provides a method of treating a FVII/FVIIa or TF-FVIIa mediated disease or disorder in a host in need thereof comprising administering to the host a therapeutically effective amount of a compound of the invention. The methods are useful in preventing, blocking or inhibiting a FVII/FVIIa or TF-FVIIa associated event. In preferred embodiments, the methods of the present invention are employed to reduce or prevent the severity of or the degree of tissue injury associated with blood coagulation.

The present invention further provides various dosage forms of the compounds of the present invention, including but not limited to, those suitable for parenteral, oral, rectal and pulmonary administration of a compound. In preferred aspects of the present invention a therapeutic dosage form is provided suitable for inhalation and the invention provides for the therapeutic treatment of diseases or disorders involving a FVII/FVIIa mediated or associated process or event, such as the activation of FX, via pulmonary administration of a compound of the invention. More particularly, the invention is directed to pulmonary administration of the compounds of the invention, especially the peptide compounds, by inhalation. Thus, the present invention provides an aerosol formulation comprising an amount of a compound of the invention, more particularly a peptide compound of the invention, effective to block or prevent a FVII/FVIIa mediated or associated process or event and a dispersant. In one embodiment, the compound of the invention, particularly the peptide compound of the invention, can be provided in a liquid aerosol formulation. Alternatively, the compound can be provided as a dry powder aerosol formulation. Therefore, according to the present invention, formulations are provided which provide an effective noninvasive alternative to other parenteral routes of administration of the compounds of the present invention for the treatment of FVII/FVIIa or TF-FVIIa mediated or associated events.

BRIEF DESCRIPTION OF THE DRAWINGS

FIG. 2A shows the inhibition by various peptides of the TF dependent extrinsic clotting pathway as measured by the dose dependent prolongation of the prothrombin time (PT) in human plasma. FIG. 2B shows the results (no evidence for prolonging the clotting time) in the surface dependent intrinsic pathway as determined by the activated partial thromboplastin time (APTT) in human plasma.

FIG. 8A–FIG. 8D show the amino acid sequences of selected peptides and their IC50 values for inhibiting FX activation as well as the IC50 values for the inhibition of the binding of TF147b to either FVIIa or TF-FVIIa. "Ac—" denotes $CH_3CO$-modified N-terminus; "—$NH_2$" or "-amide" denotes $NH_2$ modified C-terminus; "Or" denotes ornithine; "Na" denotes .beta.-napthylalanine; "nL" denotes norleucine; "aca" denotes aminocaproic; "*" denotes the .epsilon. amino group of lysine as derivatized; "biotin", "bi" or "b" denotes biotin, "mY" denotes metatyrosine; "gla" denotes .gamma.-curboxyglutamic acid; "(X=i, i+8 lock)" denotes an i+8 helical lock; "X" denotes i) 4-methyl phenylalanine, ii) 4-amino phenylalanine, iii) 3-(3, 4-dihydroxyphenyl)alan- ine (DOPA); "X=E10-, K14lock" denotes a helical lock between side chain residues of glutamic acid and lysine in positions 10 and 14 respectively. Peptide name TF56 (SEQ ID NO: 1). TF58 (SEQ ID NO: 2); TF61 (SEQ ID NO: 3); TF62 (SEQ ID NO: 4); TF63 (SEQ ID NO: 5); TF74 (SEQ ID NO: 6); TF75 (SEQ ID NO: 7); TF76 (SEQ ID NO: 8); TF77 (SEQ ID NO: 9); TF86 (SEQ ID NO: 10); TF89 (SEQ ID NO: 11); TF90 (SEQ ID NO: 12); TF92 (SEQ ID NO: 13); TF95 (SEQ ID NO: 14); TF96 (SEQ ID NO: 15); TF97 (SEQ ID NO: 16); TF98 (SEQ ID NO: 17); TF106 (SEQ ID NO: 18); TF107 (SEQ ID NO: 19); TF108 (SEQ ID NO: 20); TF109 (SEQ ID NO: 21); TF110 (SEQ ID NO: 22); TF111 (SEQ ID NO: 23); TF112 (SEQ ID NO: 24); TF113 (SEQ ID NO: 25); TF114 (SEQ ID NO: 26); TF115 (SEQ ID NO: 27); TF119 (SEQ ID NO: 28); TF120 (SEQ ID NO: 29); TF121 (SEQ ID NO: 30); TF127 (SEQ ID NO: 31); TF128 (SEQ ID NO: 32); TF129 (SEQ ID NO: 33); TF130 (SEQ ID NO: 34); TF131 (SEQ ID NO: 35); TF132 (SEQ ID NO: 36); TF144 (SEQ ID NO: 37); TF145 (SEQ ID NO: 38); TF146 (SEQ ID NO: 39); TF147b (SEQ ID NO: 40); TF148 (SEQ ID NO: 41); TF149 (SEQ ID NO: 42); TF151 (SEQ ID NO: 43); TF152 (SEQ ID NO: 44); TF155 (SEQ ID NO: 45); TF156 (SEQ ID NO: 46); TF160 (SEQ ID NO: 47); TF161 (SEQ ID NO: 48); TF162 (SEQ ID NO: 49); TF163 (SEQ ID NO: 50); TF178 (SEQ ID NO: 51); TF179 (SEQ ID NO: 52); TF180 (SEQ ID NO: 53); TF189 (SEQ ID NO: 54); TF190 (SEQ ID NO: 55); TF191 (SEQ ID NO: 56); TF305 (SEQ ID NO: 57); TF306 (SEQ ID NO: 58); TF307 (SEQ ID NO: 59); TF316 (SEQ ID NO: 60); TF317 (SEQ ID NO: 61); TF318 (SEQ ID NO: 62); TF319 (SEQ ID NO: 63); TF320 (SEQ ID NO: 64); TF83 (SEQ ID NO: 109); TF84 (SEQ ID NO: 110); TF87 (SEQ ID NO: 111); TF88 (SEQ ID NO: 112); TF150 (SEQ ID NO: 113); TF192 (SEQ ID NO: 114); TF304 (SEQ ID NO: 115); TF312 (SEQ ID NO: 116); TF313 (SEQ ID NO: 117); TF315 (SEQ ID NO: 118); TF321 (SEQ ID NO: 119).

DETAILED DESCRIPTION OF THE PREFERRED EMBODIMENTS

Definitions

Figure 1:
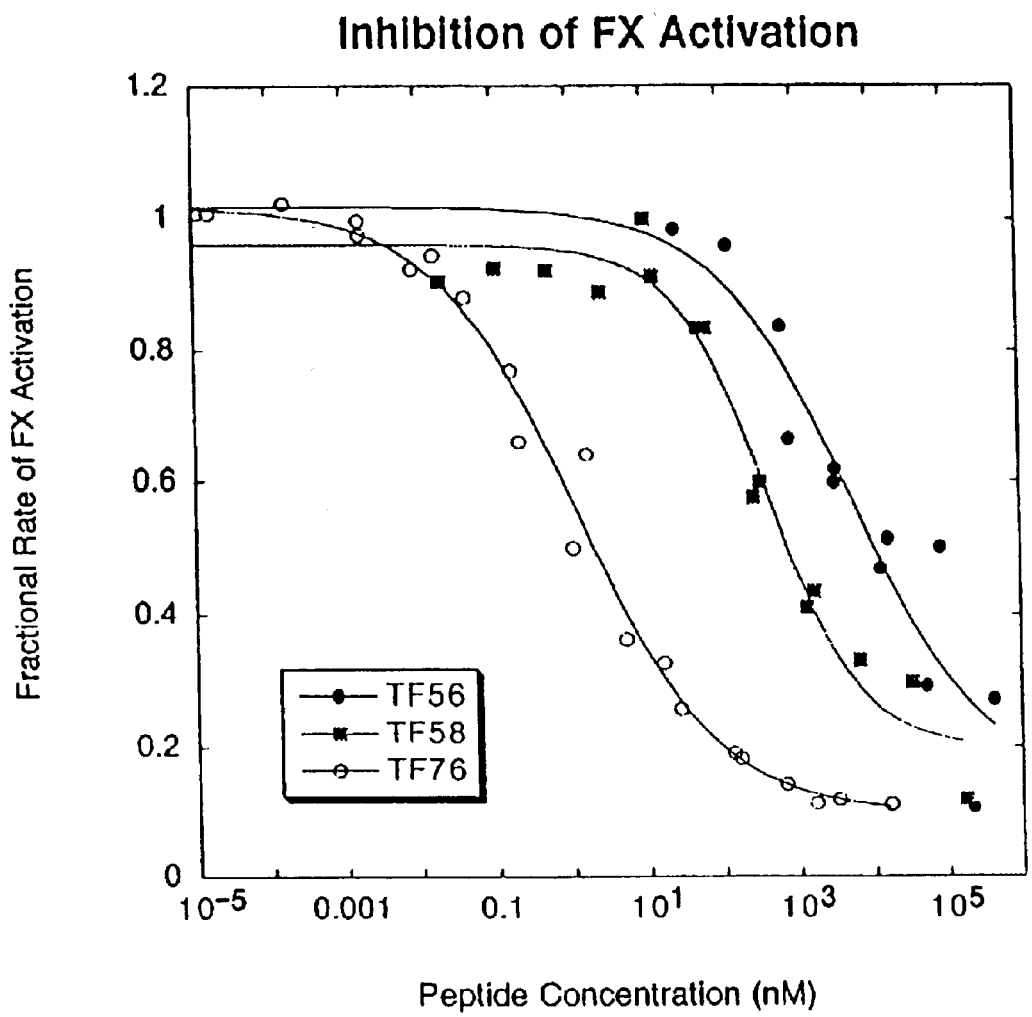
FIG. 1 shows the inhibition of FX activation by selected peptides.

Terms used in the claims and specification are defined as set forth below unless otherwise specified.

Abbreviations used throughout the description include: FIXa for Factor IXa and FIX for zymogen Factor IX; FXa for Factor Xa and FX for zymogen Factor X; FVII for zymogen factor VII; FVIIa for Factor VIIa; TF for tissue factor; TF-FVIIa for the tissue factor-Factor VIIa complex; FVII/FVIIa for FVII and/or FVIIa; sTF or $TF_{1-219}$ for soluble tissue factor composed of the extracellular domain amino acid residues 1–219; $TF_{1-243}$ for membrane tissue factor composed of the extracellular domain and transmembrane amino acid residues 1–243 (Paborsky et al., (1991) J. Biol. Chem. 266:21911–21916); PT for prothrombin time; APTT for activated partial thromboplastin time.

The expressions "agent" and "compound" are used within the scope of the present invention interchangeably and are meant to include any molecule or substance which blocks or prevents the interaction between FVII/FVIIa and a peptide compound of the present invention. Such molecules include small organic and bioorganic molecules, e.g. peptide mimetics and peptide analogs, antibodies, immunoadhesins, proteins, peptides, glycoproteins, glycopeptides, glycolipids, polysaccharides, oligosaccharides, nucleic acids, pharmacological agents and their metabolites, and the like. Preferred compounds of the present invention include peptide analogs or mimetics of the peptide compounds of the present invention. These include, for example, peptides containing non-naturally occurring amino acids provided the compound retains FVII/FVIIa inhibitory activity as described herein. Similarly, peptide mimetics and analogs may include non-amino acid chemical structures that mimic the structure of the peptide compounds of the present invention and retain the FVII/VIIa inhibitory activity described. Such compounds are characterized generally as exhibiting similar physical characteristics such as size, charge or hydrophobicity that is present in the appropriate spacial orientation as found in the peptide compound counterparts. A specific example of peptide mimetic compound is a compound in which the amide bond between one or more of the amino acids is replaced, for example, by a carbon-carbon bond or other bond as is well known in the art (see, for example Sawyer, in *Peptide Based Drug Design* pp. 378–422 (ACS, Washington D.C. 1995).

The term "peptide" is used herein to refer to constrained (that is, having some element of structure as, for example, the presence of amino acids which initiate a β turn or β pleated sheet, or for example, cyclized by the presence of disulfide bonded Cys residues) or unconstrained (e.g., linear) amino acid sequences of less than about 50 amino acid residues, and preferably less than about 40 amino acids residues, including multimers, such as dimers thereof or there between. Of the peptides of less than about 40 amino acid residues, preferred are the peptides of between about 10 and about 30 amino acid residues and especially the peptides of about 20 amino acid residues. However, upon reading the instant disclosure, the skilled artisan will recognize that it is not the length of a particular peptide but its ability to bind FVII/FVIIa and compete with the binding of a peptide compound described herein that distinguishes the peptide. Therefore, amino acid sequences of 5, 6, 7, 8, 9, 10, 11, 12, 13, 14, 15, 16, 17, 18, 19, 20, 21, 22, 23, 24 and 25 amino acid residues, for example, are equally likely to be compounds within the context of the present invention.

The term "amino acid" within the scope of the present invention is used in its broadest sense and is meant to include the naturally occurring L α-amino acids or residues. The commonly used one and three letter abbreviations for naturally occurring amino acids are used herein (Lehninger, A. L., Biochemistry, 2d ed., pp. 71–92, (1975), Worth Publishers, New York). The term includes D-amino acids as well as chemically modified amino acids such as amino acid analogs, naturally occurring amino acids that are not usually incorporated into proteins such as norleucine, and chemically synthesized compounds having properties known in the art to be characteristic of an amino acid. For example, analogs or mimetics of phenylalanine or proline, which allow the same conformational restriction of the peptide compounds as natural Phe or Pro are included within the definition of amino acid. Such analogs and mimetics are referred to herein as "functional equivalents" of an amino acid. Other examples of amino acids are listed by Roberts and Vellaccio (*The Peptides: Analysis, Synthesis, Biology,*) Eds. Gross and Meiehofer, Vol. 5 p 341, Academic Press, Inc, N.Y. 1983, which is incorporated herein by reference.

The term "conservative" amino acid substitution as used within this invention is meant to refer to amino acid substitutions which substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. The largest sets of conservative amino acid substitutions include:
(1) hydrophobic: His, Trp, Tyr, Phe, Met, Leu, Ile, Val, Ala;
(2) neutral hydrophilic: Cys, Ser, Thr;
(3) polar: Ser, Thr, Asn, Gln;
(4) acidic/negatively charged: Asp, Glu;
(5) charged: Asp, Glu, Arg, Lys, His;
(6) positively charged: Arg, Lys, His;
(7) basic: His, Lys, Arg;
(8) residues that influence chain orientation: Gly, Pro; and
(9) aromatic: Trp, Tyr, Phe, His.

In addition, structurally similar amino acids can substitute conservatively for some of the specific amino acids. Groups of structurally similar amino acids include: (Ile, Leu, and Val); (Phe and Tyr); (Lys and Arg); (Gln and Asn); (Asp and Glu); and (Gly and Ala). In this regard, it is understood that amino acids are substituted on the basis of side chain bulk, charge and/or hydrophobicity.

Amino acid residues can be further classified as cyclic or noncyclic, aromatic or non aromatic with respect to their side chain groups these designations being commonplace to the skilled artisan.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Arg |
| Ile | Leu, Val, Met, Ala Phe | Leu |
| Leu | Ile, Val Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe Ala | Leu |

Peptides synthesized by the standard solid phase synthesis techniques described here, for example, are not limited to amino acids encoded by genes for substitutions involving the amino acids. Commonly encountered amino acids which are not encoded by the genetic code, include, for example, those described in International Publication No. WO 90/01940 and described in Table I below, as well as, for example, 2-amino adipic acid (Aad) for Glu and Asp; 2-aminopimelic acid (Apm) for Glu and Asp; 2-aminobutyric (Abu) acid for Met, Leu, and other aliphatic amino acids; 2-aminoheptanoic acid (Ahe) for Met, Leu and other aliphatic amino acids; 2-aminoisobutyric acid (Aib) for Gly; cyclohexylalanine (Cha) for Val, and Leu and Ile; homoarginine (Har) for Arg and Lys; 2,3-diaminopropionic acid (Dpr) for Lys, Arg and His; N-ethylglycine (EtGly) for Gly, Pro, and Ala; N-ethylglycine (EtGly) for Gly, Pro, and Ala; N-ethylasparigine (EtAsn) for Asn, and Gln; Hydroxy-llysine (Hyl) for Lys; allohydroxyllysine (AHyl) for Lys; 3-(and 4)hydroxyproline (3Hyp, 4Hyp) for Pro, Ser, and Thr; allo-isoleucine (AIle) for Ile, Leu, and Val; p-amidinophenylalanine for Ala; N-methylglycine (MeGly, sarcosine) for Gly, Pro, and Ala; N-methylisoleucine (MeIle) for Ile; Norvaline (Nva) for Met and other aliphatic amino acids; Norleucine (Nle) for Met and other aliphatic amino acids; Ornithine (Orn or Or) for Lys, Arg and His; Citrulline (Cit) and methionine sulfoxide (MSO) for Thr, Asn and Gln; -methylphenylalanine (MePhe), trimethylphenylalanine, halo (F, Cl, Br, and I)phenylalanine, triflourylphenylalanine, for Phe.

TABLE 1

Abbreviations used in the specification

| Compound | Abbreviation | |
|---|---|---|
| Acetyl | Ac | |
| Alanine | Ala | A |
| 3-(2-Thiazolyl)-L-alanine | Tza | |
| Arginine | Arg | R |
| Asparagine | Asn | N |
| Aspartic acid | Asp | D |
| t-Butyloxycarbonyl | Boc | |
| Benzotriazol-1-yloxy-tris-(dimethylamino)-phosphonium-hexafluorophosphate | Bop | |
| β-Alanine | βAla | |
| β-Valine | βVal | |
| β-(2-Pyridyl)-alanine | Pal (2) | |
| β-(3-Pyridyl)-alanine | Pal (3) | |
| β-(4-Pyridyl)-alanine | Pal (4) | |
| β-(3-N-Methylpyridinium)-alanine | PalMe (3) | |
| t-Butyl | tBu, But | |
| t-Butyloxycarbonyl | Boc | |
| Caffeic acid | Caff | |
| Cysteine | Cys | C |
| Cyclohexylalanine | Cha | |
| Cyclohexylglycine | Chg | |
| 3,5-Dinitrotyrosine | Tyr(3,5-No$_2$) | |
| 3,5-Diiodotyrosine | Tyr(3,5-I) | |

TABLE 1-continued

Abbreviations used in the specification

| Compound | Abbreviation | |
|---|---|---|
| 3,5-Dibromotyrosine | Tyr(3,5-Br) | |
| 9-Fluorenylmethyloxy-carbonyl | Fmoc | |
| Glutamine | Gln | Q |
| Glutamic acid | Glu | E |
| γ-Carboxyglutamic acid | Gla | |
| Glycine | Gly | G |
| Histidine | His | H |
| Homoarginine | hArg | |
| 3-Hydroxyproline | Hyp | |
| Isoleucine | Ile | I |
| Leucine | Leu | L |
| tert-Leucine | Tle | |
| Lysine | Lys | K |
| Mercapto-β,β-cyclopentamethylene-propionic acid | Mpp | |
| Mercaptoacetic acid | Mpa | |
| Mercaptopropionic acid | Mpr | |
| Methionine | Met | M |
| β-Naphthylalanine | Na | |
| Nicotinic acid | Nic | |
| Nipecotic acid | Npa | |
| N-methyl nicotinic acid | NicMe | |
| Norarginine | nArg | |
| Norleucine | Nle nL | |
| Norvaline | Nva | |
| Ornithine | Orn or Or | |
| Ornithine-derived dimethylamidinium | Orn(N$^\delta$-C$_3$H$_7$N) | |
| Phenylalanine | Phe | F |
| p-Guanidinophenylalanine | Phe(Gua) | |
| p-Aminophenylalanine | Phe(NH$_2$) | |
| p-Chlorophenylalanine | Phe(Cl) | |
| p-Flurophenylalanine | Phe(F) | |
| p-Nitrophenylalanine | Phe(NO$_2$) | |
| p-Hydroxyphenylglycine | Pgl(OH) | |
| p-Toluenesulfonyl | Tos | |
| m-Amidinophenylalanine | mAph | |
| p-Amidinophenylalanine | pAph | |
| Phenylglycine | Pgl | |
| Phenylmalonic acid | Pma | |
| Proline | Pro | P |
| 4-Quinolinecarboxy | 4-Qca | |
| Sarcosine | Sar | |
| Serine | Ser | S |
| Succinyl | Suc | |
| Threonine | Thr | T |
| Tryptophan | Trp | W |
| Tyrosine | Tyr | Y |
| 3-iodotyrosine | Tyr(3-I) | |
| O-Methyl tyrosine | Tyr(Me) | |
| Valine | Val | V |

* Amino acids of D configuration are denoted by D-prefix using three-letter code (eg., D-Ala, D-Cys, D-Asp, D-Trp).

A useful method for identification of certain residues or regions of the compound for amino acid substitution other than those described herein is called alanine scanning mutagenesis as described by Cunningham and Wells (1989) Science, 244:1081–1085. Here a residue or group of target residues are identified (e.g. charged residues such as Arg, Asp, His, Lys, and Glu) and replaced by a neutral or negatively charged amino acid to affect the interaction of the amino acids with the surrounding aqueous environment in or outside the cell. Those regions demonstrating functional sensitivity to the substitution are then refined by introducing further or other variations at or for the sites of substitution. Thus while the site for introducing an amino acid sequence variation is predetermined the nature of the mutation per se need not be predetermined. For example, to optimize the performance of a mutation at a given site, Ala scanning or random mutagenesis may be conducted at the target codon or region and the expressed compound screened for the optimal combination of desired activity.

Phage display of protein or peptide libraries offers another methodology for the selection of compounds with improved affinity, altered specificity, or improved stability (Smith, G. P., (1991) Curr. Opin. Biotechnol. 2:668–673; Lowman, (1997) Ann. Rev. Biophys. Biomol. Struct. 26:401–404). High affinity proteins, displayed in a monovalent fashion as fusions with the M13 gene III coat protein (Clackson, T., (1994) et al., Trends Biotechnol. 12:173–183), can be identified by cloning and sequencing the corresponding DNA packaged in the phagemid particles after a number of rounds of binding selection.

Other compounds include the fusion to the—or C-terminus of the compounds described herein of immunogenic polypeptides, e.g., bacterial polypeptides such as beta lactamase or an enzyme encoded by *E coli* Trp locus or yeast protein, other polypeptides such as the Z-domain of protein-A, and C-terminal fusion with proteins having a long half-life such as immunoglobulin constant region or other immunoglobulin regions, albumin, or ferritin as described in WO 89/02922 published 6 Apr 1989. Further, free functional groups on the side chains of the amino acid residues can also be modified by amidation, acylation or other substitution, which can, for example, change the solubility of the compounds without affecting their activity. "Ac—" for example denotes a $CH_3CO$— modified N terminus and "—NH2" a —$NH_2$ modified C-terminus.

Preferred amino acid sequences within the context of the present invention are non-naturally occurring amino acid sequences. By non-naturally occurring is meant that the amino acid sequence is not found in nature. Preferred are non-naturally occuring amino acid sequences of between about 10 and 30 amino acid residues and preferably about 20 amino acid residues. These include peptides, peptide analogs and mimetics containing naturally as well as non-naturally occurring amino acids. Especially preferred are sequences as described above consisting of naturally occurring amino acids.

The term "multimerization domain" as used in particular aspects of the present invention, is meant to refer to the portion of the molecule to which the compound, especially the peptide compound, is joined, either directly or through a "linker domain." The multimerization domain is an amino acid domain which, according to preferred embodiments, facilitates the interaction of two or more multimerization domains. While the multimerization domain promotes the interaction between two or more multimerization domains, there is no requirement within the context of the present invention that the peptide joined to a multimerization domain be present as a portion of a multimer.

According to preferred aspects of the present invention the multimerization domain is a polypeptide which promotes the stable interaction of two or more multimerization domains. By way of example and not limitation, a multimerization domain may be an immunoglobulin sequence, such as an immunoglobulin constant region, a leucine zipper, a hydrophobic region, a hydrophilic region, a polypeptide comprising a free thiol which forms an intermolecular disulfide bond between two or more multimerization domains or, for example a "protuberance-into-cavity" domain described in U.S. Pat. No. 5,731,168. In that patent, protuberances are constructed by replacing small amino acid side chains from the interface of a first polypeptide with a larger side chain (for example a tyrosine or tryptophan). Compensatory cavities of identical or similar size to the protuberances are optionally created on the interface of a second polypeptide by replacing large amino acid side chains with smaller ones (for example alanine or threonine).

Therefore, in a preferred aspect, the multimerization domain provides that portion of the molecule which promotes or allows stable interaction of two or more multimerization domains and promotes or allows the formation of dimers and other multimers from monomeric multimerization domains. Preferably, according to this aspect of the invention, multimerization domains are immunoglobulin constant region domains. Immunoglobulin constant domains provide the advantage of improving in vivo circulating half-life of the compounds of the invention and optionally allow the skilled artisan to incorporate an "effector function" as described herein below into certain aspects of the invention.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), expressly incorporated herein by reference. The "EU index as in Kabat" refers to the residue numbering of the human IgG1 EU antibody.

"Antibodies" (Abs) and "immunoglobulins" (Igs) are typically glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Antibodies" and "immunoglobulins" are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has an amino (N) terminal variable domain (VH) followed by carboxy (C) terminal constant domains. Each light chain has a variable N-terminal domain (VL) and a C-terminal constant domain; the constant domain of the light chain (CL) is aligned with the first constant domain (CH1) of the heavy chain, and the light chain variable domain is aligned with the variable domain of the heavy chain. According to the domain definition of immunoglobulin polypeptide chains, light (L) chains have two conformationally similar domains VL and CL; and heavy chains have four domains (VH, CH1, CH2, and CH3) each of which has one intrachain disulfide bridge.

Depending on the amino acid sequence of the constant (C) domain of the heavy chains, immunoglobulins can be assigned to different classes. There are five major classes of immunoglobulins: IgA, IgD, IgE, IgG, and IgM. The immunoglobulin class can be further divided into subclasses (isotypes), e.g., $IgG_1$, $IgG_2$, $IgG_3$, $IgG_4$, $IgA_1$, and $IgA_2$. The heavy-chain constant domains that correspond to the different classes of immunoglobulins are α, δ, ε, γ, and μ domains respectively. The light chains of antibodies from any vertebrate species can be assigned to one of two distinct types called kappa (κ) or lambda (λ), based upon the amino acid sequence of their constant domains. Sequence studies have shown that the μ chain of IgM contains five domains VH, CHμ1, CHμ2, CHμ3, and CHμ4. The heavy chain of IgE (ε) also contains five domains.

The subunit structures and three-dimensional configurations of different classes of immunoglobulins are well known. Of these IgA and IgM are polymeric and each subunit contains two light and two heavy chains. The heavy chain of IgG (γ) contains a length of polypeptide chain lying between the CHγ1 and CHγ2 domains known as the hinge region. The α chain of IgA has a hinge region containing an O-linked glycosylation site and the μ and ε chains do not have a sequence analogous to the hinge region of the γ and α chains, however, they contain a fourth constant domain lacking in the others. The domain composition of immunoglobulin chains can be summarized as follows:

Light Chain λ=Vλ Cλ
  κ=Vκ Cκ
Heavy Chain IgG (γ)=VH CHγ1, hinge CHγ2 CHγ3
  IgM (μ)=VH CHμ1 CHμ2 CHμ3 CHμ4
  IgA (α)=VH CHα1 hinge CHα2 CHα3
  IgE (ε)=VH CHε1 CHε2 CHε3 CHε4
  IgD (δ)=VH CHδ1 hinge CHδ2 CHδ3

The "CH2 domain" of a human IgG Fc region (also referred to as "Cγ2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule.

The "CH3 domain" comprises the stretch of residues C-terminal to a CH2 domain in an Fc region (i.e. from about amino acid residue 341 to about amino acid residue 447 of an IgG).

"Hinge region" is generally defined as stretching from Glu216 to Pro230 of human IgG1 (Burton, *Molec. Immunol.*22:161–206 (1985)). Hinge regions of other IgG isotypes may be aligned with the IgG1 sequence by placing the first and last cysteine residues forming inter-heavy chain S—S bonds in the same positions.

The "lower hinge region" of an Fc region is normally defined as the stretch of residues immediately C-terminal to the hinge region, i.e. residues 233 to 239 of the Fc region.

A TF-FVIIa mediated or associated process or event, or equivalently, an activity associated with plasma FVII/FVIIa, according to the present invention is any event which requires the presence of FVIIa. The general mechanism of blood clot formation is reviewed by Ganong, in Review of Medical Physiology, 13th ed., Lange, Los Altos Calif., pp411–414 (1987). Coagulation requires the confluence of two processes, the production of thrombin which induces platelet aggregation and the formation of fibrin which renders the platelet plug stable. The process comprises several stages each requiring the presence of discrete proenzymes and procofactors. The process ends in fibrin crosslinking and thrombus formation. Fibrinogen is converted to fibrin by the action of thrombin. Thrombin, in turn, is formed by the proteolytic cleavage of prothrombin. This proteolysis is effected by FXa which binds to the surface of activated platelets and in the presence of FVa and calcium, cleaves prothrombin. TF-FVIIa is required for the proteolytic activation of FX by the extrinsic pathway of coagulation. Therefore, a process mediated by or associated with TF-FVIIa, or an activity associated with FVII/FVIIa includes any step in the coagulation cascade from the formation of the TF-FVIIa complex to the formation of a fibrin platelet clot and which initially requires the presence FVII/FVIIa. For example, the TF-FVIIa complex initiates the extrinsic pathway by activation of FX to FXa, FIX to FIXa, and additional FVII to FVIIa.

TF-FVIIa mediated or associated process, or FVII/FVIIa mediated or associated activity, can be conveniently measured employing standard assays such as those described in Roy, S., (1991) J. Biol. Chem. 266:4665–4668, O'Brien, D., et al., (1988) J. Clin. Invest. 82:206–212; Lee et al. (1997) Biochemistry 36:5607–5611; Kelly et al., (1997) J. Biol. Chem. 272:17467–17472 for the conversion of chromogenic substrates or Factor X to Factor Xa in the presence of Factor VII and other necessary reagents.

A TF-FVIIa related disease or disorder is meant to include chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, acute and chronic indications such as inflammation, septic shock, septicemia, hypotension, adult respiratory distress syndrome (ARDS), disseminated intravascular coagulapathy (DIC) and other diseases. The TF-FVIIa related disorder is not limited to in vivo coagulopathic disorders such as those named above but includes inappropriate or undesirable coagulation related to circulation of blood through stents or artificial valves or related to extracorporeal circulation including blood removed in-line from a patient in such processes as dialysis procedures, blood filtration, or blood bypass during surgery.

As used herein, the term "pulmonary administration" refers to administration of a formulation of the invention through the lungs by inhalation. As used herein, the term "inhalation" refers to intake of air to the alveoli. In specific examples, intake can occur by self-administration of a formulation of the invention while inhaling, or by administration via a respirator, e.g., to a patient on a respirator. The term "inhalation" used with respect to a formulation of the invention is synonymous with "pulmonary administration."

As used herein, the term "parenteral" refers to introduction of a compound of the invention into the body by other than the intestines, and in particular, intravenous (i.v.), intraarterial (i.a.), intraperitoneal (i.p.), intramuscular (i.m.), intraventricular, and subcutaneous (s.c.) routes.

As used herein, the term "aerosol" refers to suspension in the air. In particular, aerosol refers to the particlization of a formulation of the invention and its suspension in the air. According to the present invention, an aerosol formulation is a formulation comprising a compound of the present invention that is suitable for aerosolization, i.e., particlization and suspension in the air, for inhalation or pulmonary administration.

The term "treatment" as used within the context of the present invention is meant to include therapeutic treatment as well as prophylactic, or suppressive measures for the disease or disorder. Thus, for example, the term treatment includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease. Further, administration of the agent after onset and after clinical symptoms have developed where administration affects clinical parameters of the disease or disorder, such as the degree of tissue injury or the amount or extent of leukocyte trafficking and perhaps amelioration of the disease, comprises "treatment" of the disease.

Those "in need of treatment" include mammals, such as humans, already having the disease or disorder, including those in which the disease or disorder is to be prevented.

The term "acyl" is used in its broadest sense to mean saturated or unsaturated, linear, branched or cyclic chains of about 1 to about 16 carbon atoms, which contain a carboxy group. Thus the term acyl includes, for example, groups such as formyl, acetyl, benzoyl and the like. The term "hydrophobic acyl" group refers to a R1-C(=O)— group wherein R1 is an alkyl, aryl or other non-polar group.

MODES FOR CARRYING OUT THE INVENTION

Selection of Compounds

The present invention provides compounds and compositions which inhibit a FVII/FVIIa mediated or associated process such as the catalytic conversion of FVII to FVIIa, FIX to FIXa, or FX to FXa and thereby block initial events of the extrinsic pathway of blood coagulation. Preferred compounds of the present invention are distinguished by their ability compete with a peptide compound of FIG. 8 for binding FVII/FVIIa and may be selected as follows.

For in vitro assay systems to determine whether a compound has the "ability" to compete with a peptide compound as noted above, the skilled artisan can employ any of a number of standard competition assays. Such procedures include but are not limited to competitive assay systems using techniques such as radioimmunoassays, enzyme immunoassays (EIA), preferably the enzyme linked immunosorbent assay (ELISA), "sandwich" immunoassays, immunoradiometric assays, fluorescent immunoassays, and immunoelectrophoresis assays, to name but a few.

Figure 8C:
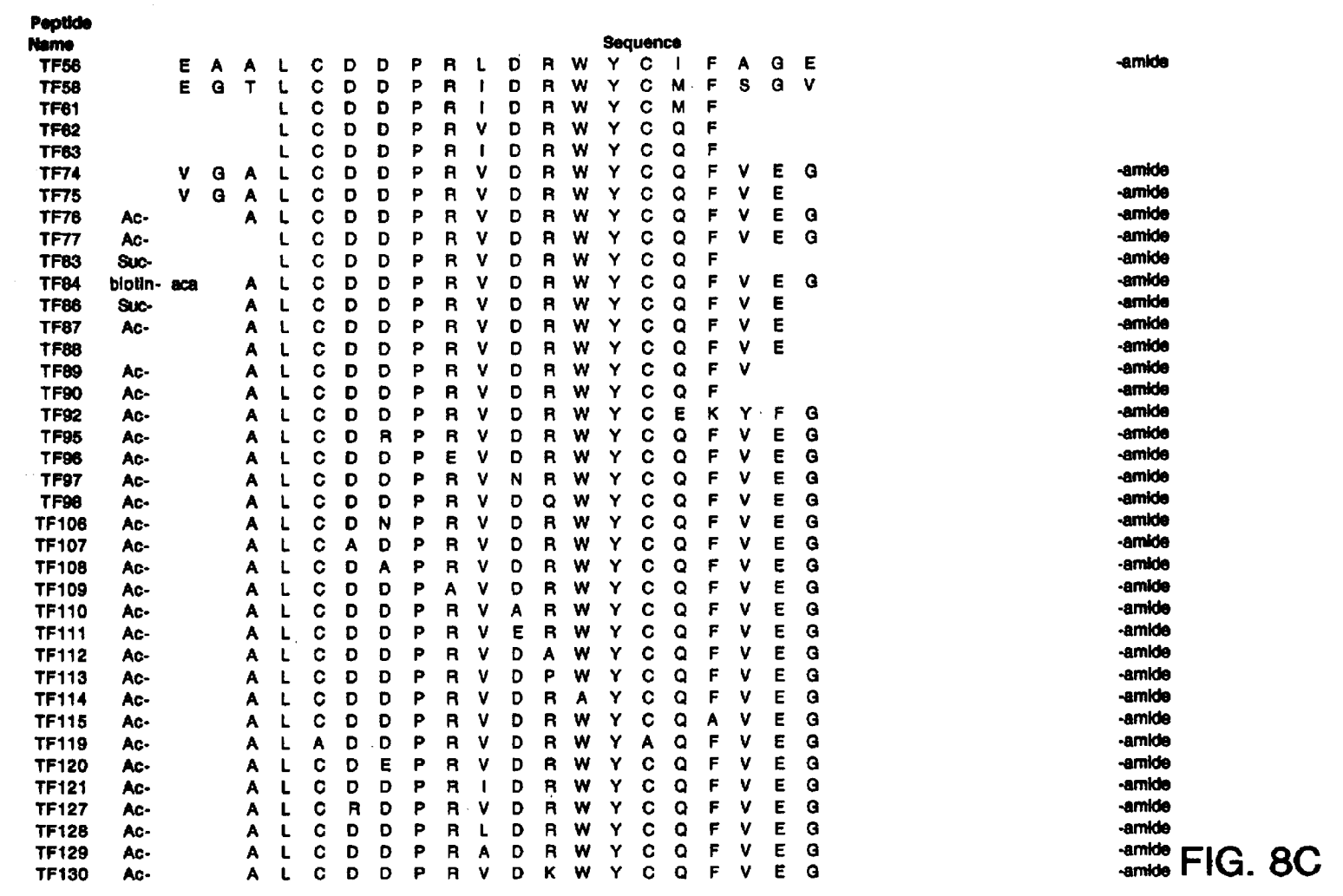
Figure 8D:
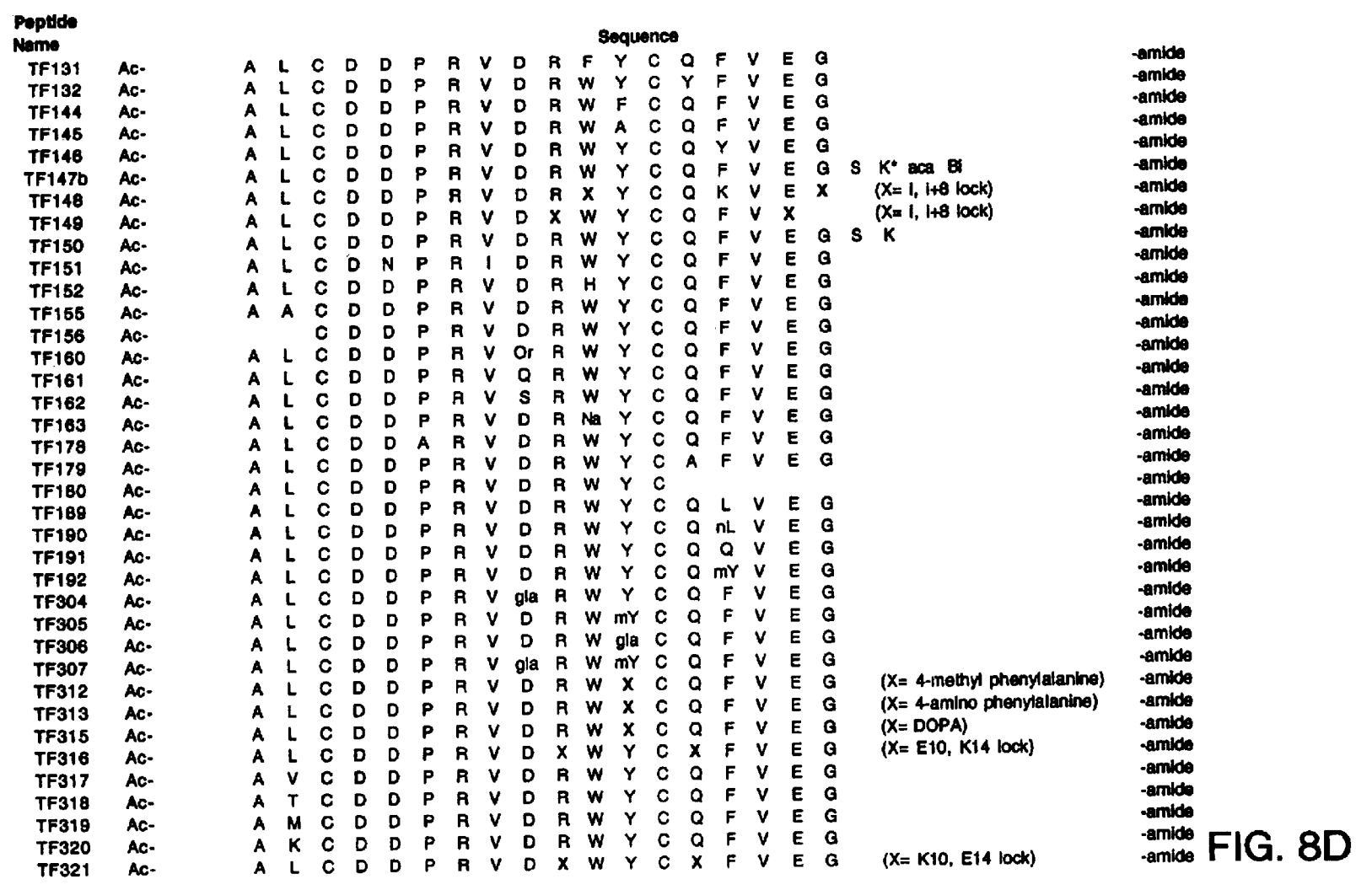

For these purposes the selected peptide compound of FIG. 8 will be labeled with a detectable moiety (the detectably labeled peptide compound herein called the "tracer") and used in a competition assay with a candidate compound for binding FVII/FVIIa. Numerous detectable labels are available which can be preferably grouped into the following categories:

(a) Radioisotopes, such as $^{35}S$, $^{14}C$, $^{125}I$, $^{3}H$, and $^{131}I$. The peptide compound can be labeled with the radioisotope using the techniques described in *Current Protocols in Immunology*, Volumes 1 and 2, Coligen et al., Ed., Wiley-Interscience, New York, N.Y., Pubs., (1991) for example and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the peptide compounds using the techniques disclosed in *Current Protocols in Immunology*, supra, for example. Fluorescence can be quantified using a fluorimeter.

(c) Various enzyme-substrate labels are available and U.S. Pat. No. 4,275,149 provides a review of some of these. The enzyme preferably catalyses a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like.

Examples of enzyme-substrate combinations include, for example:

(i) Horseradish peroxidase (HRP) with hydrogen peroxidase as a substrate, wherein the hydrogen peroxidase oxidizes a dye precursor (e.g. ABTS, orthophenylene diamine (OPD) or 3,3',5,5'-tetramethyl benzidine hydrochloride (TMB));

(ii) alkaline phosphatase (AP) with para-Nitrophenyl phosphate as chromogenic substrate; and (iii) β-D-galactosidase (β-D-Gal) with a chromogenic substrate (e.g. p-nitrophenyl-β-D-galactosidase) or fluorogenic substrate 4-methylumbelliferyl-β-D-galactosidase.

According to a particular assay, the tracer is incubated with immobilized FVII/FVIIa in varying concentration of unlabeled candidate compound. Increasing concentrations of successful candidate compound effectively compete with binding of the tracer to immobilized FVII/FVIIa. The concentration of unlabeled candidate compound at which 50% maximal tracer is displaced is referred to as the $IC_{50}$ and reflects the FVII/FVIIa binding affinity of the candidate compound. Therefore a candidate compound with an $IC_{50}$ of 1 mM displays a substantially weaker interaction with FVII/FVIIa than a candidate peptide with an $IC_{50}$ of 1 μM.

Accordingly, the invention provides compound "having the ability to compete" for binding FVII/FVIIa in an in vitro assay as described. Preferably the compound has an "$IC_{50}$" for FVIIa of less than 1 μM. Preferred among these compound are compounds having an $IC_{50}$ of less than about 100 nM and preferably less than about 10 nM or less than about 1 nM. In further preferred embodiments according to this aspect of the invention the compounds display an $IC_{50}$ for FVIIa of less than about 100 pM and more preferably less than about 10 pM.

A preferred in vitro assay for the determination of a candidate compound's ability to compete with a peptide compound of FIG. 8 is as follows and is described more fully in Examples 1 and 2. The ability of peptides to compete with tracer for binding to FVIIa is monitored using an ELISA. Dilutions of candidate peptide in buffer are added to microtiter plates coated with TF-FVIIa (as described in the Example Sections) along with tracer for 1 hr. The microtiter plate is washed with wash buffer and the amount of tracer bound to FVIIa measured.

In particular embodiments the tracer is SEQ ID NO: 1 and is added to the FVII/FVIIa coated plated at a concentration of 10 μM. In another preferred embodiment the tracer is SEQ ID NO: 8 and is added to the FVII/FVIIa coated plate at a concentration of 20 nM.

Compounds selected in this way are then tested for their ability to inhibit or block FVII/FVIIa activation of FX. The term "inhibits" or "blocks" when used to describe a characteristic of the candidate compound of the present invention means a compound that when added at a concentration of about 10 μM in a standard chromogenic assay for FX activation (see, Roy, S., (1991) J. Biol. Chem. 266:4665–4668, O'Brien, D., et al., (1988) J. Clin. Invest. 82:206–212; Lee et al. (1997) Biochemistry 36:5607–5611; Kelly et al., (1997) J. Biol. Chem. 272:17467–17472) produces at least a 50% inhibition of the conversion of Factor X to Factor Xa in the presence of Factor VII and other necessary reagents. Preferably the compound will produce at least a 50% inhibition at a concentration of about 1 μM and more preferably at least a 50% inhibition at a concentration of about 100 nM. In a more preferred embodiment the compound of the present invention will produce at least a 50% inhibition of the conversion of Factor X to Factor Xa when present in a concentration of about 10 nM or less.

Peptides and Analogs Thereof

According to preferred aspects of the present invention the compound is a cyclic peptide or analog thereof. Preferably, the compound has the following formula:

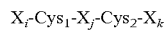

wherein $X_i$ is absent or is a peptide of between 1 and 100 amino acids, preferably between about 1 and 50 amino acids, and more preferably between about 1 and 10 or about 1 and 4 amino acids; $X_j$ is 9 amino acid peptide and $X_k$ is absent or a peptide of between 1 and 100 amino acids, preferably between about 1 and 50 amino acids and more preferably between about 1 and 10 or about 1 and 4 amino acids, so long as the cyclic peptide or analog thereof retains the qualitative biological activity described above.

Preferred among this group of compounds are compounds comprising the sequence:

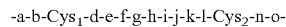

wherein a is an amino acid; b is an amino acid selected from the group consisting of Leu, Ile, Val, Ala, Arg, Gln, Asn and functional equivalents thereof; d is an amino acid; e is an amino acid; f is an amino acid selected from the group consisting of Ala, Asp, Glu, Phe, Gly, His, Ile, Lys, Leu, Met, Asn, Pro, Gln, Arg, Ser, Thr, Val, Trp, Tyr and functional equivalents thereof; g is an amino acid; h is an amino acid selected from the group consisting of Ala, Cys, Asp, Phe, Gly, His, Ile, Lys, Leu, Met, Asn, Pro, Gln, Arg, Thr, Val, Trp, Tyr and functional equivalents thereof; i is an amino acid selected from the group consisting of Ala, Asp, Glu, Phe, Gly, His, Lys, Met, Asn, Pro, Gln, Ser, Thr, Val, Trp, Tyr and functional equivalents thereof; j is an amino acid selected from the group consisting of Ala, Asp, Glu, Phe, Gly, His, Ile, Lys, Leu, Met, Asn, Pro, Gln, Arg, Ser, Thr, Val, Trp, Tyr and functional equivalents thereof; k is an amino acid selected from the group consisting of Trp, Tyr, Na, Phe and functional equivalents thereof; l is an amino acid selected from the group consisting of Tyr, Phe, Na, Trp and functional equivalents thereof; n is an amino acid and o is an amino acid selected from the group consisting of Phe Tyr, Trp, Na and functional equivalents thereof.

Preferred among this class of compounds are those described above wherein $X_i$ is a peptide of between 2 and 10 or 2 and 4 amino acids and $X_k$ is a peptide of between 2 and 10 or 2 and 4 amino acids. For example, preferred compounds are those described above wherein b is an amino acid selected from the group consisting of Leu, Ile, Val, Ala and functional equivalents thereof and preferably Leu, Ile, Val and functional equivalents thereof; f is any amino acid except Cys and preferable selected from the group consisting of Pro, Gly, Ala and functional equivalents thereof; h is an amino acid selected from the group consisting of Ile, Val, Leu and Ala and functional equivalents thereof; i is an amino acid selected from the group consisting of Asp, Glu, Ser, Thr and Ala and functional equivalents thereof; j is any amino acid except Cys and preferably any amino acid except Cys and Trp; k is an amino acid selected from the group consisting of Tyr, Phe, Trp, Na and functional equivalents thereof and preferably Trp and Na and functional equivalents thereof; l is an amino acid selected from the group consisting of Trp, Phe, Tyr, Phe and functional equivalents thereof and preferably Tyr, Na and functional equivalents thereof; o is an amino acid selected from the group consisting of Trp, Phe, Tyr and functional equivalents thereof.

Preferred among this class of cyclic peptide compounds or analogs thereof are those wherein h is an amino acid selected from the group consisting of Ile, Val and Leu and functional equivalents thereof; i is an amino acid selected from the group consisting of Asp, Glu, and Ser and functional equivalents thereof; j is an amino acid selected from the group consisting of Arg, Lys, Gln and Ala and functional equivalents thereof; and n is an amino acid selected from the group consisting of Gln, Met, Gly, Arg, Ser, Lys, Leu, Ala, Asn, Thr and functional equivalents thereof.

Preferred among this group of compounds are compounds wherein h is an amino acid selected from the group consisting of Ile and Val and functional equivalents thereof; i is Asp and functional equivalents thereof; j is Arg and functional equivalents thereof; l is Tyr and functional equivalents thereof; n is an amino acid selected from the group consisting of Gln and Met and functional equivalents thereof and o is Phe and functional equivalents thereof.

Preferred among this group are cyclic peptide compounds or analogs thereof wherein a is an amino acid selected from the group consisting of Asn, Arg, Phe, Gln, Gly, Pro, Thr, Ser and Ala and functional equivalents thereof; f is an amino acid selected from the group consisting of Pro, Gly, Ala and functional equivalents thereof.

Preferred among this class of compounds are compounds wherein $X_i$ is a peptide of between 2 to 6 amino acids; a is an amino acid selected from the group consisting of Ala, Thr and Ser and functional equivalents thereof; b is Leu and functional equivalents thereof; d is an amino acid selected from the group consisting of Asp, Glu, Ser, Ala, Arg, Thr, His, Met, Val and Asn and functional equivalents thereof; e is an amino acid selected from the group consisting of Asn, Asp, Arg, Ala and Glu and functional equivalents thereof; f is Pro and functional equivalents thereof; g is an amino acid selected from the group consisting of Arg, Ala and Glu and functional equivalents thereof; h is an amino acid selected from the group consisting of Ile, Val and Leu and functional equivalents thereof; i is an amino acid selected from the group consisting of Asp, Glu and Ser; j is an amino acid selected from the group consisting of Arg, Lys, Gln and Ala and functional equivalents thereof; n is an amino acid selected from the group consisting of Gln, Met, Gly, Arg, Ser, Lys, Leu, Ala, Asn and Thr and functional equivalents thereof and $X_k$ is a peptide of between 2 and 6 amino acids.

Preferred among this group of compounds are cyclic peptides or analogs thereof having the following formula

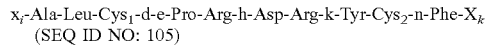
$x_i$-Ala-Leu-Cys$_1$-d-e-Pro-Arg-h-Asp-Arg-k-Tyr-Cys$_2$-n-Phe-$X_k$
(SEQ ID NO: 105)

wherein $X_i$ is absent or is a peptide of between 1 to 4 amino acids; d is an amino acid selected from the group consisting of Asp, Glu, Ser, Ala and Arg and functional equivalents therefore is an amino acid selected from the group consisting of Asn, Asp, Arg and Ala and functional equivalents thereof; h is an amino acid selected from the group consisting of Ile and Val and functional equivalents thereof; k is an amino acid selected from the group consisting of Trp and Na and functional equivalents thereof; n is an amino acid selected from the group consisting of Gln and Met and functional equivalents thereof and $X_k$ is a 3 amino acid peptide.

Examples of preferred linear or cyclic compounds are peptide compounds or analogs thereof having the following formula

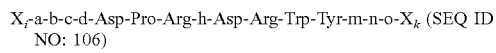
$X_i$-a-b-c-d-Asp-Pro-Arg-h-Asp-Arg-Trp-Tyr-m-n-o-$X_k$ (SEQ ID NO: 106)

wherein $X_i$ is absent or a peptide of between 1 and 4 amino acids; a is an amino acid selected from the group consisting of Ala; Asn, Arg, Phe, Gln, Gly and Pro and functional equivalents thereof; b is an amino acid selected from the group consisting of Leu, Ala, Val, Ile, Arg, Gln and Asn and functional equivalents thereof; c is an amino acid selected from the group consisting of Ala and Cys and functional equivalents thereof; d is an amino acid; h is an amino acid selected from the group consisting of Ile, Val, Leu and Ala and functional equivalents thereof; m is an amino acid selected from Ala and Cys and functional equivalents thereof; n is an amino acid and o is an amino acid selected from the group consisting of Phe, Tyr, Trp and Na and functional equivalents thereof and $X_k$ is a peptide of between 1 and 4 amino acids.

Preferred among this class of cyclic peptide compounds or analogs thereof are compounds having the following formula:

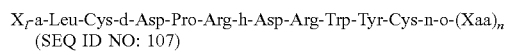
$X_i$-a-Leu-Cys-d-Asp-Pro-Arg-h-Asp-Arg-Trp-Tyr-Cys-n-o-(Xaa)$_n$
(SEQ ID NO: 107)

wherein a is an amino acid selected from the group consisting of Ala, Thr and Ser and functional equivalents thereof; d is an amino acid selected from the group consisting of Asp, Glu, Ser, Ala, Arg, Thr, His, Met, Val and Asn and functional equivalents thereof; h is an amino acid selected from the group consisting of Ile, Val and Leu and functional equivalents thereof; n is an amino acid selected from the group consisting of Gln, Met, Gly, Arg, Ser, Lys, Ala, Asn and Thr and functional equivalents thereof and o is an amino acid selected from the group consisting of Phe and Tyr and functional equivalents thereof.

More preferred are cyclic peptide compounds or analogs thereof having the following formula

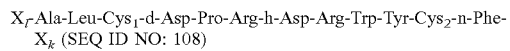
$X_i$-Ala-Leu-Cys$_1$-d-Asp-Pro-Arg-h-Asp-Arg-Trp-Tyr-Cys$_2$-n-Phe-$X_k$ (SEQ ID NO: 108)

wherein d is an amino acid selected from the group consisting of Asp, Glu, Ser, Ala, Arg and functional equivalents thereof; n is an amino acid selected from the group consisting of Gln and Met and $X_k$ is a 3 amino acid peptide.

Exemplary peptides of the present invention include but are not limited to those described in FIG. 8.

In one embodiment, the invention contemplates the use of a compound such as a peptide or peptide analog and the compound comprises the following formula:

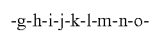
-g-h-i-j-k-l-m-n-o- wherein g is an amino acid; h is an amino acid selected from the group consisting of Ile, Val, Leu, Ala and functional equivalents thereof; i is an amino acid selected from the group consisting of Asp, Glu, Ser, Ala, Thr and functional equivalents thereof; j is an amino acid selected from the group consisting of Ala, Asp, Glu, Phe, Gly, His, Lys, Leu, Met, Asn, Pro, Gln, Arg, Ser, Thr, Val, Tyr and functional equivalents thereof; k is an amino acid selected from the group consisting of Trp, Na, Tyr, Phe and functional equivalents thereof; l is an amino acid selected from the group consisting of Tyr, Phe, Na, Trp and functional equivalents thereof; m is an amino acid selected from the group consisting of Cys, Ala and functional equivalents thereof; n is an amino acid and o is an amino acid selected from the group consisting of Phe Tyr, Trp, Na. These compounds specifically include peptide compounds as well as functional equivalents thereof, fragments thereof, esters, amides, salts and derivatives thereof, and extended peptide chains carrying additional amino acids or peptides at the termini of the sequences.

Preferred among this class of compounds are compounds which comprises the following formula:

a-b-c-d-e-f-g-h-i-j-k-l-m-n-o wherein a is an amino acid; b is an amino acid selected from the group consisting of Leu, Ile, Val, Ala and functional equivalents thereof; c is an amino acid selected from the group consisting of Cys, Ala and functional equivalents thereof; d is an amino acid; e is an amino acid selected from the group consisting of Ala, Cys, Asp, Glu, Phe, His, Ile, Lys, Leu, Met, Asn, Pro, Gln, Arg, Ser, Thr, Val, Trp, Tyr and functional equivalents thereof; f is an amino acid selected from the group consisting of Pro, Gly, Ala and functional equivalents thereof g is an amino acid; h is an amino acid selected from the group consisting of Ile, Val, Leu, Ala and functional equivalents thereof; i is an amino acid selected from the group consisting of Asp, Glu, Ser, Thr, Ala and functional equivalents thereof; j is an amino acid selected from the group consisting of Ala, Asp, Glu, Phe, Gly, His, Lys, Leu, Met, Asn, Pro, Gln, Arg, Ser, Thr, Val, Trp, Tyr and functional equivalents thereof; k is am amino acid selected from the group consisting of Trp, Tyr, Phe, Na and functional equivalents thereof; l is an amino acid selected from the group consisting of Tyr, Phe, Na and functional equivalents thereof; m is an amino acid selected from the group consisting of Cys, Ala and functional equivalents thereof; n is an amino acid; o is an amino acid selected from the group consisting of Tyr, Phe, Na and functional equivalents thereof.

The foregoing compounds can be used and are especially preferred in a method of inhibiting FVIIa activity comprising the steps of:

a) contacting FVIIa with a compound of interest, especially the peptides and peptide analogs described in the foregoing section, in the presence or absence of tissue factor and under conditions which allow binding of the compound to FVIIa to occur and optionally, b) measuring or assessing the amount of FX activation that occurs in the presence of the compound of interest. According to certain aspects of the invention a standard FX activation assay as described herein is employed along with the foregoing method to measure the amount of FX activation that is blocked or inhibited by the compound of interest. This aspect of the present invention may be practiced in vitro or in vivo.

Peptide Crystals and Analogs

Three dimensional structures of peptide compounds can be determined using X-ray crystallography. Structural information derived from a peptide crystal structure can be used for the identification of small bioorganic molecules such as peptidomimetics and synthetic organic molecules which bind FVII/FVIIa and preferably block or prevent a FVIIa mediated or associated process or event. An exemplary approach to such a structure based compound design is described in ("Structure Based Drug Design" Pandi Veerapandian, ed. Marcell Dekker, N.Y. 1997).

The peptide analogs identified using the peptide compounds of the present invention are useful in the therapeutic methods described herein and as pharmaceutical compositions.

Chemical Synthesis

One method of producing the compounds of the invention involves chemical synthesis. This can be accomplished by using methodologies well known in the art (see Kelley, R. F. & Winkler, M. E. in Genetic Engineering Principles and Methods, Setlow, J. K, ed., Plenum Press, N.Y., vol. 12, pp 1–19 (1990), Stewart, J. M. Young, J. D., Solid Phase Peptide Synthesis, Pierce Chemical Co., Rockford, Ill. (1984); see also U.S. Pat. Nos. 4,105,603; 3,972,859; 3,842,067; and 3,862,925).

Peptides of the invention can be conveniently prepared using solid phase peptide synthesis (Merrifield, (1964) J. Am. Chem. Soc., 85:2149; Houghten, (1985) Proc. Natl. Acad. Sci. USA, 82:5132. Solid phase synthesis begins at the carboxy terminus of the putative peptide by coupling a protected amino acid to an inert solid support. The inert solid support can be any macromolecule capable of serving as an anchor for the C-terminus of the initial amino acid. Typically, the macromolecular support is a cross-linked polymeric resin (e.g. a polyamide or polystyrene resin) as shown in FIGS. 1-1 and 1-2, on pages 2 and 4 of Stewart and Young, supra. In one embodiment, the C-terminal amino acid is coupled to a polystyrene resin to form a benzyl ester. A macromolecular support is selected such that the peptide anchor link is stable under the conditions used to deprotect the α-amino group of the blocked amino acids in peptide synthesis. If a base-labile α-protecting group is used, then it is desirable to use an acid-labile link between the peptide and the solid support. For example, an acid-labile ether resin is effective for base-labile Fmoc-amino acid peptide synthesis as described on page 16 of Stewart and Young, supra. Alternatively, a peptide anchor link and a-protecting group that are differentially labile to acidolysis can be used. For example, an aminomethyl resin such as the phenylacetamidomethyl (Pam) resin works well in conjunction with Boc-amino acid peptide synthesis as described on pages 11–12 of Stewart and Young, supra.

After the initial amino acid is coupled to an inert solid support, the α-amino protecting group of the initial amino acid is removed with, for example, trifluoroacetic acid (TFA) in methylene chloride and neutralizing in, for example, triethylamine (TEA). Following deprotection of the initial amino acid's α-amino group, the next α-amino and sidechain protected amino acid in the synthesis is added. The remaining α-amino and, if necessary, side chain protected amino acids are then coupled sequentially in the desired order by condensation to obtain an intermediate compound connected to the solid support. Alternatively, some amino acids may be coupled to one another to form a fragment of the desired peptide followed by addition of the peptide fragment to the growing solid phase peptide chain.

The condensation reaction between two amino acids, or an amino acid and a peptide, or a peptide and a peptide can be carried out according to the usual condensation methods such as the axide method, mixed acid anhydride method, DCC (N,N'-dicyclohexylcarbodiimide) or DIC (N,N'-diisopropylcarbodiimide) methods, active ester method, p-nitrophenyl ester method, BOP (benzotriazole-1-yl-oxy-tris [dimethylamino] phosphonium hexafluorophosphate) method, N-hydroxysuccinic acid imido ester method, etc, and Woodward reagent K method.

It is common in the chemical syntheses of peptides to protect any reactive side-chain groups of the amino acids with suitable protecting groups. Ultimately, these protecting groups are removed after the desired polypeptide chain has been sequentially assembled. Also common is the protection of the α-amino group on an amino acid or peptide fragment while the C-terminal carboxy group of the amino acid or peptide fragment reacts with the free N-terminal amino group of the growing solid phase polypeptide chain, followed by the selective removal of the α-amino group to permit the addition of the next amino acid or peptide fragment to the solid phase polypeptide chain. Accordingly, it is common in polypeptide synthesis that an intermediate compound is produced which contains each of the amino acid residues located in the desired sequence in the peptide chain wherein individual residues still carry side-chain protecting groups. These protecting groups can be removed substantially at the same time to produce the desired polypeptide product following removal from the solid phase.

α- and ε-amino side chains can be protected with benzyloxycarbonyl (abbreviated Z), isonicotinyloxycarbonyl (iNOC), o-chlorobenzyloxycarbonyl [Z(2Cl)], p-nitrobenzyloxycarbonyl [Z(NO$_2$)], p-methoxybenzyloxycarbonyl [Z(OMe)], t-butoxycarbonyl (Boc), t-amyloxycarbonyl (Aoc), isobornyloxycarbonyl, adamantyloxycarbonyl, 2-(4-biphenyl)-2-propyloxycarbonyl (Bpoc), 9-fluorenylmethoxycarbonyl (Fmoc), methylsulfonyethoxycarbonyl (Msc), trifluoroacetyl, phthalyl, formyl, 2-nitrophenylsulphenyl (NPS), diphenylphosphinothioyl (Ppt), and dimethylphosphinothioyl (Mpt) groups, and the like.

Protective groups for the carboxy functional group are exemplified by benzyl ester (OBzl), cyclohexyl ester (Chx), 4-nitrobenzyl ester (ONb), t-butyl ester (Obut), 4-pyridylmethyl ester (OPic), and the like. It is often desirable that specific amino acids such as arginine, cysteine, and serine possessing a functional group other than amino and carboxyl groups are protected by a suitable protective group. For example, the guanidino group of arginine may be protected with nitro, p-toluenesulfonyl, benzyloxycarbonyl, adamantyloxycarbonyl, p-methoxybenzesulfonyl, 4-methoxy-2,6-dimethylbenzenesulfonyl (Nds), 1,3,5-trimethylphenysulfonyl (Mts), and the like. The thiol group of cysteine can be protected with p-methoxybenzyl, trityl, and the like.

Many of the blocked amino acids described above can be obtained from commercial sources such as Novabiochem (San Diego, Calif.), Bachem Calif. (Torrence, Calif.) or Peninsula Labs (Belmont, Calif.).

Stewart and Young, supra, provides detailed information regarding procedures for preparing peptides. Protection of α-amino groups is described on pages 14–18, and side chain blockage is described on pages 18–28. A table of protecting groups for amine, hydroxyl and sulfhydryl functions is provided on pages 149–151.

After the desired amino acid sequence has been completed, the peptide can be cleaved away from the solid support, recovered and purified. The peptide is removed from the solid support by a reagent capable of disrupting the peptide-solid phase link, and optionally deprotects blocked side chain functional groups on the peptide. In one embodiment, the peptide is cleaved away from the solid phase by acidolysis with liquid hydrofluoric acid (HF), which also removes any remaining side chain protective groups. Preferably, in order to avoid alkylation of residues in the peptide (for example, alkylation of methionine, cysteine, and tyrosine residues), the acidolysis reaction mixture contains thio-cresol and cresol scavengers. Following HF cleavage, the resin is washed with ether, and the free peptide is extracted from the solid phase with sequential washes of acetic acid solutions. The combined washes are lyophilized, and the peptide is purified.

Disulfide Linked Peptides

As described above, some embodiments of the invention are cyclized by formation of a disulfide bond between cysteine residues. Such peptides can be made by chemical synthesis as described above and then cyclized by any convenient method used in the formation of disulfide linkages. For example, peptides can be recovered from solid phase synthesis with sulfhydryls in reduced form, dissolved in a dilute solution wherein the intramolecular cysteine concentration exceeds the intermolecular cysteine concentration in order to optimize intramolecular disulfide bond formation, such as a peptide concentration of 25 mM to 1 μM, and preferably 500 μM to 1 μM, and more preferably 25 μM to 1 μM, and then oxidized by exposing the free sulfhydryl groups to a mild oxidizing agent that is sufficient to generate intramolecular disulfide bonds, e.g. molecular oxygen with or without catalysts such as metal cations, potassium ferricyanide, sodium tetrathionate, etc. In one embodiment, the peptides are cyclized as described in Example 2 below. Alternatively, the peptides can be cyclized as described in Pelton et al., (1986) J. Med. Chem., 29:2370–2375.

Cyclization can be achieved by the formation for example of a disulfide bond or a lactam bond between Cys residues. Residues capable of forming a disulfide bond include for example Cys, Pen, Mpr, and Mpp and its 2-amino group-containing equivalents. Residues capable of forming a lactam bridge include for example, Asp, Glu, Lys, Orn, αβ-diaminobutyric acid, diaminoacetic acid, aminobenzoic acid and mercaptobenzoic acid. The compounds herein can be cyclized for example via a lactam bond which can utilize the side chain group of a non-adjacent residue to form a covalent attachment to the N-terminus amino group of Cys or other amino acid. Alternative bridge structures also can be used to cyclize the compounds of the invention, including for example, peptides and peptidomimetics, which can cyclize via S—S, CH2-S, CH2-O—CH2, lactam ester or other linkages.

Recombinant Synthesis

In a further embodiment, the present invention encompasses a composition of matter comprising isolated nucleic acid, preferably DNA, encoding a peptide described herein. DNAs encoding the peptides of the invention can be prepared by a variety of methods known in the art. These methods include, but are not limited to, chemical synthesis by any of the methods described in Engels et al., (1989) Agnew. Chem. Int. Ed. Engl., 28:716–734, the entire disclosure of which is incorporated herein by reference, such as the triester, phosphite, phosphoramidite and H-phosphonate methods. In one embodiment, codons preferred by the expression host cell are used in the design of the encoding DNA. Alternatively, DNA encoding the peptide can be altered to encode one or more variants by using recombinant DNA techniques, such as site specific mutagenesis (Kunkel et al., (1991) Methods Enzymol. 204:125–139; Carter, P., et al., (186) Nucl. Acids. Res. 13:4331; Zoller, M. J. et al., (1982) Nucl. Acids Res. 10:6487), cassette mutagenesis (Wells, J. A., et al., (1985) Gene 34:315), restriction selection mutagenesis (Wells, J. A., et al., (1986) Philos. Trans, R. Soc. London SerA 317, 415), and the like.

The invention further comprises an expression control sequence operably linked to the DNA molecule encoding a peptide of the invention, and an expression vector, such as a plasmid, comprising the DNA molecule, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells.

Suitable host cells for expressing the DNA include prokaryote, yeast, or higher eukaryote cells. Suitable prokaryotes include but are not limited to eubacteria, such as Gram-negative or Gram-positive organisms, for example, Enterobacteriaceae such as *E. coli*. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635).

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. Suitable host cells for expression also are derived from multicellular organisms. Examples of invertebrate cells include insect cells such as *Drosophila* S2 and *Spodoptera* Sf9, as well as plant cells. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

Examples of useful mammalian host cells include monkey kidney CV1 line transformed by SV40 (COS-7, ATCC CRL 1651); human embryonic kidney line (293 or 293 cells subcloned for growth in suspension culture, Graham et al., (1977) J. Gen Virol., 36:59); baby hamster kidney cells (BHK, ATCC CCL 10); Chinese hamster ovary cells/-DHFR (CHO, Urlaub and Chasin, (1980) Proc. Natl. Acad. Sci. USA, 77:4216); mouse sertoli cells (TM4, Mather, (1980) Biol. Reprod., 23:243–251); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., (1982) Annals N.Y. Acad. Sci., 383:44–68); MRC 5 cells; FS4 cells; and a human hepatoma cell line (Hep G2).

For expression in prokaryotic hosts, suitable vectors include pBR322 (ATCC No. 37,017), phGH107 (ATCC No. 40,011), pBO475, pS0132, pRIT5, any vector in the pRIT20 or pRIT30 series (Nilsson and Abrahmsen, (1990) Meth. Enzymol., 185:144–161), pRIT2T, pKK233-2, pDR540 and pPL-lambda. Prokaryotic host cells containing the expression vectors of the present invention include *E. coli* K12 strain 294 (ATCC NO. 31446), *E coli* strain JM101 (Messing et al., (1981) Nucl. Acid Res., 9:309), *E. coli* strain B, *E. coli* strain $_x$1776 (ATCC No. 31537), *E. coli* c600 (Appleyard, *Genetics*, 39: 440 (1954)), *E. coli* W3110 (F-, gamma-, prototrophic, ATCC No. 27325), *E. coli* strain 27C7 (W3110, tonA, phoA E15, (argF-lac)169, ptr3, degP41, ompT, kan$^r$) (U.S. Pat. No. 5,288,931, ATCC No. 55,244), *Bacillus subtilis, Salmonella typhimurium, Serratia marcesans*, and *Pseudomonas* species.

For expression in mammalian host cells, useful vectors include vectors derived from SV40, vectors derived from cytomegalovirus such as the pRK vectors, including pRK5 and pRK7 (Suva et al., (1987) Science, 237:893–896; EP 307,247 (Mar. 15, 1989), EP 278,776 (Aug. 17, 1988)) vectors derived from vaccinia viruses or other pox viruses, and retroviral vectors such as vectors derived from Moloney's murine leukemia virus (MoMLV).

Optionally, the DNA encoding the peptide of interest is operably linked to a secretory leader sequence resulting in secretion of the expression product by the host cell into the culture medium. Examples of secretory leader sequences include stII, ecotin, lamB, herpes GD, lpp, alkaline phosphatase, invertase, MIP.5 and alpha factor. Also suitable for use herein is the 36 amino acid leader sequence of protein A (Abrahmsen et al., (1985) EMBO J., 4:3901).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, CaPO$_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., Molecular Cloning (2nd ed.), Cold Spring Harbor Laboratory, NY (1989), is generally used for prokaryotes or other cells that contain substantial cell-wall barriers. Infection with *Agrobacterium tumefaciens* is used for transformation of certain plant cells, as described by Shaw et al., (1983) Gene, 23:315 and WO 89/05859 published 29 Jun. 1989. For mammalian cells without such cell walls, the calcium phosphate precipitation method described in sections 16.30–16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., (1977) J. Bact., 130:946 and Hsiao et al., (1979) Proc. Natl. Acad. Sci. (USA), 76:3829. However, other methods for introducing DNA into cells such as by nuclear injection, electroporation, or by protoplast fusion may also be used.

Other preferred vectors can be constructed using standard techniques by combining the relevant traits of the vectors described above. Relevant traits include the promoter, the ribosome binding site, the gene of interest or gene fusion (the Z domain of protein A and gene of interest and a linker), the antibiotic resistance markers, and the appropriate origins of replication.

A variation on the above procedures contemplates the use of gene fusions, wherein the gene encoding the desired peptide is associated, in the vector, with a gene encoding another protein or a fragment of another protein. This results in the desired peptide being produced by the host cell as a fusion with another protein or peptide. The "other" protein or peptide is often a protein or peptide which can be secreted by the cell, making it possible to isolate and purify the desired peptide from the culture medium and eliminating the necessity of destroying the host cells which arises when the desired peptide remains inside the cell. Alternatively, the fusion protein can be expressed intracellularly. It is useful to use fusion proteins that are highly expressed.

The use of gene fusions, though not essential, can facilitate the expression of heterologous peptides in insect cells as well as the subsequent purification of those gene products. Protein A fusions are often used because the binding of protein A, or more specifically the Z domain of protein A, to IgG provides an "affinity handle" for the purification of the fused protein. For example, a DNA sequence encoding the desired peptide ligand can be fused by site directed mutagenesis to the genen for a consensus domain of protein A known as the Z domain (Nilsson et al., (1987) Protein Engineering 1:107–113). After expression and secretion the fusion protein can be enzymatically cleaved to yield free peptide which can be purified from the enzymatic mix (see, e.g., Varadarajan et al., (1985) Proc. Natl. Acad. Sci USA 82:5681–5684; Castellanos-Serra et al., (1996) FEBS Letters 378:171–176; Nilsson et al., (1996) J. Biotechnol. 48:241–250).

Fusion proteins can be cleaved using chemicals, such as cyanogen bromide, which cleaves at a methionine, or hydroxylamine, which cleaves between an Asn and Gly residue. Using standard recombinant DNA methodology, the nucleotide base pairs encoding these amino acids may be inserted just prior to the 5' end of the gene encoding the desired peptide.

Alternatively, one can employ proteolytic cleavage of fusion protein. Carter, in *Protein Purification: From Molecular Mechanisms to Large-Scale Processes*, Ladisch et al., eds. (American Chemical Society Symposium Series No. 427, 1990), Ch 13, pages 181–193.

Proteases such as Factor Xa, thrombin, and subtilisin or its mutants, and a number of others have been successfully used to cleave fusion proteins. Preferred according to the present invention for the production of peptide ligands of less than about 30 amino acids is the protease trypsin which is highly specific for Arg and Lys residues. Trypsin cleavage is discussed generally in Nilsson et al. (1996) J. Biotech. 48:241 and Smith et al., Methods Mol. Biol. 32:289. Typically, a peptide linker that is amenable to cleavage by the protease used is inserted between the "other" protein (e.g., the Z domain of protein A) and the desired peptide. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The peptide may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the peptide is treated with a chaotrope, such a guanidine HCl, and is then treated with a redox buffer, containing, for example, reduced and oxidized dithiothreitol or glutathione at the appropriate ratios, pH, and temperature, such that the peptide is refolded to its native structure.

The host cells referred to in this disclosure encompass cells in in vitro culture as well as cells that are within a host animal.

In cyclized embodiments of the invention, the recombinantly produced peptide can be cyclized by formation of an intramolecular disulfide bond as described above.

The peptide compounds of the invention can be modified at the N-terminus or the C-terminus using an amino-protecting group or carboxy protecting group, respectively. Numerous such modifications will be apparent to those skilled in the art. For example, the N-terminus of a peptide or peptide analog can be chemically modified such that the N-terminal amino group is substituted for example by an acetyl, cyclopentylcarboxy, isoquinolylcarboxy, furoyl, tosyl, pyrazinecarboxy, or other such group, which can be sustituted by a substituent as described herein. The N-terminal amino group also can be substituted, for example, with a reverse amide bond. It should be recognized that the term amino group is used broadly herein to refer to any free amino group, including a primary, secondary, or teriary amino group, present in a peptide. By contrast the term N-terminus refers to the α-amino group of the first amino acid present in a peptide written in the conventional manner.

The N-terminus of a peptide of the invention can be protected by linking thereto an amino protecting group. The term "amino protecting group" is used broadly herein to refer to a chemical group that can react with a free amino group, including for example the α-amino group present at the N-terminus of a peptide of the invention. By virtue of reacting therewith, an amino protecting group protects the otherwise reactive amino group against undesirable reactions as can occur for example during a synthetic procedure or due to exopeptidase activity on a final compound.

Modification of an amino group also can provide additional advantages, including, for example, increasing the solubility or the activity of the compound. Compounds having these modifications are meant to be included within the compounds of the present invention since their construction is within the ability of the skilled artisan given the present disclosure. Various amino protecting groups are known in the art and include, for example, acyl groups such as an acetyl, picolyl, tert-butylacetyl, tert-butyloxycarbonyl, benzyloxycarbonyl, benzoyl groups, including for example a benzyloxime such as a 2-aryl-2-o-benzyloxime as well as an amino acyl residue which itself can be modified by an amino-protecting group. Other amino-protecting groups are described for example in *The Peptides*, eds. Gross and Meienhofer, Vol. 3 (acedemic Press, Inc. N.Y. 1981) and Greene and Wuts, in *Protective groups in Organic Synthesis* 2d ed., pages 309–405 (John Wiley & sons, New York (1991), each of which is incorporated herein by reference. The product of any such modification of the N-terminus amino group of a peptide or peptide analog of the invention is referred to herein as an "N-terminal derivative".

Similarly a carboxy group such as the carboxy group present at the C-terminus of a peptide can be chemically modified using a carboxy-protecting group. The terms "carboxy group" and "C-terminus" are used in a manner consistent with the terms amino groups and N-terminus as defined above. A carboxy group such as that present at the C-terminus of a peptide can be modified by reduction of the C-terminal carboxy-group to an alcohol or aldehyde or by formation of an oral ester or by substituion of the carboxy-group with a substituent such as a thiazolyl, cyclohexyl, or other group. Oral esters are well known in the art and include, for example, alkoxymethyl groups such as methoxymethyl, ethoxymethyl, propoxymethyl, isopropoxy methyl, and the like.

Peptide Combinations

A. Multimerization Domains

According to a preferred embodiment of the invention, the peptide compounds are combined with a multimerization domain. According to this aspect of the invention, hybrid molecules are provided which comprise at least two distinct domains. Each molecule comprises a peptide domain and a multimerization domain. According to the present invention, the peptide domain is joined to a multimerization domain such as an immunoglobulin Fc region, optionally via a flexible linker domain.

The hybrid molecules of the present invention are constructed by combining the peptide with a suitable multimerization domain. Ordinarily, when preparing the hybrid molecules of the present invention, nucleic acid encoding the peptide will be operably linked to nucleic acid encoding the multimerization domain sequence. Typically, the construct encodes a fusion protein wherein the C-terminus of the peptide is joined to the N-terminus of the multimerization domain. However, fusions where, for example, the N-terminus of the peptide is joined to the C-terminus of the multimerization domain are also possible.

Preferred multimerization domains are immunoglobulin constant region sequences. Typically, in such fusions the encoded hybrid molecule will retain at least functionally active hinge, CH2 and CH3 domains of the constant region of an immunoglobulin heavy chain. Fusions are also made, for example, to the C-terminus of the Fc portion of a constant domain, or immediately N-terminal to the CH1 of the heavy chain or the corresponding region of the light chain.

The precise amino acid site at which the fusion of the peptide to the immunoglobulin constant domain is made is not critical; particular sites are well known and may be selected in order to optimize the biological activity, secretion, or binding characteristics. In this regard, the skilled artisan may reference the construction of various immunoadhesins described in the literature (U.S. Pat. Nos. 5,116,964, 5,714,147 and 5,336,603; Capon et al., (1989) Nature 337:525–531; Traunecker et al., (1989) Nature 339:68–70; and Byrn et al., (1990) Nature 344:667–670; Watson et al., (1990) J. Cell. Biol. 110:2221–2229; Watson et al., (1991) Nature 349:164–167; Aruffo et al., (1990) Cell 61:1303–1313; Linsley et al., (1991) J. Exp. Med. 173:721–730; Lisley et al., J. Exp. Med. 174:561–569; Stamenkovic et al., Cell 66:1133–1144; Ashkenazi et al., (1991) Proc. Natl. Acad. Sci. USA 88:10535–10539; Lesslauer et al., (1991) Eur. J. Immunol. 27:2883–2886; and Peppel et al., (1991) J. Exp. Med. 174:1483–1489; Mohler et al., (1993) J. Immunol. 151:1548–1561); Bennett et al., (1991) J. Biol. Chem. 266:23060–23067; Kurschner et al., (1992) J. Biol. Chem. 267:9354–9360; Chalupny et al., (1992) PNAS USA 89:10360–10364; Ridgway and Gorman, (1991) J. Cell. Biol. 115, Abstract No. 1448).

According to a particular aspect, an immunoglobulin type multimerization domain is selected to provide a multimer such as a dimer having an immunoglobulin Fc region. Therefore, the peptide is joined, in particular aspects, to an immunoglobulin heavy chain constant domain to provide a multimer comprising a functional Fc domain. In this case, DNA encoding an immunoglobulin chain-peptide sequence is typically coexpressed with the DNA encoding a second peptide-immunoglobulin heavy chain fusion protein. Upon secretion, the hybrid heavy chain will be covalently associated to provide an immunoglobulin-like structure comprising two disulfide-linked immunoglobulin heavy chains.

Preferably, the Fc region is a human Fc region, e.g. a native sequence human Fc region human IgG1 (A and non-A allotypes), IgG2, IgG3 or IgG4 Fc region.

In a preferred embodiment, the peptide sequence is fused to the N-terminus of the Fc region of immunoglobulin $G_1$ ($IgG_1$). It is possible to fuse the entire heavy chain constant region to the peptide sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the peptide amino acid sequence is fused to (a) the hinge region and CH2 and CH3 or (b) the CH1, hinge, CH2 and CH3 domains, of an IgG heavy chain. In a preferred embodiment the peptide ligand amino acid sequence is fused to (a) the hinge region and (b) the CH3 domain of IgG1.

According to a particular aspect of this embodiment, hybrid molecules comprising a peptide and a multimerization domain are assembled as multimers, for example homodimers, or heterodimers or even heterotetramers. Homodimers result from the pairing or crosslinking of two monomers comprising a peptide and a multimerization domain. However, it is not essential that two identical monomers pair. According to a particular aspect of the invention a hybrid molecule as defined herein comprising a peptide and a multimerization domain such as an immunoglobulin constant domain may pair with a companion immunoglobulin chain comprising one arm of an immunoglobulin. Various exemplary assembled hybrid molecules within the scope of the present invention are schematically diagramed below:

(a) ACH
(b) ACH-ACH
(c) ACH-VHCH-VLCL
(d) ACH-VHCH wherein each A represents identical or different peptide;
VL is an immunoglobulin light chain variable domain;
VH is an immunoglobulin heavy chain variable domain;
CL is an immunoglobulin light chain constant domain and
CH is an immunoglobulin heavy chain constant domain.

The hybrid molecules described herein are most conveniently constructed by fusing the cDNA sequence encoding the peptide portion in-frame to an immunoglobulin cDNA sequence. However, fusion to genomic immunoglobulin fragments can also be used (see, e.g. Aruffo et al., (1990), Cell 61:1303–1313; and Stamenkovic et al. (1991), Cell 66:1133–1144). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the peptides and the immunoglobulin parts of the hybrid molecule are inserted in tandem into a plasmid vector that directs efficient expression in the chosen host cells.

Alternatively, and especially in embodiments where the peptide is synthesized by, for example standard solid phase synthesis techniques, the peptide may be linked to the multimerization domain by any of a variety of means familiar to those of skill in the art. Covalent attachment is typically the most convenient, but other forms of attachment may be employed depending upon the application. Examples of suitable forms of covalent attachment include the bonds resulting from the reaction of molecules bearing activated chemical groups with amino acid side chains in the multimerization domain and can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Peptide Fusions

According to the present invention, the peptide is optionally linked to, for example, another peptide either directly or via a flexible peptide linker. According to the present invention, the linker domain, is any group of molecules that provides a spatial bridge between two or more peptide domains as described in more detail herein below. According to this aspect of the invention, peptides are linked together, as for example in a fusion protein.

Linker Domains

According to the present invention, the peptide domain is optionally linked to, for example, another peptide domain or a multimerization domain via a flexible peptide linker. The linker component of the hybrid molecule of the invention does not necessarily participate in but may contribute to the function of the hybrid molecule. Therefore, according to the present invention, the linker domain, is any group of molecules that provides a spatial bridge between two or more peptide domains or a peptide domain and a multimerization domain.

The linker domain can be of variable length and makeup. It is generally, the length of the linker domain and not its structure that is important. The linker domain preferably allows for the peptide domain of the hybrid molecule to bind, substantially free of spacial/conformational restrictions to the coordinant FVII/FVIIa molecule. Therefore, the length of the linker domain is dependent upon the character of the two functional, e.g., the peptide and the multimerization domains of the hybrid molecule.

One skilled in the art will recognize that various combinations of atoms provide for variable length molecules based upon known distances between various bonds (Morrison, and Boyd, Organic Chemistry, 3rd Ed, Allyn and Bacon, Inc., Boston, Mass. (1977)). For example, the linker domain may be a polypeptide of variable length. The amino acid composition of the polypeptide determines the character and length of the linker. Exemplary linker domains comprise one or more Gly and or Ser/Arg residues.

Research and Diagnostic Compositions

In a preferred embodiment, the peptides of the invention are non-covalently adsorbed or covalently bound to a macromolecule, such as a solid support. It will be appreciated that the invention encompasses both macromolecules complexed with the peptides. In general, the solid support is an inert matrix, such as a polymeric gel, comprising a three dimensional structure, lattice or network of a material. Almost any macromolecule, synthetic or natural, can form a gel in a suitable liquid when suitably cross-linked with a bifunctional reagent. Preferably, the macromolecule selected is convenient for use in affinity chromatography. Most chromatographic matrices used for affinity chromatography are xerogels. Such gels shrink on drying to a compact solid comprising only the gel matrix. When the dried xerogel is resuspended in the liquid, the gel matrix imbibes liquid, swells and returns to the gel state. Xerogels suitable for use herein include polymeric gels, such as cellulose, cross-linked dextrans (e.g. Sepharose), agarose, cross-linked agarose, polyacrylamide gels, and polyacrylamide-agarose gels.

Alternatively, aerogels can be used for affinity chromatography. These gels do not shrink on drying but merely allow penetration of the surrounding air. When the dry gel is exposed to liquid, the latter displaces the air in the gel. Aerogels suitable for use herein include porous glass and ceramic gels.

Also encompassed herein are the peptides of the invention coupled to derivatized gels wherein the derivative moieties facilitate the coupling of the peptide ligands to the gel matrix and avoid steric hindrance of the peptide-FVII/FVIIa interaction in affinity chromatography. Alternatively, spacer arms can be interposed between the gel matrix and the peptide ligand for similar benefits.

In another embodiment, the invention provides fusion proteins in which a selected or desired polypeptide is fused at its N-terminus or its C-terminus, or at both termini, to one or more of the present peptides.

Pharmaceutical Compositions

Pharmaceutical compositions which comprise the compounds, including the hybrid molecules of the invention may be formulated and delivered or administered in a manner best suited to the particular FVII/FVIIa mediated disease or disorder being treated including formulations suitable for parental, topical, oral, local, aerosol or transdermal administration or delivery of the compounds. In indications where the reduction of TF-FVIIa dependent coagulation is related to circulation of blood through stents or artificial valves or related to extracorporeal circulation including blood removed in-line from a patient in such processes as dialysis procedures, blood filtration, or blood bypass during surgery suitable formulations include those appropriate for coating devices such as stents, valves and filtration devices.

Somewhat more particularly, suitable compositions of the present invention comprise any of the compounds described herein along with a pharmaceutically acceptable carrier, the nature of the carrier differing with the mode of administration delivery or use, for example, in oral administration, usually using a solid carrier and in i.v. administration, a liquid salt solution carrier. For local administration such as may be appropriate where TF-FVIIa dependent coagulation is related to circulation of blood through artificial devices such as stents or valves the peptides may be linked, for example, covalently, to the artificial device preventing local thrombus formation. Alternatively, the peptide may be provided in a formulation that would allow for the peptide to slowly elute from the device providing both local and systemic protection against events associated with TF-FVIIa dependent coagulation. As but one example, stents adsorbed with peptides can be employed following angioplasty or other surgical procedure.

The compositions of the present invention include pharmaceutically acceptable components that are compatible with the subject and the compound of the invention. These generally include suspensions, solutions and elixirs, and most especially biological buffers, such as phosphate buffered saline, saline, Dulbecco's Media, and the like. Aerosols may also be used, or carriers such as starches, sugars, microcrystalline cellulose, diluents, granulating agents, lubricants, binders, disintegrating agents, and the like (in the case of oral solid preparations, such as powders, capsules, and tablets).

As used herein, the term "pharmaceutically acceptable" generally means approved by a regulatory agency of the Federal or a state government or listed in the U.S. Pharmacopeia or other generally recognized pharmacopeia for use in animals, and more particularly in humans.

The of choice can be accomplished using a variety of the aforementioned buffers, or even excipients including, for example, pharmaceutical grades of mannitol, lactose, starch, magnesium stearate, sodium saccharin cellulose, magnesium carbonate, and the like. "PEGylation" of the compositions may be achieved using techniques known to the art (see for example International Patent Publication No. WO92/16555, U.S. Pat. No. 5,122,614 to Enzon, and International Patent Publication No. WO92/00748).

A preferred route of administration of the present invention is in the aerosol or inhaled form. The compounds of the present invention, combined with a dispersing agent, or dispersant, can be administered in an aerosol formulation as a dry powder or in a solution or suspension with a diluent.

As used herein, the term "dispersant" refers to a agent that assists aerosolization of the compound or absorption of the protein in lung tissue, or both. Preferably the dispersant is pharmaceutically acceptable. As used herein, the term "pharmaceutically acceptable" means approved by a regulatory agency of the Federal or a state government or listed in the U.S. Pharmacopeia or other generally recognized pharmacopeia for use in animals, and more particularly in humans. Suitable dispersing agents are well known in the art, and include but are not limited to surfactants and the like. For example, surfactants that are generally used in the art to reduce surface induced aggregation of the compound, especially the peptide compound, caused by atomization of the solution forming the liquid aerosol may be used. Nonlimiting examples of such surfactants include polyoxyethylene fatty acid esters and alcohols, and polyoxyethylene sorbitan fatty acid esters. Amounts of surfactants used will vary, being generally within the range or 0.001 and 4% by weight of the formulation. In a specific aspect, the surfactant is polyoxyethylene sorbitan monooleate or sorbitan trioleate. Suitable surfactants are well known in the art, and can be selected on the basis of desired properties, depending on the specific formulation, concentration of the compound, diluent (in a liquid formulation) or form of powder (in a dry powder formulation), etc.

Moreover, depending on the choice of the compound, the desired therapeutic effect, the quality of the lung tissue (e.g., diseased or healthy lungs), and numerous other factors, the liquid or dry formulations can comprise additional components, as discussed further below.

The liquid aerosol formulations generally contain the compound and a dispersing agent in a physiologically acceptable diluent. The dry powder aerosol formulations of the present invention consist of a finely divided solid form of the compound and a dispersing agent. With either the liquid or dry powder aerosol formulation, the formulation must be aerosolized. That is, it must be broken down into liquid or solid particles in order to ensure that the aerosolized dose actually reaches the alveoli. In general the mass median dynamic diameter will be 5 micrometers or less in order to ensure that the drug particles reach the lung alveoli (Wearley, L. L., 1991, Crit. Rev. in Ther. Drug Carrier Systems 8:333). The term "aerosol particle" is used herein to describe the liquid or solid particle suitable for pulmonary administration, i.e., that will reach the alveoli. Other considerations such as construction of the delivery device, additional components in the formulation and particle characteristics are important. These aspects of pulmonary administration of a drug are well known in the art, and manipulation of formulations, aerosolization means and construction of a delivery device require at most routine experimentation by one of ordinary skill in the art.

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellent may be any propellant generally used in the art. Specific nonlimiting examples of such useful propellants are a chloroflourocarbon, a hydrofluorocarbon, a hydochlorofluorocarbon, or a hydrocarbon, including triflouromethane, dichlorodiflouromethane, dichlorotetrafuoroethanol, and 1,1,1,2-tetraflouroethane, or combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation. Metered dose inhalers are well known in the art.

Once the compound reaches the lung, a number of formulation-dependent factors effect the drug absorption. It will be appreciated that in treating a disease or disorder that requires circulatory levels of the compound, such factors as aerosol particle size, aerosol particle shape, the presence or absence of infection, lung disease or emboli may affect the absorption of the compounds. For each of the formulations described herein, certain lubricators, absorption enhancers, protein stabilizers or suspending agents may be appropriate. The choice of these additional agents will vary depending on the goal. It will be appreciated that in instances where local delivery of the compounds is desired or sought, such variables as absorption enhancement will be less critical.

Liquid Aerosol Formulations

The liquid aerosol formulations of the present invention will typically be used with a nebulizer. The nebulizer can be either compressed air driven or ultrasonic. Any nebulizer known in the art can be used in conjunction with the present invention such as but not limited to: Ultravent, Mallinckrodt, Inc. (St. Louis, Mo.); the Acorn II nebulizer (Marquest Medical Products, Englewood Colo.). Other nebulizers useful in conjunction with the present invention are described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971 and U.S. Pat. No. 4,635,627 issued Jan. 13, 1971.

The formulation may include a carrier. The carrier is a macromolecule which is soluble in the circulatory system and which is physiologically acceptable where physiological acceptance means that those of skill in the art would accept injection of said carrier into a patient as part of a therapeutic regime. The carrier preferably is relatively stable in the circulatory system with an acceptable plasma half life for clearance. Such macromolecules include but are not limited to Soya lecithin, oleic acid and sorbitan trioleate, with sorbitan trioleate preferred.

The formulations of the present embodiment may also include other agents useful for protein stabilization or for the regulation of osmotic pressure. Examples of the agents include but are not limited to salts, such as sodium chloride, or potassium chloride, and carbohydrates, such as glucose, galactose or mannose, and the like.

Aerosol Dry Powder Formulations

It is also contemplated that the present pharmaceutical formulation will be used as a dry powder inhaler formulation comprising a finely divided powder form of the compound and a dispersant. The form of the compound will generally be a lyophilized powder. Lyophilized forms of peptide compounds can be obtained through standard techniques.

In another embodiment, the dry powder formulation will comprise a finely divided dry powder containing one or more compounds of the present invention, a dispersing agent and also a bulking agent. Bulking agents useful in conjunction with the present formulation include such agents as lactose, sorbitol, sucrose, or mannitol, in amounts that facilitate the dispersal of the powder from the device.

Therapeutic Methods

The compounds of the present invention can be used therapeutically to prevent the biological activity of the TF-FVIIa complex. The inhibition of TF-FVIIa is desirable in indications where the reduction of TF-FVIIa dependent coagulation is implicated. These situations include but are not limited to the prevention of arterial thrombosis in combination with thrombolytic therapy. It has been suggested that the TF-FVIIa plays a significant role in a variety of clinical states including deep venous thrombosis, arterial thrombosis, stroke, DIC, septic shock, cardiopulmonary bypass surgery, adult respiratory distress syndrome, hereditary angioedema. Inhibitors of TF-FVIIa may therefore play important roles in the regulation of inflammatory and/or thrombotic disorders.

Thus the present invention encompasses a method for preventing TF-FVIIa mediated event in a human comprising administering to a patient in need thereof a therapeutically effective amount of the compound of the present invention. A therapeutically effective amount of the compound of the present invention is predetermined to achieve the desired effect. The amount to be employed therapeutically will vary depending upon therapeutic objectives, the routes of administration and the condition being treated. Accordingly, the dosages to be administered are sufficient to bind to available FVII/FVIIa and form an inactive complex leading to decreased coagulation in the subject being treated.

The therapeutic effectiveness is measured by an improvement in one or more symptoms associated with the TF-FVIIa dependant coagulation. Such therapeutically effective dosages can be determined by the skilled artisan and will vary depending upon the age condition, sex and condition of the subject being treated. Suitable dosage ranges for systemic administration are typically between about 1 μg/kg to up to 100 mg/kg or more and depend upon the route of administration. According to the present invention a preferred therapeutic dosage is between about 1 μg/kg body weight and about 5 mg/kg body weight. For example, suitable regimens include intravenous injection or infusion sufficient to maintain concentration in the blood in the ranges specified for the therapy contemplated.

The conditions characterized by abnormal thrombosis include those involving the arterial and venous vasculature. With respect to the coronary arterial vasculature, abnormal thrombus formation characterizes, for example, the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA). With respect to the venous vasculature, abnormal thrombus formation characterizes the condition observed in patients undergoing surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly associated with both vascular systems during septic shock, certain viral infections and cancer, a condition wherein there is a rapid consumption of coagulation factors and systemic coagulation which results in the formation of life threatening thrombi occurring throughout the microvasculature leading to wide spread organ failure.

The following examples are offered by way of illustration and not by way of limitation. The disclosures of all citations in the specification are expressly incorporated herein by reference.

EXAMPLES

Example I

Identification and Characterization of Peptides that Bind FVIIa and Inhibit FX Activation and Clotting Methods Phage Libraries—Random sequence polyvalent peptide phage libraries have been described previously (Lowman H. B. et al. Biochemistry (1998) 37:8870). Peptide libraries were constructed of the form $X_iCX_jCX_k$ (where X was any of the 20 naturally occuring L-amino acids and j ranged from 4–10 and i+j+k=18), an unconstrained library $X_{20}$, and $X_4CX_2GPX_4CX_4$. Each of the 10 libraries had in excess of $10^8$ clones.

Selection Conditions—$TF_{1-243}$ (Paborsky, L. R. et al. (1991) J. Biol. Chem. 266: 21911) or recombinant human FVIIa (2 μg/ml each) were immobilized directly to Maxisorp plates (Nunc) in 50 mM ammonium bicarbonate, pH 9.3 by incubating overnight at 4° C. Wells were blocked using Sorting Buffer (50 mM HEPES, pH7.2, 5 mM $CaCl_2$, 5 mM $MgCl_2$, 150 mM NaCl, 1% BSA) for 1 h at 25° C. Recombinant human FVIIa (2 μg/ml) in Sorting Buffer was added for 30 min to wells previously coated and blocked with TF to form the TF-FVIIa complex. Phage from the libraries described above were pooled into 3 groups. Pool A contained $X_iCX_jCX_k$ where j=5–7; Pool B contained $X_4CX_2GPX_4CX_4$, $X_{20}$ and $X_iCX_jCX_k$ where j=4; Pool E contained $X_iCX_jCX_k$ where j=8–10. Phage from each pool were incubated with the immobilized targets in Sorting Buffer for 3 h at 25° C.; generally about $5\times10^{10}$ phage were added at the beginning of each round. Unbound phage were removed by repetitive washing with Wash Buffer (50 mM HEPES, pH7.2, 150 mM NaCl, 0.005% Tween 20); remaining phage were eluted with 500 mM KCl, 10 mM HCl, pH2. The eluted phage were then propagated in XL1-Blue cells with VCSM13 helper phage (Stratagene) overnight at 37° C. Enrichment could be monitored by titering the number of phage which bound to a target coated well compared to a well coated with BSA.

FX Activation Assay—Activation of FX by TF-FVIIa was monitored at room temperature as a function of peptide concentration. Each assay sample contained 100 μl of 460 pM relipidated $TF_{1-243}$ ($TF_{PC}$) (Kelley, R. F. et al. (1997) Blood 89:3219–3227) and 30 pM FVIIa in HBS/Ca buffer (20 mM HEPES, pH 7.4, 5 mM $CaCl_2$, 150 mM NaCl, 0.1% PEG 8000); after 20 min, 25 μl of peptide diluted in HBS/Ca Buffer was added. Following a 30 min incubation the reaction was initiated by the addition of 25 μl of 1 μM FX in HBS/Ca (Note: this yields a final concentration of 306 pM $TF_{PC}$, 20 pM FVIIa, and 166 nM FX). For kinetic analysis, the final concentration of FX was varied from between 20 and 500 nM. Aliquots of 25 μl were removed at 1, 3, 5, 7 and 9 min and quenched in 25 μl of 50 mM EDTA. The FXa generated in each aliquot could be measured by the addition of 100 μl of 250 nM Spectrozyme fXa (American Diagnostica), 50 mM Tris, pH 8, 50 mM NaCl, 0.0025% Triton X-100. The rate of FXa generated at each peptide concentration was proportional to the initial slope of the absorbance at 405 nm vs. time. Sigmoidal curves were fit to a four parameter equation by nonlinear regression analysis (Marquardt, J. Soc. Indust. Appl. Math. 11:431–441 (1963); the concentration of each peptide required to give a half-maximal signal in the assay was calculated from the curves and is referred to as the $IC_{50}$ value.

Clotting Assays—Prothrombin time (PT) and activated partial thromboplastin time (APTT) clotting time assays were performed in citrated pooled normal plasmas (human or various animal species). Clotting times were determined using an ACL 300 Automated Coagulation Analyzer (Coulter Corp., Miami, Fla.) and commercially available reagents as follows.

For the PT assay, aqueous solutions of inhibitor at various concentrations were added to citrated pooled normal plasma in a ratio of 1 part inhibitor to 9 parts plasma. Following a 30 min incubation, these mixtures were added to sample cups of an ACL 300 Analyzer. Innovin® (Dade International Inc., Miami, Fla.), a mixture of human relipidated tissue factor and $Ca^{2+}$ ions was added to the reagent cup. Precise volumes of sample and Innovin® (50 µl sample, 100 µl Innovin) were automatically transferred to cells of an acrylic rotor pre-equilibrated to 37° C. Following a 2 min incubation period, coagulation was initiated by mixing the two components by centrifugation. Coagulation was monitored optically and clotting time was reported in seconds. In this system, the clotting time of control plasmas (plasma plus inhibitor diluent) was typically 8 to 10 seconds. The fold prolongation is the clotting time of the inhibitor relative to the clotting time of the control.

For the APTT assay, inhibitor and plasma were mixed together and transferred to the ACL 300 Analyzer sample cups as described above. Actin FS® and $CaCl_2$ (Dade International Inc., Miami, Fla.), were added to reagent cups 1 and 2 respectively. Precise volumes of sample (53 µl) and Actin FS® (53 µl) were automatically transferred to cells of a rotor pre-equilibrated at 37° C. and mixed by centrifugation. Following a 2 min. activation period, coagulation was initiated by the addition of $CaCl_2$ (53 µl). Coagulation was monitored optically and clotting time was reported in seconds. APTT of plasma controls was typically 12 to 32 seconds, depending on the species of plasma used in the assay. The fold prolongation was the clotting time of the inhibitor relative to the clotting time of the control.

Phage ELISA—The ability of peptides to compete with peptide-phage for binding to TF-FVIIa was monitored using a phage ELISA. Dilutions of peptide in Sorting Buffer were added to microtiter plates coated with the TF-FVIIa complex (as described above) for 30 min. Approximately $10^{11}$ monovalent phage displaying the TF74 peptide sequence were then added for an additional 15 min. The microtiter plate was washed with Wash Buffer and the phage bound to FVIIa were detected with an anti-gVIII/HRP monoclonal antibody conjugate (HRP/Anti-M13 Conjugate, Pharmacia Amersham Biotech). The amount of HRP bound was measured using $ABTS/H_2O_2$ substrate and monitoring the absorbance at 405 nm. The absorbance at 405 nm was plotted versus the concentration of peptide originally added to the well. Sigmoidal curves were fit to a four parameter equation by nonlinear regression analysis (Marquardt, J. (1963) Soc. Indust. Appl. Math. 11:431–441; the concentration of each peptide required to give a half-maximal signal in the assay was calculated from the curves and is referred to as the $IC_{50}$ value.

Partial and Complete Randomization on Monovalent Phage—Monovalent libraries which display a single copy of a peptide on the surface of phage fused through a linker sequence to the tail protein coded for by gIII were constructed using single-stranded template-directed mutagenesis (Kunkel T. A. et al. (1991) Methods Enzymol. 204:125–139) of the phagemid t4.g3. Phagemid t4.g3 is a derivative of pA4G32 (Dennis M. S. and Lazarus, R. A. (1994) J. Biol. Chem. 269:22129–22136) where the coding sequence for APPI fused to gIII has been replaced by a 60 bp spacer fused in frame to a linker sequence and gIII, in addition, the $CMP^r$ gene has been inserted into a unique hincII site in the $AMP^r$ gene. The change in drug resistance was designed to eliminate contamination by related although weaker affinity polyvalent clones which could take over the population through avidity effects (Cwirla, S. A. et al. (1990) Proc. Natl. Acad. Sci USA 87:6378–6381). Partially randomized libraries were designed to maintain a bias towards the peptide sequences identified from the initial polyvalent libraries while allowing a 50% mutation rate at each amino acid position. This mutation rate was attained by synthesizing the oligos with a 70-10-10-10 mixture of bases (where each base in the doped region of the oligo is coupled using a mixture containing 70% of the base contributing to wild-type sequence and 10% each of the other 3 bases). In contrast, complete randomization in libraries was obtained by synthesizing oligos using NNS for particular codons in order to fully randomize portions of a displayed peptide while keeping other portions of the sequence constant.

Peptide Synthesis—Peptides were synthesized by either manual or automated (Perceptive Pioneer) Fmoc-based solid phase synthesis on a 0.25 mmol scale using a PEG-polystyrene resin (Bodansky, M. (1984) Principles of Peptide Synthesis, Springer, Berlin). Coupling of each amino acid was accomplished with 2-(H-Benzotriazole-1-yl)-1,1,3,3-tetramethyluronium hexafluorophosphate (HBTU) and N-Hydroxybenzotriazole (HOBt) with diisopropylethylamine (DIPEA) in dimethylacetamide (DMA). Peptides ending in a carboxy-terminal amide were prepared on Rink amide resin. Acetylation of the amino terminus was accomplished with acetic anhydride in 10% triethylamine in dichloromethane. Side chain protecting groups were removed and the peptide was cleaved from the resin with 95% trifluoroacetic acid (TFA) and 5% triisopropylsilane. A saturated iodine solution in acetic acid was added to oxidize the disulfide bonds. Peptides were purified by reversed-phase HPLC using a water/acetonitrile gradient containing 0.1% TFA and lyophilized. Peptides were >95% pure by analytical HPLC and their identity was verified by mass spectrometry.

Biotinylated Peptides—Peptides were synthesized using methods as described above. Peptides containing a carboxy-terminal biotin (e.g. TF147b) were prepared on Fmoc-L-Lysine(ε-Aloc)-PEG polystyrene Rink amide resin. Coupling of each amino acid was accomplished as described above. At the completion of chain assembly the ε-side chain protecting group of lysine was unmasked with Pd°. Fmoc-aminocaproic acid was coupled, deprotected, and then coupled to biotin as described above (Kates, S. A., de la Torre, B. G., Eritja, R., and Albericio, F. (1994) Tetrahedron Lett. 35:1003).

FVIIa Binding ELISA—The ability of peptides to compete with biotinylated versions of TF76 (e.g. TF147b, or other peptides described herein that could be biotinylated as described) for binding to FVIIa was monitored using a FVIIa Binding ELISA or a TF-FVIIa Binding ELISA. Microtiter plates were coated overnight with 2 µg/ml recombinant human FVIIa or 2 µg/ml $TF_{1-243}$ (Paborsky, L. R. et al. (1991) J. Biol. Chem. 266: 21911) in 50 mM ammonium bicarbonate pH 9 at 4° C.; all other steps were performed at room temperature. Plates were then blocked with 1% BSA in Assay Buffer (50 mM HEPES, pH 7.2, 5 mM $CaCl_2$, 150 mM NaCl). For the TF-FVIIa ELISA, recombinant human FVIIa (2 µg/ml) in 1% BSA in Assay Buffer was added for 30 min to the wells previously coated and blocked with TF to form the TF-FVIIa complex. Dilutions of peptide in Assay Buffer plus 0.05% Tween 20 were added to the microtiter plate along with 20 nM TF147b for 1 h. The microtiter plate was washed 3 times with Assay Buffer plus 0.05% Tween 20 and the biotinylated-peptide bound was detected with a Streptavidin/HRP conjugate (Streptavidin-POD, Roche Molecular Biochemicals). The amount of HRP bound was measured using ABTS/$H_2O_2$ substrate (Kirkegaard and Perry Laboratories) and monitoring the absorbance at 405 nm. The absorbance at 405 nm was plotted versus the concentration of peptide originally added to the well. Sigmoidal curves were fit to a four parameter equation by nonlinear regression analysis (Marquardt, J. Soc. Indust. Appl. Math. 11:431–441 (1963); the concentration of each peptide required to give a half-maximal signal in the assay was calculated from the curves and is referred to as the $IC_{50}$ value.

Screening Assay Using the FVIIa Binding ELISA—The FVIIa Binding ELISA described above can also be used to screen for any compound that would block peptides of the present invention from binding to FVIIa. This could be carried out as described above or modified as described below. Thus, a competitive binding assay was established for use in high-throughput screening of chemical libraries for the purpose of identifying inhibitors of peptide binding. The assay is performed in opaque white, high-binding, 384-well plates coated with 1 μg/ml FVIIa and blocked with BSA. Sample, control, or assay buffer (20 μl) and biotinylated peptide (e.g. TF147b or other peptides described herein that could be biotinylated as described) (20 μl) are added to each well, and the plates are incubated for 1 h at room temperature. Sample or control may compete with the biotinylated peptide for binding to the factor VIIa on the plate. The unbound biotinylated peptide is removed by washing the plate six times, and 40 μl of streptavidin-europium are added. During the subsequent 30 min incubation, the streptavidin-europium binds to the biotinylated peptide remaining on the plate. After washing six times to remove the unbound streptavidin-europium, 40 μl of enhancement solution are added to each well to dissociate the europium from the existing nonfluorescent chelate and to replace this with a highly fluorescent chelate. The fluorescence is read on a Wallac Victor microplate reader with excitation at 340 nm and emission at 615 nm following a 100μ second delay. The percent inhibition of binding is calculated relative to controls with assay buffer as sample.

Results

Polyvalent Peptide-Phage that bind to TF-FVIIa— Polyvalent peptide libraries were sorted in 3 pools (designated A, B and E) against immobilized TF-FVIIa. Polyvalent phage display (Scott J. K. and Smith G. P. Science (1990) 249:386–390; Lowman, H. B. (1997) Annu. Rev. Biophys. Biomol. Struct 26:401–424; Wells, J. A. and Lowman, H. B. (1992) Curr. Opin. Biotechnol. 3:355–362) was used to enhance binding through avidity effects. After 4 rounds of selection and amplification, the enrichment for Pool E, the number of phage eluted from a well coated with TF-FVIIa divided by the number of phage eluted from a well coated with BSA, was 1700-fold. The DNA from 12 random clones in each pool were sequenced. The clones in Pool E were all siblings from a single clone with the deduced peptide sequence: EAALCDDPRLDRWYCIFAGE (SEQ ID NO:1); a peptide containing this sequence was designated TF56. Phage bearing this sequence bound specifically to immobilized FVIIa or TF-FVIIa but did not bind to wells coated with either TF or BSA. Additionally, this clone bound to both covalently and noncovalently active site blocked TF-FVIIa, where the active site of FVIIa was alkylated with biotinylated EGR chloromethylketone or blocked by TF7I-C, a Kunitz domain inhibitor (Dennis M. S. and Lazarus, R. A. (1994) J. Biol. Chem. 269:22129–22136), indicating that the peptide bound to FVIIa, but at a site distinct from the active site—an exosite.

Partial Randomization—The initial peptide libraries that were designed, encoded a potential diversity of greater than $20^{20}$ ($10^{26}$) different clones while the actual libraries that were made contained approximately only $10^9$ clones, a very small fraction of the potential diversity. In order to narrow the search and yet further explore the peptide diversity within the area of the initially selected peptides, a partial randomization technique was employed. This technique maintains a bias towards the wildtype sequence while introducing a 50% mutation rate (at the amino acid level) at each amino acid position; thus on average, a phage displayed 20 amino acid peptide would acquire 10 random mutations. In addition, anticipation of further affinity improvements led us to construct these libraries on monovalent phage via fusion to gIII in order to eliminate avidity effects (Lowman, H. B. (1997) Annu. Rev. Biophys. Biomol. Struct 26:401–424; Lowman H. B. et al. (1991) Biochemistry 30: 10832–10838); Wells, J. A. and Lowman, H. B. (1992) Curr. Opin. Biotechnol. 3:355–362).

A monovalent partial randomization library based upon the TF56 sequence (library є3) was constructed and sorted for 4 rounds on TF-FVIIa. Enrichment of 100,000 fold was observed. Again, random clones were selected and sequenced; the deduced peptide sequences are shown in Table I. Several amino acid positions in the TF56 sequence were retained 100% yet multiple codons were observed at many of these positions; wildtype amino acids were still represented at each position reflecting the library design. One notable exception was the absence of L at position 10 suggesting V, I or F were superior replacements at this position. Residues strongly retained following partial randomization may be crucial for binding either through direct contacts or for structural reasons.

TABLE I

| SEQ ID NO: | clone | frequency | Deduced Amino Acid Sequence |
|---|---|---|---|
| 1 | Library E3 | | E A A L C D D P R L D R W Y C I F A G E |
| 65 | EH | 1/12 | E A A L C E D P R V D R W Y C I F A G E |
| 66 | EL | 1/12 | E S A L C D D P R V D R W Y C I F A G D |
| 2 | EB | 2/12 | E G T L C D D P R I D R W Y C M F S G V |
| 67 | EA | 2/12 | E V A L C S D P R V D R W Y C M F A T D |
| 68 | EC | 2/12 | A A A L C D D P R I D R W Y C S F L G V |

TABLE I-continued

| SEQ ID NO: | clone | frequency | Deduced Amino Acid Sequence |
|---|---|---|---|
| 69 | EG | 1/12 | E A A L C D D P R F D R W Y C T F V G E |
| 70 | FE | 3/12 | E A A L C D D P R V D R W Y C T F V G E |

Peptide sequences were deduced from the DNA sequence of clones obtained after 4 rounds of selection.
The frequency represents the occurrence of each clone among the total number of clones sequenced from the pool.
Underlined residues indicate the wildtype sequence which was partial randomized as described in text.

Full maturation—To complete the affinity maturation, a third set of libraries was constructed which fixed positions that were 100% conserved and fully randomized the remaining positions. In addition, the role of residues flanking the disulfide loop was addressed by constructing libraries with either portions of the amino and carboxy terminal or both missing. Thus, 4 monovalent libraries were constructed and are described in Table II. Enrichment of 100,000-fold was observed by each library by round 4; the sequences from random clones are presented in Table II. Even though these libraries (which fully randomized 9 amino acid positions) were far from complete, a comparison of the 4 libraries demonstrated a clear consensus for the optimum amino acid at each position.

TABLE II

| SEQ ID NO: | clone | Deduced Amino Acid Sequence |
|---|---|---|
|  | Library EΔC | X X X L C X D P R X D R W Y C X F X |
| 71 | EC31 | N R S L C N D P R V D R W Y C N F S |
| 72 | EC32 | Q S R L C D D P R I D R W Y C Q F G |
| 73 | EC33 | E A A L C D D P R I D R W Y C G F L |
| 74 | EC41 | Y Q F L C D D P R I D R W Y C K F V |
| 75 | EC42 | W G T L C D D P R I D R W Y C R F S |
| 76 | EC43 | V K A L C V D P R I D R W Y C Q F T |
|  | Library EΔN | X L C X D P R X D R W Y C X F X X X |
| 77 | EN31 | G L C D D P R V D R W Y C Q F Q V L |
| 78 | EN32 | N L C S D P R V D R W Y C Q F I R — |
| 79 | EN33 | S L C D D P R V D R W Y C G F V E V |
| 80 | EN41 | A L C D D P R V D R W Y C L F V E G |
| 81 | EN42 | A L C H D P R V D R W Y C M F M E D |
| 82 | EN43 | T L C S D P R V D R W Y C R F A E G |
|  | Library EΔNC | X L C X D P R X D R W Y C X F X |
| 83 | ENC31 | T L C A D P R V D R W Y C Q F T |
| 84 | ENC32 | N L C A D P R V D R W Y C K F V |
| 85 | ENC34 | R L C D D P R V D R W Y C Q F G |
| 86 | ENC35 | S L C E D P R V D R W Y C Q F T |
| 87 | ENC42 | T L C E D P R V D R W Y C Q F V |
| 88 | ENC44 | S L C D D P R V D R W Y C Q F A |
| 89 | ENC41 | P L C S D P R V D R W Y C Q F S |
| 90 | ENC43 | S L C M D P R I D R W Y C T F V |
| 91 | ENC45 | T L C D D P R V D R W Y C Q F T |
|  | Library EFL | X X X L C X D P R X D R W Y C X F X X X |
| 92 | EP42 | G E A L C T D P R V D R W Y C Q F H V H |
| 93 | EP43 | Y R S L C S D P R I D R W Y C Q F I G D |
| 94 | EP44 | T G A L C E D P R V D R W Y C A F V E Q |
| 95 | EP45 | M T A L C E D P R V D R W Y C S F M P G |
| 96 | EP41 | V T S L C S D P R V D R W Y C S F L S E |
| 97 | EP31 | G A A L C D D P R V D R W Y C Q F S I G |
| 98 | EP32 | V R A L C E D P R V D R W Y C R F V D I |
| 99 | EP33 | T V A L C E D P R V D R W Y C Q F F E Y |
| 100 | EP34 | I V Q L C D D P R V D R W Y C Q F A K P |
| 101 | EP35 | N G S L C D D P R I D R W Y C G F I E Y |

Peptide sequences were deduced from the DNA sequence of clones obtained after 4 rounds of selection. Shaded residues endicate the wildtype sequence which was fixed, inderlined residues were fully randomized as described in text.

Characterization of Peptides that bind to TF-FVIIa—In order to assess the activity of the sequences selected from the phage displayed libraries, peptides corresponding to sequences selected from these libraries were chemically synthesized. Thus, peptide TF56 (EAALCDDPRLDRWYCIFAGE-NH$_2$) (SEQ ID NO:1), corresponding to a random-phage derived clone from library E3, peptide TF58 (EGTLCDDPRIDRWYCMFSGV) (SEQ ID NO:2), corresponding to a clone derived from the partially randomized library, and TF76 (Ac-ALCDDPRVDRWYCQFVEG-NH$_2$) (SEQ ID NO:8), corresponding to the consensus from the fully matured sequence, were chemically synthesized. Data from these as well as TF74 and TF151 are presented in the Figures.

Although peptides were selected only for binding to the TF-FVIIa complex, we were interested in finding functionally relevant peptides, i.e. peptides that would inhibit the TF-FVIIa catalyzed activation of FX to FXa in a dose dependent manner, by interfering with the binding and/or turnover of FX. Thus they were tested for their ability to inhibit FX activation; the inhibition of FX activation by selected peptides is shown in FIG. 1. The sequences of selected peptides and IC$_{50}$ values for inhibiting FX activation are shown in FIG. 8. In addition, peptides derived later in the maturation process were more potent, demonstrating the effectiveness of this procedure.

Figure 2A:
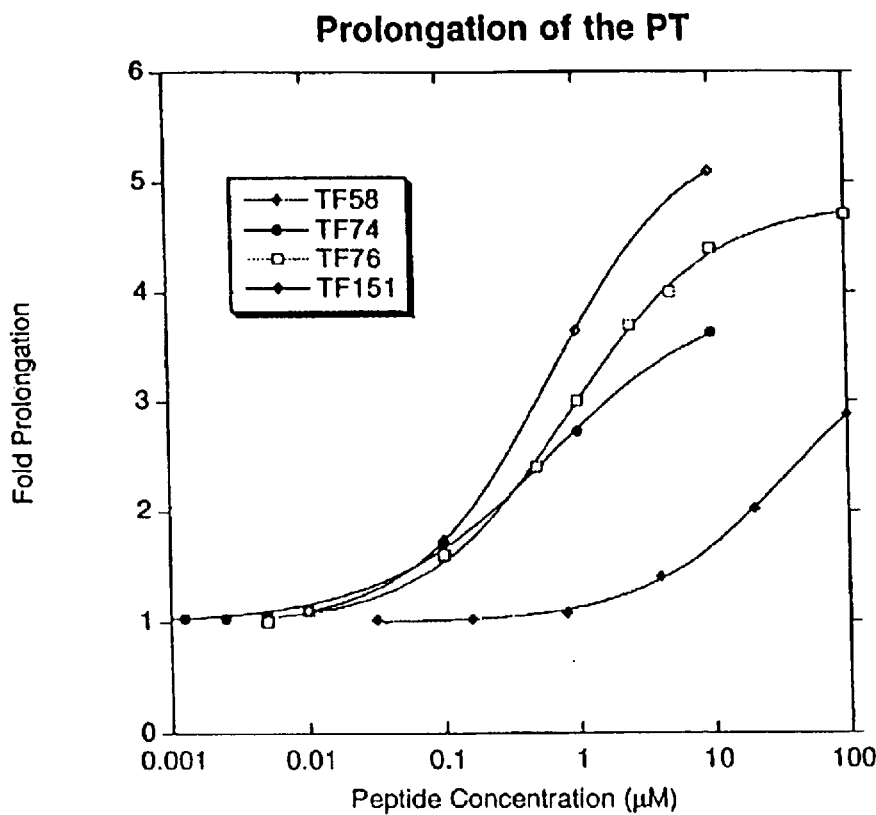
FIGS. 2A and 2B.
Figure 2B:
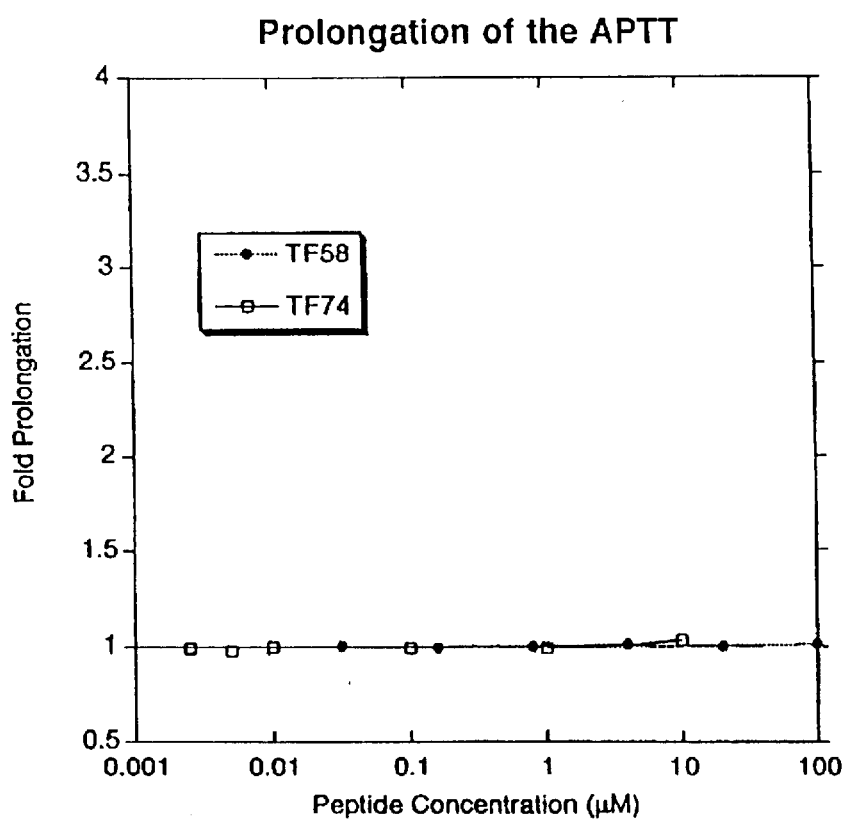

In agreement with their ability to block FX activation using purified components, the peptides described herein were potent anticoagulants. The inhibition of the TF dependent extrinsic clotting pathway in human plasma, as measured by the dose dependent prolongation of the prothrombin time (PT), is shown in FIG. 2A. It is significant that we see no evidence for prolonging the clotting time in human plasma in the surface dependent intrinsic pathway, as determined by the activated partial thromboplastin time (APTT) (FIG. 2B). This implies that the E peptides do not inhibit any of the serine proteases involved in the intrinsic pathway, which include thrombin, FXa, FIXa, FXIa, plasma kallikrein, and FXIIa.

Figure 3:
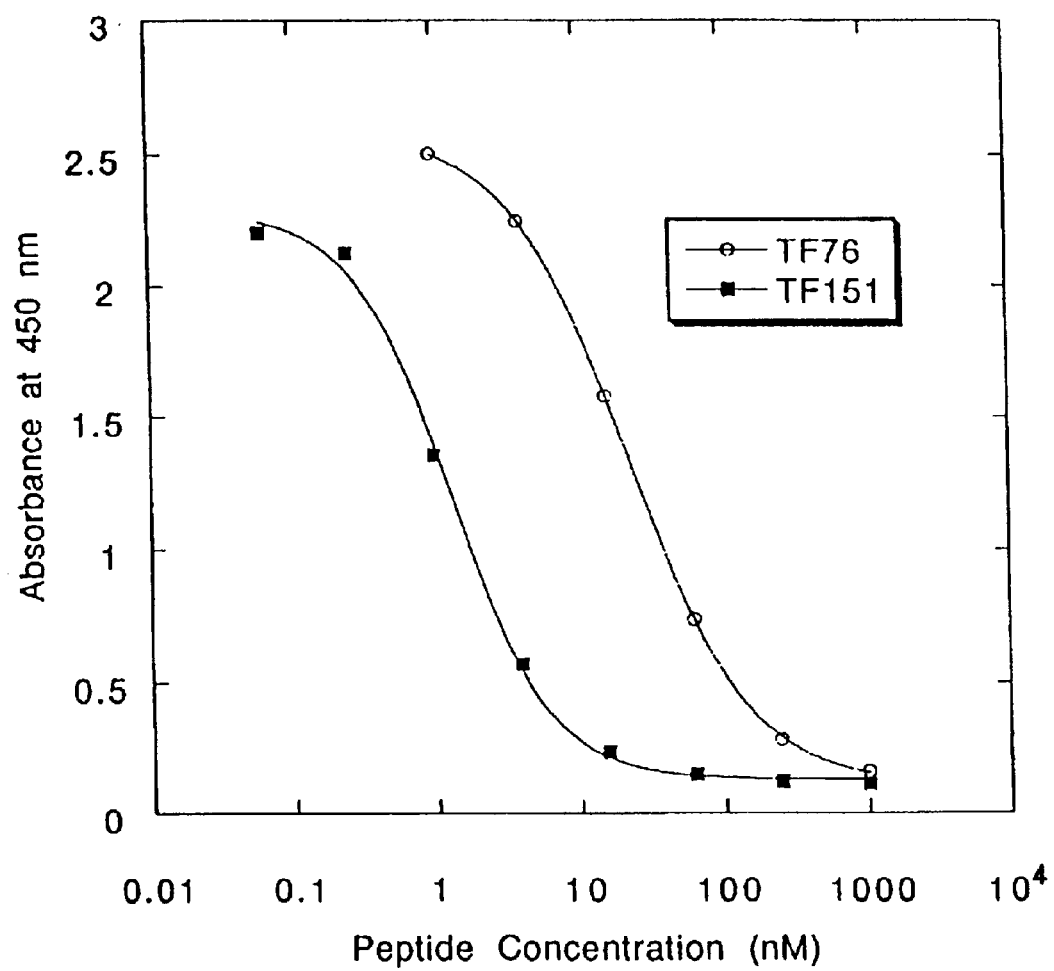
FIG. 3 shows the inhibition of TF147b (SEQ ID NO:40) binding to FVIIa or TF-FVIIa by selected peptides.

FVIIa Binding ELISA—The ability of peptides to compete with a biotinylated version of TF76 (e.g. TF147b or other peptides described herein that could be biotinylated as described) for binding to FVIIa was monitored using a FVIIa Binding ELISA; the inhibition of TF147b binding to FVIIa or TF-FVIIa by selected peptides is shown in FIG. 3. The sequences of selected peptides and the IC$_{50}$ values for their inhibition of the binding of TF147b to either FVIIa or TF-FVIIa is shown in FIG. 8. The FVIIa Binding ELISA can also be used to screen for any compound that would block peptides of the present invention from binding to FVIIa. This could be carried out using a variety of reagents to detect the biotinylated peptide. Furthermore, a variety of peptides described herein could be used to develop the same type of assay. Thus, a competitive binding assay was established for use in high-throughput screening of chemical libraries for the purpose of identifying inhibitors of peptide binding.

Example 2

Expression and Characterization of a Peptide Fusion that Binds FVIIa and Inhibits FX Activation and Clotting Methods Construction of TF151 Fc expression vector—Standard recombinant DNA techniques were used for the construction of recombinant transfer vectors based on the vector pVL1393 (Pharmigen) (Sambrook, J., Fritsch, E. F., and Maniatis, T. (1989) *Molecular Cloning: A Laboratory Manual*, second Ed., Cold Spring Harbor Laboratory Press, New York; O'Reilly, D. R., Miller, L. K., and Luckow, V. A. (1994) *Baculovirus Expression Vectors: A Laboratory Manual*, Oxford University Press, New York). The pVL1393 derived plasmid pbPH.His was linearized with Nco I and Sma I and treated with shrimp alkaline phosphatase (Dwyer, M. A. et al. (1999) J. Biol. Chem. 274:9738–9743). The Fc portion of the human IgG1 was obtained as a 700 base pair fragment by restriction digestion using Nde I and subsequent treatment with Klenow and Nco I of another pVL1393 derived plasmid pVL1393.IgG. The signal sequence for MIP.5 was introduced before the Fc sequence as a PCR fragment digested with EcoR I, included within the fragment is an Asc I site. The Asc I site occurs following the putative signal sequence cleavage site. Following ligation, competent *E. coli* XL-1 Blue were transformed and bacteria were selected for the correct recombinant plasmid (pVL1393.MIP.5sig.Fc) by DNA sequence analysis. Then, pVL1393.MIP.5sig.Fc was linearized with Asc I and Stu I and treated with shrimp alkaline phosphatase. The linearized vector was then ligated with a synthetic piece of DNA with compatible ends. The synthetic DNA inserts were formed by annealing 2 oligos with the sequences: 5'-GCC GGA GCT CCC GCC TCC GCC CTC CAC GAA CTG GCA GTA CCA CCT GTC GAT TCT GGG GTT GTC GCA CAG GGC GCC CAC GG-3' (SEQ ID NO:102) and 5'-CGC GCC GTG GGC GCC CTG TGC GAC AAC CCC AGA ATC GAC AGG TGG TAC TGC CAG TTC GTG GAG GGC GGA GGC GGG AGC TCC GGC-3' (SEQ ID NO:103) coding for peptide sequence TF151 (FIG. 8) including a GGGSSG linker (SEQ ID NO:104). Following ligation, competent *E. coli* XL-1 Blue were transformed and bacteria were selected for the correct recombinant plasmid (termed pVL.1393.MIP5.TF151-Fc) by DNA sequence analysis using the dRhodamine dye-terminator method and an Applied Biosystems ABI Model 373 automated DNA sequencer. Recombinant transfer vector was purified using a Qiagen Mini-Prep and used for construction of recombinant baculovirus.

Recombinant baculovirus, AcNpV.TF151-Fc, was generated following cotransfection of Sf9 cells with the transfer vector and the linearized wild type baculovirus DNA (*Autographa californica* nuclear polyhedrosis virus (AcNpV), Pharmingen). A primary amplification of the recombinant baculovirus, AcNpV.TF151-Fc, achieved detectable protein expression. Subsequent plaque-purification and titering of the viral stock was performed by plaque assays. Standard methods were utilized as previously described (O'Reilly, D. R., Miller, L. K., and Luckow, V. A. (1994) *Baculovirus Expression Vectors: A Laboratory Manual*, Oxford University Press, New York).

Cell Culture—Adherent cultures of *Spodeptera frugiperda* (Sf9) insect cells (ATCC CRL 1711) were maintained at 28° C. in Hink's TNM-FH insect medium supplemented GRACE's (JRH Biosciences, #51942-78P), with glutamine, streptomycin/penicillin, and 10% fetal bovine serum (heat inactivated for 30 min at 56° C.). Cultures were passaged every 3 days. Spinner cultures of High Five™ cells (*Trichoplusia* ni, BT1.TN.SB1-4 (Invitrogen)) (500 ml at 2.0×10$^6$ cells/ml) were infected at a multiplicity of infection of 0.5 and harvested 60 h posttransfection. Suspension cultures were maintained in spinner flasks at 28° C. using ESF-921 protein free insect cell culture medium (Expression Systems LLC, #96-001). Cultures were passaged every 3 days to a starting cell density of 10$^6$ cells/ml.

TF151-Fc Purification—Following the optimized infection protocol, the High Five™ cells were removed by centrifugation at 800×g at 4° C. for 10 min. The clarified supernatant (0.5 L) was filtered using a 0.45µ Nalgene filter and applied to a 0.5 ml Hi-Trap Protein A Column (Amersham Pharmacia Biotech) equilibrated with PBS (phosphate buffered saline) at 25° C. After washing with 20 ml of PBS, the column was eluted with 3 ml of 0.2 N HOAc and fractions containing TF151-Fc were lyophilized and stored at 4° C.

SDS-PAGE—Samples were analyzed reduced and unreduced on a 4–20% Tris-glycine SDS-PAGE (Novex) along with prestained protein molecular weight markers (SeaBlue, Novex) using the method of Laemmli (Laemmli, U. K. (1970) Nature 227:680–685).

Protein Sequencing—TF151-Fc purified from the infected Sf9 cell supernatants was subjected to SDS-PAGE, and then transferred to a PVDF membrane. Electroblotting onto Millipore Immobilon-PSQ membranes was carried out for 1 h at 250 mA constant current in a BioRad Trans-Blot transfer cell (Matsudaira, P. (1987) J. Biol. Chem. 262: 10035–10038). The PVDF membrane was stained with 0.1% Coomassie Blue R-250 in 50% methanol, 0.5 min and destained for 2–3 min with 10% acetic acid in 50% methanol. The membrane was thoroughly washed with water and allowed to dry before storage at −20° C. The TF151-Fc band at about 50 kD was cut out and the first 11 residues were sequenced using a model 494A Applied Biosystems sequencer equipped with an on-line PTH analyzer. Peaks were integrated with Justice Innovation software using Nelson Analytical 760 interfaces. Sequence interpretation was performed on a DEC alpha (Henzel, W. J., Rodriguez, H., and Watanabe, C. (1987) J. Chromatog. 404: 41–52).

FVIIa Binding ELISA—The ability of TF151-Fc to compete with TF147b a biotinylated version of TF76, (FIG. 8) for binding to FVIIa was monitored using a FVIIa Binding ELISA. Microtiter plates were coated overnight with 2 µg/ml recombinant human FVIIa in 50 mM ammonium bicarbonate pH 9 at 4° C.; all other steps were performed at room temperature. Plates were then blocked with 1% BSA in Assay Buffer (50 mM HEPES, pH 7.2, 5 mM $CaCl_2$, 150 mM NaCl). Dilutions of TF151-Fc in Assay Buffer plus 0.05% Tween 20 were added to the microtiter plate along with 20 nM TF147b for 1 h. The microtiter plate was washed 3 times with 300 µl Assay Buffer plus 0.05% Tween 20 and the TF147b bound was detected with a Streptavidin/HRP conjugate (Streptavidin-POD, Roche Molecular Biochemicals). The amount of HRP bound was measured using $ABTS/H_2O_2$ substrate (Kirkegaard and Perry Laboratories) and monitoring the absorbance at 405 nm. The absorbance at 405 nm was plotted versus the concentration of peptide originally added to the well. Sigmoidal curves were fit to a four parameter equation by nonlinear regression analysis (Marquardt, J. Soc. Indust. Appl. Math. 11:431–441 (1963); the concentration of TF151-Fc required to give a half-maximal signal in the assay was calculated from the curves and is referred to as the $IC_{50}$ value.

FX Activation Assay—The FX activation assay was carried out as described in Example 1.

Clotting Assays—The PT clotting assay was carried out as described in Example 1.

Results

Figure 4:
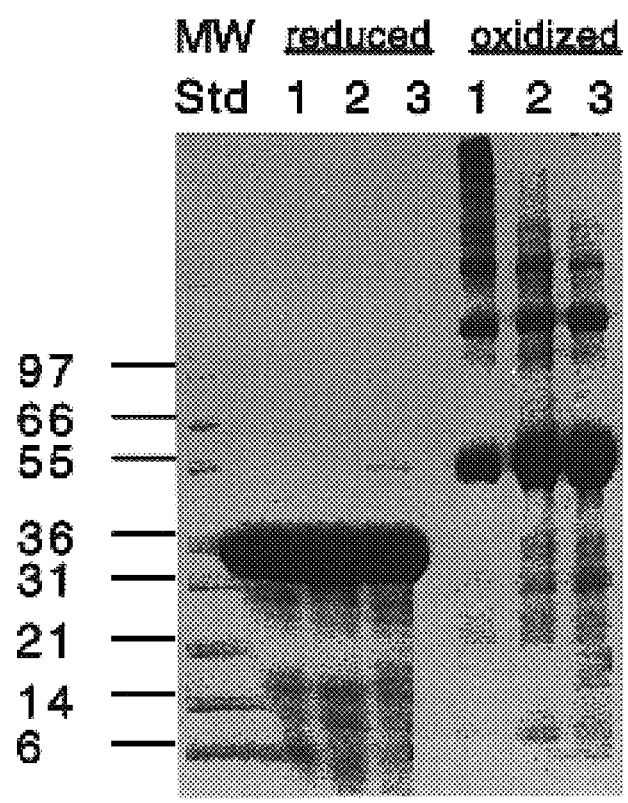
FIG. 4 shows SDS-PAGE analysis of the reduced and unreduced TF151-Fc fusion revealing bands at about 30 and about 60 kDa respectively, suggesting association of two peptide-Fc monomers to form a dimer.

Protein Characterization of TF151-Fc—Following purification, approximately 8 mg of control-Fc (an Fc lacking a fused peptide ligand) or TF151-Fc was obtained from a 500 ml culture. SDS-PAGE analysis of the reduced and unreduced fusions revealed bands at about 30 and about 60 kDa respectively, suggesting the association of two peptide-Fc monomers to form a dimer (FIG. 4). N-terminal sequence analysis of TF151-Fc revealed the sequence 'SQAQRRA VGAL . . . ' (SEQ ID NO:43) indicating removal of the signal sequence and expression of the peptide as a fusion to the Fc.

Figure 5:
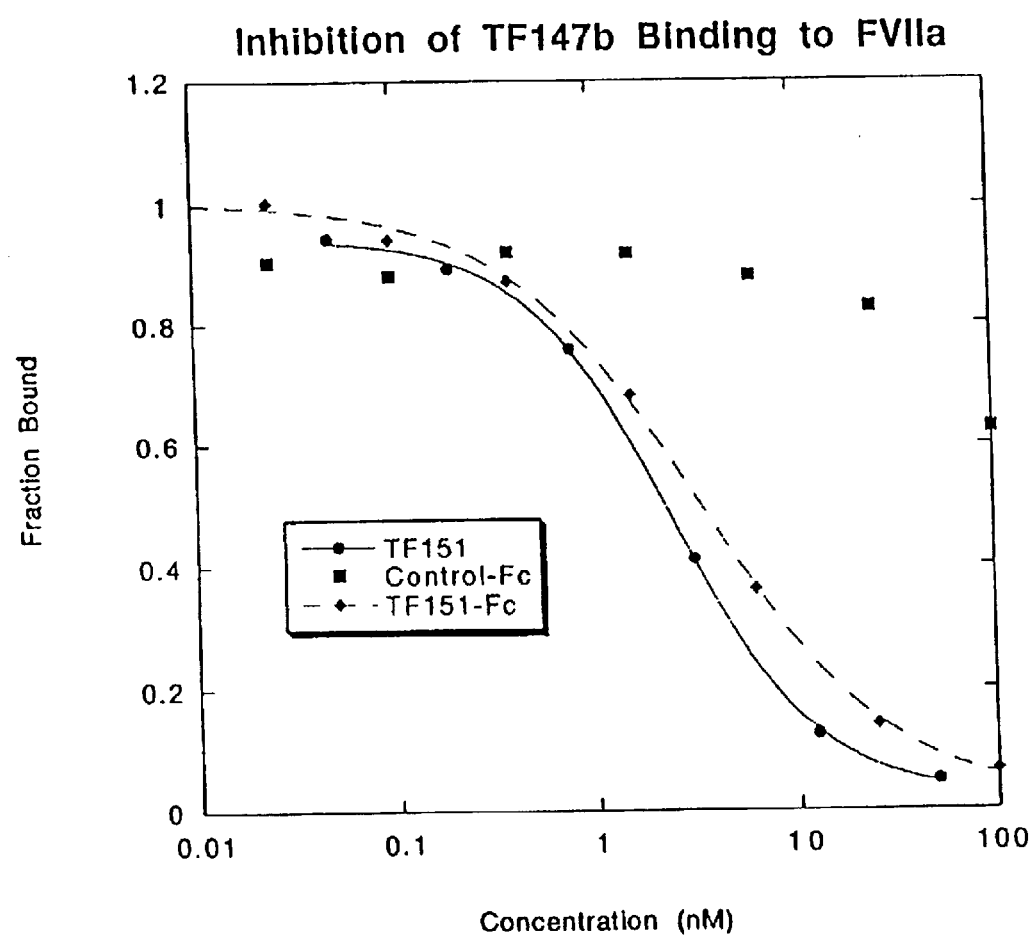
FIG. 5 shows the inhibition of TF147b binding to FVIIa by the TF151-Fc fusion is comparable to TF151.
Figure 6:
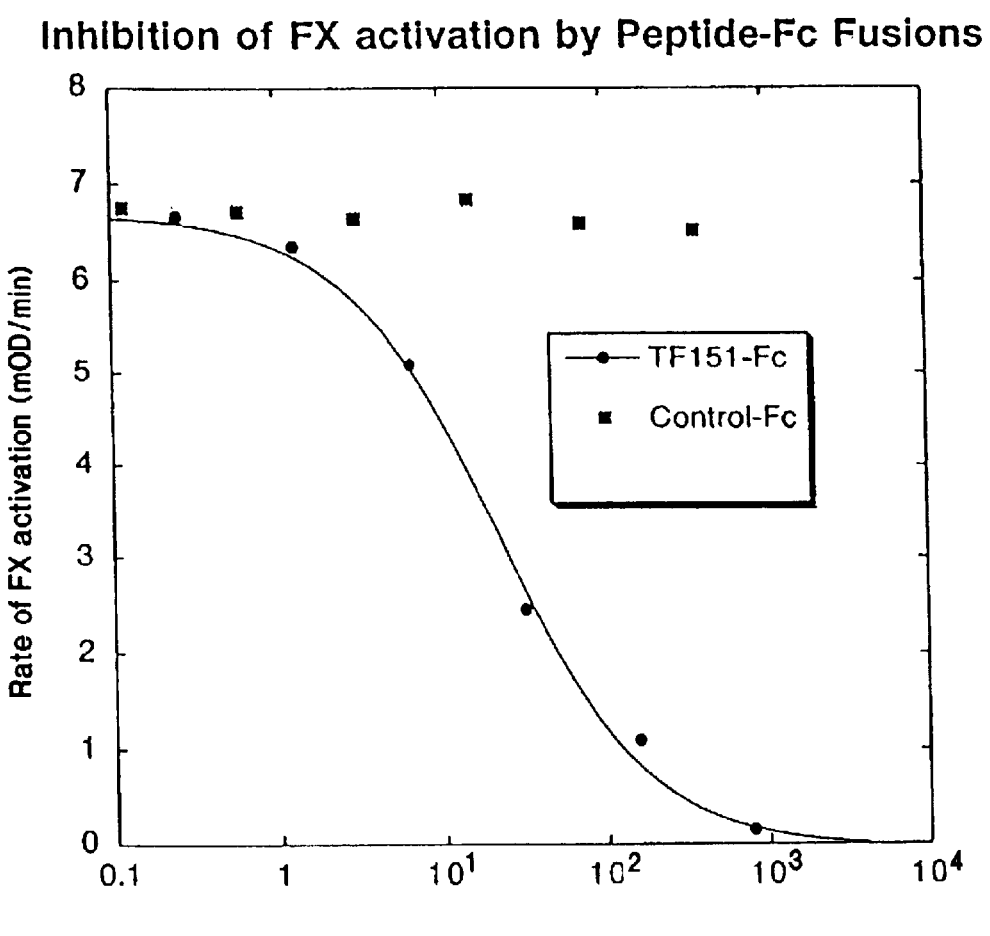
FIG. 6 shows that the TF151-Fc fusion is capable of inhibiting FX activation by TF-FVIIa in a FX activation assay.
Figure 7:
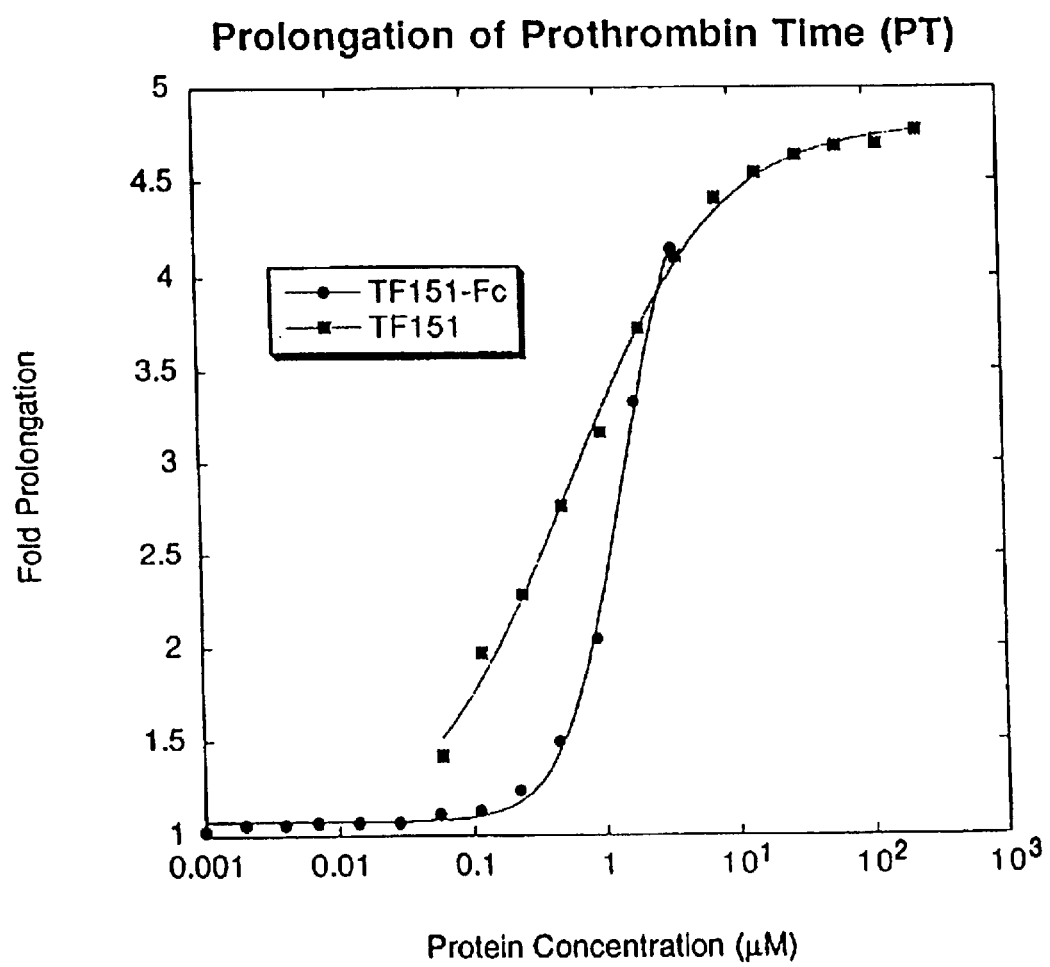
FIG. 7 shows the prolongation of the prothrombin time in human plasma with the TF151-Fc fusion and TF151.

TF151-Fc Activity—The ability of TF151-Fc to compete with TF147b a biotinylated version of TF76 for binding to FVIIa was monitored using a FVIIa Binding ELISA. The inhibition of TF147b binding to FVIIa was comparable to peptide TF151 and is shown in FIG. 5; TF151 and the TF151-Fc fusion had $IC_{50}$ values of 2 and 3 nM, respectively. The TF151-Fc fusion was also comparable to the peptide TF151 in its ability to inhibit FX activation by TF-FVIIa in a FX activation assay (FIG. 6). The ability to block FX activation with TF151-Fc was also reflected in the prolongation of the prothrombin time in human plasma (FIG. 7). The potency of TF151-Fc was comparable to peptide TF151 in this assay.

Example 3

Purification, Crystalization and Structure Determination for TF76 (SEQ ID NO: 8)

Peptide TF76 was synthesized as previously described (Lowman, H. B., et al. Molecular mimics of insulin-like growth factor 1 (IGF-1) for inhibiting IGF-1: IGF-binding protein interactions. Biochemistry 37, 8870–8878 (1998)). Acetylation of the amino terminus was accomplished with acetic anhydride in 10% triethylamine in dichloromethane.

Harvested cell culture medium from 293 cells expressing human Factor VII was treated with 5 mM EDTA and 2 mM benzamidine and loaded onto a DEAE Fast Flow column; bound FVII was eluted with 150 mM NaCl. The DEAE pool was loaded onto a Q-Sepharose Fast Flow column and eluted with 5 mM CaCl2, 135 mM NaCl. The Q-Sepharose pool eluted as activated FVIIa and was concentrated by ammonium sulfate precipitation. Solubilized FVIIa was passed over a Sephacryl-200 gel filtration column; N-terminal sequence analysis confirmed the loss of the Gla domain (proteolysis between Trp 41 and Ile 42). TF76 and Gla-domainless FVIIa, covalently active-site inhibited with D-Phe-L-Phe-Arg-chloromethyl ketone (D-FFRCMK) were combined in a 1:1 ratio and purified on a Superdex 75 column. Crystals grew from hanging drops equilibrated against 20% (w/v) PEG 4000, 10% t-butyl alcohol, 0.1 M sodium cacodylate pH 5.5, were harvested into a cryoprotectant solution containing reservoir with 10% methylpentanediol, and flash frozen in liquid nitrogen. Data extending to 3 Å were collected on a MAR345 scanner in space group P21 with a=70.49 Å, b=55.26 Å, c=111.73 Å, b=99.48° at SSRL beamline 9.1, with average redundancy 2.6, reduced with Mosflm and processed with the CCP4 suite (Rmerge=10.4%, 26.2% in the outer shell; overall I/s=6.2, 2.7 in the outer shell; completeness 97.7%, 98.6% in the outer shell). Solution was by molecular replacement (Amore) using parts of the TFoFVIIa structure (Banner, D. W., et al. The crystal structure of the complex of blood coagulation factor VIIa with soluble tissue factor. Nature 380, 41–46 (1996)). Refinement and model adjustment were performed with X-PLOR v3.851and Xsight (Molecular Simulations Inc.). Non-crystallographic restraints were applied to the two complexes in the crystallographic asymmetric unit (rmsd=0.44 Å).

Statistics for Data Collection and Refinement

| | |
|---|---|
| Refinement resolution (Å) | 50.0–3.0 |
| Number of relections | 16915 |
| Number of relections (R-free) | 654 |
| R-value | 22.5% |
| R-free | 29.5% |
| R-value (all) | 22.8% |
| rmsd bond distances (Å) | 0.012 |
| rmsd bond angles (°) | 2.0 |
| rmsd dihedral angles (°) | 26.3 |
| rmsd improper dihedral angles (°) | 0.82 |
| Number of atoms | 5919 |
| Number of atoms occupancy zero | 381 |
| Number of residues | 756 |
| Number of waters | 4 |

-continued

| | |
|---|---|
| Number of calcium ions | 4 |
| Number of cacodylate ions | 2 |
| rmsd main chain B-factors (Å2) | 3.2 |
| rmsd side chain B-factors (Å2) | 5.0 |
| Ramachandran plot | |
| residues in most favorable region (%) | 75.8 |
| nonglycine residues in disallowed regions (%) | 0.0 |

Results

Figure 9:
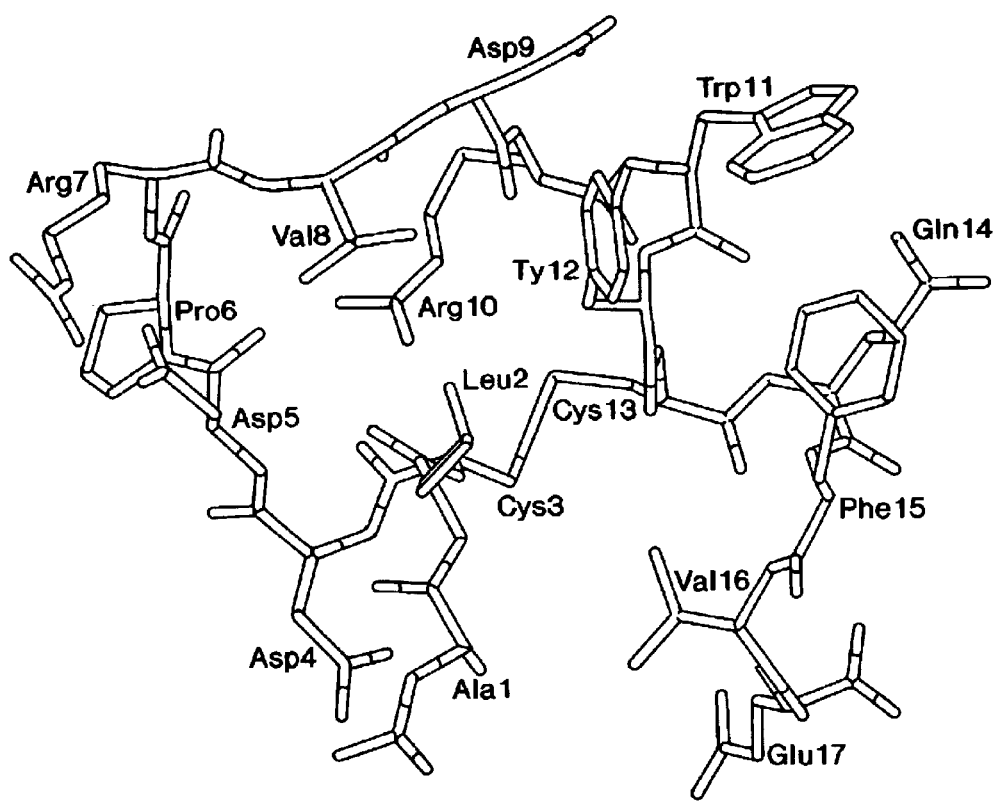
FIG. 9: Structure of TF76 (SEQ ID NO: 8).

The three-dimensional coordinates of the residues belonging to TF76 are listed in Table III. FIG. 9 shows the corresponding three dimensional structure.

TABLE III

| | | | | | X | Y | Z | Q | B |
|---|---|---|---|---|---|---|---|---|---|
| HETATM | 2771 | C | ACE X | 0 | 47.255 | 4.812 | 3.830 | 1.00 | 53.97 |
| HETATM | 2772 | O | ACE X | 0 | 47.964 | 5.744 | 3.440 | 1.00 | 59.91 |
| HETATM | 2773 | CH3 | ACE X | 0 | 47.834 | 3.531 | 4.390 | 1.00 | 58.28 |
| ATOM | 2774 | N | ALA X | 1 | 45.937 | 4.822 | 3.811 | 1.00 | 46.68 |
| ATOM | 2775 | CA | ALA X | 1 | 45.118 | 5.891 | 3.289 | 1.00 | 42.60 |
| ATOM | 2776 | C | ALA X | 1 | 44.432 | 4.967 | 2.313 | 1.00 | 43.82 |
| ATOM | 2777 | O | ALA X | 1 | 45.082 | 4.091 | 1.746 | 1.00 | 46.46 |
| ATOM | 2778 | CB | ALA X | 1 | 45.941 | 6.936 | 2.541 | 1.00 | 41.30 |
| ATOM | 2779 | N | LEU X | 2 | 43.134 | 5.121 | 2.126 | 1.00 | 39.56 |
| ATOM | 2780 | CA | LEU X | 2 | 42.426 | 4.229 | 1.241 | 1.00 | 35.42 |
| ATOM | 2781 | C | LEU X | 2 | 42.764 | 4.536 | −0.215 | 1.00 | 35.86 |
| ATOM | 2782 | O | LEU X | 2 | 42.872 | 3.628 | −1.039 | 1.00 | 33.01 |
| ATOM | 2783 | CB | LEU X | 2 | 40.917 | 4.331 | 1.515 | 1.00 | 34.51 |
| ATOM | 2784 | CG | LEU X | 2 | 40.385 | 3.758 | 2.845 | 1.00 | 26.75 |
| ATOM | 2785 | CD1 | LEU X | 2 | 39.296 | 2.764 | 2.576 | 1.00 | 25.71 |
| ATOM | 2786 | CD2 | LEU X | 2 | 41.481 | 3.055 | 3.602 | 1.00 | 26.42 |
| ATOM | 2787 | N | CYS X | 3 | 42.972 | 5.811 | −0.525 | 1.00 | 38.67 |
| ATOM | 2788 | CA | CYS X | 3 | 43.296 | 6.214 | −1.897 | 1.00 | 41.34 |
| ATOM | 2789 | C | CYS X | | 44.497 | 5.411 | −2.414 | 1.00 | 41.10 |
| ATOM | 2790 | O | CYS X | 3 | 44.523 | 4.997 | −3.570 | 1.00 | 41.41 |
| ATOM | 2791 | CB | CYS X | 3 | 43.559 | 7.746 | −1.949 | 1.00 | 41.81 |
| ATOM | 2792 | SG | CYS X | 3 | 43.887 | 8.582 | −3.563 | 1.00 | 38.88 |
| ATOM | 2793 | N | ASP X | 4 | 45.480 | 5.179 | −1.557 | 1.00 | 36.60 |
| ATOM | 2794 | CA | ASP X | 4 | 46.654 | 4.434 | −1.956 | 1.00 | 35.33 |
| ATOM | 2795 | C | ASP X | 4 | 46.313 | 3.116 | −2.657 | 1.00 | 38.61 |
| ATOM | 2796 | O | ASP X | 4 | 47.090 | 2.631 | −3.477 | 1.00 | 42.35 |
| ATOM | 2797 | CB | ASP X | 4 | 47.506 | 4.134 | −0.728 | 1.00 | 33.86 |
| ATOM | 2798 | CG | ASP X | 4 | 48.134 | 5.375 | −0.138 | 1.00 | 35.78 |
| ATOM | 2799 | OD1 | ASP X | 4 | 47.950 | 6.467 | −0.721 | 1.00 | 34.64 |
| ATOM | 2800 | OD2 | ASP X | 4 | 48.814 | 5.255 | 0.910 | 1.00 | 36.48 |
| ATOM | 2801 | N | ASP X | 5 | 45.144 | 2.551 | −2.358 | 1.00 | 37.77 |
| ATOM | 2802 | CA | ASP X | 5 | 44.728 | 1.262 | −2.923 | 1.00 | 35.76 |
| ATOM | 2803 | C | ASP X | 5 | 44.020 | 1.318 | −4.278 | 1.00 | 38.42 |
| ATOM | 2804 | O | ASP X | 5 | 42.927 | 1.882 | −4.411 | 1.00 | 41.77 |
| ATOM | 2805 | CB | ASP X | 5 | 43.853 | 0.541 | −1.898 | 1.00 | 38.54 |
| ATOM | 2806 | CG | ASP X | 5 | 43.448 | −0.836 | −2.343 | 1.00 | 40.25 |
| ATOM | 2807 | OD1 | ASP X | 5 | 43.236 | −1.015 | −3.563 | 1.00 | 45.94 |
| ATOM | 2808 | OD2 | ASP X | 5 | 43.334 | −1.731 | −1.471 | 1.00 | 38.72 |
| ATOM | 2809 | N | PRO X | 6 | 44.613 | 0.677 | −5.290 | 1.00 | 40.15 |
| ATOM | 2810 | CA | PRO X | 6 | 44.071 | 0.644 | −6.648 | 1.00 | 40.82 |
| ATOM | 2811 | C | PRO X | 6 | 42.650 | 0.133 | −6.843 | 1.00 | 41.06 |
| ATOM | 2812 | O | PRO X | 6 | 41.946 | 0.562 | −7.766 | 1.00 | 44.99 |
| ATOM | 2813 | CB | PRO X | 6 | 45.065 | −0.210 | −7.418 | 1.00 | 41.37 |
| ATOM | 2814 | CG | PRO X | 6 | 46.330 | −0.191 | −6.622 | 1.00 | 42.24 |
| ATOM | 2815 | CD | PRO X | 6 | 45.874 | −0.080 | −5.185 | 1.00 | 44.75 |
| ATOM | 2816 | N | ARG X | 7 | 42.187 | −0.761 | −5.990 | 1.00 | 40.35 |
| ATOM | 2817 | CA | ARG X | 7 | 40.841 | −1.268 | −6.236 | 1.00 | 43.82 |
| ATOM | 2818 | C | ARG X | 7 | 39.748 | −0.453 | −5.568 | 1.00 | 44.18 |
| ATOM | 2819 | O | ARG X | 7 | 38.647 | −0.958 | −5.328 | 1.00 | 47.84 |
| ATOM | 2820 | CB | ARG X | 7 | 40.749 | −2.774 | −5.895 | 1.00 | 38.71 |
| ATOM | 2821 | CG | ARG X | 7 | 40.594 | −3.127 | −4.437 | 1.00 | 38.07 |
| ATOM | 2822 | CD | ARG X | 7 | 41.638 | −4.143 | −3.958 | 1.00 | 35.16 |
| ATOM | 2823 | NE | ARG X | 7 | 41.911 | −3.887 | −2.540 | 1.00 | 38.09 |
| ATOM | 2824 | CZ | ARG X | 7 | 41.762 | −4.770 | −1.550 | 1.00 | 37.97 |
| ATOM | 2825 | NH1 | ARG X | 7 | 41.325 | −5.999 | −1.799 | 1.00 | 33.83 |

TABLE III-continued

|  |  |  |  |  | X | Y | Z | Q | B |
|---|---|---|---|---|---|---|---|---|---|
| ATOM | 2826 | NH2 | ARG X | 7 | 41.999 | −4.403 | −0.290 | 1.00 | 35.94 |
| ATOM | 2827 | N | VAL X | 8 | 40.051 | 0.822 | −5.305 | 1.00 | 44.03 |
| ATOM | 2828 | CA | VAL X | 8 | 39.078 | 1.677 | −4.638 | 1.00 | 42.46 |
| ATOM | 2829 | C | VAL X | 8 | 38.430 | 2.792 | −5.431 | 1.00 | 42.88 |
| ATOM | 2830 | O | VAL X | 8 | 39.041 | 3.410 | −6.308 | 1.00 | 46.76 |
| ATOM | 2831 | CB | VAL X | 8 | 39.648 | 2.372 | −3.420 | 1.00 | 40.58 |
| ATOM | 2832 | CG1 | VAL X | 8 | 38.524 | 3.022 | −2.629 | 1.00 | 38.58 |
| ATOM | 2833 | CG2 | VAL X | 8 | 40.395 | 1.387 | −2.558 | 1.00 | 42.72 |
| ATOM | 2834 | N | ASP X | 9 | 37.185 | 3.073 | −5.076 | 1.00 | 39.87 |
| ATOM | 2835 | CA | ASP X | 9 | 36.461 | 4.142 | −5.702 | 1.00 | 40.27 |
| ATOM | 2836 | C | ASP X | 9 | 37.377 | 5.323 | −5.573 | 1.00 | 42.07 |
| ATOM | 2837 | O | ASP X | 9 | 37.848 | 5.601 | −4.478 | 1.00 | 46.36 |
| ATOM | 2838 | CB | ASP X | 9 | 35.204 | 4.443 | −4.936 | 1.00 | 38.97 |
| ATOM | 2839 | CG | ASP X | 9 | 34.502 | 5.629 | −5.487 | 1.00 | 43.15 |
| ATOM | 2840 | OD1 | ASP X | 9 | 35.014 | 6.222 | −6.470 | 1.00 | 44.50 |
| ATOM | 2841 | OD2 | ASP X | 9 | 33.441 | 5.964 | −4.943 | 1.00 | 46.21 |
| ATOM | 2842 | N | ARG X | 10 | 37.599 | 6.044 | −6.661 | 1.00 | 41.77 |
| ATOM | 2843 | CA | ARG X | 10 | 38.523 | 7.162 | −6.599 | 1.00 | 45.64 |
| ATOM | 2844 | C | ARG X | 10 | 38.029 | 8.362 | −5.798 | 1.00 | 45.58 |
| ATOM | 2845 | O | ARG X | 10 | 38.755 | 9.338 | −5.571 | 1.00 | 49.67 |
| ATOM | 2846 | CB | ARG X | 10 | 38.911 | 7.542 | −8.015 | 1.00 | 46.09 |
| ATOM | 2847 | CG | ARG X | 10 | 39.575 | 6.367 | −8.745 | 1.00 | 51.91 |
| ATOM | 2848 | CD | ARG X | 10 | 41.077 | 6.227 | −8.402 | 1.00 | 51.06 |
| ATOM | 2849 | NE | ARG X | 10 | 41.331 | 6.132 | −6.963 | 1.00 | 53.68 |
| ATOM | 2850 | CZ | ARG X | 10 | 42.308 | 5.409 | −6.414 | 1.00 | 53.45 |
| ATOM | 2851 | NH1 | ARG X | 10 | 43.138 | 4.708 | −7.177 | 1.00 | 58.15 |
| ATOM | 2852 | NH2 | ARG X | 10 | 42.457 | 5.370 | −5.101 | 1.00 | 50.78 |
| ATOM | 2853 | N | TRP X | 11 | 36.796 | 8.246 | −5.330 | 1.00 | 40.63 |
| ATOM | 2854 | CA | TRP X | 11 | 36.128 | 9.267 | −4.527 | 1.00 | 36.28 |
| ATOM | 2855 | C | TRP X | 11 | 36.792 | 9.358 | −3.177 | 1.00 | 31.66 |
| ATOM | 2856 | O | TRP X | 11 | 36.729 | 10.375 | −2.486 | 1.00 | 30.50 |
| ATOM | 2857 | CB | TRP X | 11 | 34.685 | 8.834 | −4.337 | 1.00 | 37.56 |
| ATOM | 2858 | CG | TRP X | 11 | 33.818 | 9.633 | −3.432 | 1.00 | 38.34 |
| ATOM | 2859 | CD1 | TRP X | 11 | 32.991 | 10.652 | −3.804 | 1.00 | 39.63 |
| ATOM | 2860 | CD2 | TRP X | 11 | 33.467 | 9.310 | −2.083 | 1.00 | 41.41 |
| ATOM | 2861 | NE1 | TRP X | 11 | 32.132 | 10.967 | −2.787 | 1.00 | 40.82 |
| ATOM | 2862 | CE2 | TRP X | 11 | 32.395 | 10.157 | −1.715 | 1.00 | 43.60 |
| ATOM | 2863 | CE3 | TRP X | 11 | 33.937 | 8.376 | −1.152 | 1.00 | 45.51 |
| ATOM | 2864 | CZ2 | TRP X | 11 | 31.789 | 10.108 | −0.443 | 1.00 | 43.79 |
| ATOM | 2865 | CZ3 | TRP X | 1 | 33.333 | 8.325 | 0.121 | 1.00 | 48.58 |
| ATOM | 2866 | CH2 | TRP X | 11 | 32.267 | 9.187 | 0.455 | 1.00 | 46.05 |
| ATOM | 2867 | N | TYR X | 12 | 37.430 | 8.269 | −2.806 | 1.00 | 21.31 |
| ATOM | 2868 | CA | TYR X | 12 | 38.051 | 8.214 | −1.528 | 1.00 | 20.80 |
| ATOM | 2869 | C | TYR X | 12 | 39.346 | 8.991 | −1.501 | 1.00 | 25.81 |
| ATOM | 2870 | O | TYR X | 12 | 40.078 | 8.949 | −0.503 | 1.00 | 27.65 |
| ATOM | 2871 | CB | TYR X | 12 | 38.248 | 6.745 | −1.157 | 1.00 | 16.69 |
| ATOM | 2872 | CG | TYR X | 12 | 37.021 | 6.163 | −0.516 | 1.00 | 13.49 |
| ATOM | 2873 | CD1 | TYR X | 12 | 35.961 | 5.734 | −1.283 | 1.00 | 10.56 |
| ATOM | 2874 | CD2 | TYR X | 12 | 36.875 | 6.142 | 0.884 | 1.00 | 13.83 |
| ATOM | 2875 | CE1 | TYR X | 12 | 34.798 | 5.309 | −0.684 | 1.00 | 5.00 |
| ATOM | 2876 | CE2 | TYR X | 12 | 35.708 | 5.715 | 1.473 | 1.00 | 5.00 |
| ATOM | 2877 | CZ | TYR X | 12 | 34.697 | 5.310 | 0.677 | 1.00 | 5.00 |
| ATOM | 2878 | OH | TYR X | 12 | 33.558 | 4.858 | 1.222 | 1.00 | 12.55 |
| ATOM | 2879 | N | CYS X | 13 | 39.634 | 9.709 | −2.586 | 1.00 | 27.88 |
| ATOM | 2880 | CA | CYS X | 13 | 40.882 | 10.472 | −2.664 | 1.00 | 30.17 |
| ATOM | 2881 | C | CYS X | 13 | 40.713 | 11.899 | −2.249 | 1.00 | 28.63 |
| ATOM | 2882 | O | CYS X | 13 | 41.668 | 12.552 | −1.868 | 1.00 | 31.40 |
| ATOM | 2883 | CB | CYS X | 13 | 41.462 | 10.432 | −4.068 | 1.00 | 31.13 |
| ATOM | 2884 | SG | CYS X | 13 | 42.084 | 8.789 | −4.513 | 1.00 | 34.03 |
| ATOM | 2885 | N | GLN X | 14 | 39.489 | 12.385 | −2.324 | 1.00 | 30.33 |
| ATOM | 2886 | CA | GLN X | 14 | 39.231 | 13.750 | −1.925 | 1.00 | 31.72 |
| ATOM | 2887 | C | GLN X | 14 | 39.561 | 13.913 | −0.451 | 1.00 | 29.41 |
| ATOM | 2888 | O | GLN X | 14 | 39.728 | 15.023 | 0.027 | 1.00 | 36.99 |
| ATOM | 2889 | CB | GLN X | 14 | 37.763 | 14.111 | −2.136 | 1.00 | 33.64 |
| ATOM | 2890 | CG | GLN X | 14 | 36.909 | 13.815 | −0.916 | 1.00 | 42.04 |
| ATOM | 2891 | CD | GLN X | 14 | 35.438 | 14.004 | −1.167 | 1.00 | 45.95 |
| ATOM | 2892 | OE1 | GLN X | 14 | 34.880 | 15.083 | −0.944 | 1.00 | 50.57 |
| ATOM | 2893 | NE2 | GLN X | 14 | 34.791 | 12.951 | −1.629 | 1.00 | 50.89 |
| ATOM | 2894 | N | PHE X | 15 | 39.668 | 12.824 | 0.287 | 1.00 | 26.86 |
| ATOM | 2895 | CA | PHE X | 15 | 39.920 | 12.993 | 1.700 | 1.00 | 26.22 |
| ATOM | 2896 | C | PHE X | 15 | 41.334 | 12.740 | 2.087 | 1.00 | 33.70 |
| ATOM | 2897 | O | PHE X | 15 | 41.609 | 12.586 | 3.264 | 1.00 | 36.36 |
| ATOM | 2898 | CB | PHE X | 15 | 39.015 | 12.087 | 2.531 | 1.00 | 23.73 |
| ATOM | 2899 | CG | PHE X | 15 | 37.626 | 11.895 | 1.954 | 1.00 | 25.30 |
| ATOM | 2900 | CD1 | PHE X | 15 | 37.375 | 10.922 | 0.992 | 1.00 | 21.70 |
| ATOM | 2901 | CD2 | PHE X | 15 | 36.565 | 12.656 | 2.409 | 1.00 | 25.26 |
| ATOM | 2902 | CE1 | PHE X | 15 | 36.111 | 10.714 | 0.512 | 1.00 | 22.78 |

TABLE III-continued

| | | | | X | Y | Z | Q | B |
|---|---|---|---|---|---|---|---|---|
| ATOM | 2903 | CE2 | PHE X 15 | 35.282 | 12.447 | 1.919 | 1.00 | 25.86 |
| ATOM | 2904 | CZ | PHE X 15 | 35.060 | 11.476 | 0.977 | 1.00 | 23.75 |
| ATOM | 2905 | N | VAL X 16 | 42.249 | 12.726 | 1.124 | 1.00 | 43.63 |
| ATOM | 2906 | CA | VAL X 16 | 43.646 | 12.459 | 1.463 | 1.00 | 53.34 |
| ATOM | 2907 | C | VAL X 16 | 44.560 | 13.658 | 1.557 | 1.00 | 59.99 |
| ATOM | 2908 | O | VAL X 16 | 44.788 | 14.225 | 2.641 | 1.00 | 63.33 |
| ATOM | 2909 | CB | VAL X 16 | 44.311 | 11.535 | 0.465 | 1.00 | 51.57 |
| ATOM | 2910 | CG1 | VAL X 16 | 45.263 | 10.606 | 1.214 | 1.00 | 53.93 |
| ATOM | 2911 | CG2 | VAL X 16 | 43.263 | 10.792 | −0.338 | 1.00 | 55.02 |
| ATOM | 2912 | N | GLU X 17 | 45.120 | 13.999 | 0.400 | 1.00 | 65.70 |
| ATOM | 2913 | CA | GLU X 17 | 46.036 | 15.112 | 0.255 | 1.00 | 69.56 |
| ATOM | 2914 | C | GLU X 17 | 45.106 | 16.292 | 0.232 | 1.00 | 73.68 |
| ATOM | 2915 | O | GLU X 17 | 43.942 | 16.059 | −0.175 | 1.00 | 75.28 |
| ATOM | 2916 | CB | GLU X 17 | 46.778 | 14.996 | −1.073 | 1.00 | 68.63 |
| ATOM | 2917 | CG | GLU X 17 | 48.190 | 15.528 | −1.062 | 1.00 | 71.36 |
| ATOM | 2918 | CD | GLU X 17 | 48.743 | 15.744 | −2.472 | 1.00 | 73.73 |
| ATOM | 2919 | OE1 | GLU X 17 | 47.948 | 15.634 | −3.436 | 1.00 | 73.37 |
| ATOM | 2920 | OE2 | GLU X 17 | 49.964 | 16.021 | −2.618 | 1.00 | 71.80 |
| ATOM | 2921 | OXT | GLU X 17 | 45.522 | 17.402 | 0.634 | 1.00 | 80.00 |

What is claimed is:

1. A peptide comprising the following amino acid sequence:

$$X_i\text{-a-b-Cys-d-e-f-g-h-i-j-k-l-Cys-n-o-}X_k$$

wherein;
  a is an amino acid or is absent;
  b is Leu, Ile, Val, Ala, Arg, Gln, or Asn;
  d is an amino acid;
  e is an amino acid;
  f is Ala, Asp, Glu, Phe, Gly, His, Ile, Lys, Leu, Met, Asn, Pro, Gln, Arg, Ser, Thr, Val, Trp, or Tyr;
  g is an amino acid;
  h is Ala, Cys, Asp, Phe, Gly, His, Ile, Lys, Leu, Met, Asn, Pro, Gln, Arg, Thr, Val, Trp, or Tyr;
  i is Ala, Asp, Glu, Phe, Gly, His, Lys, Met, Asn, Pro, Gln, Ser, Thr, Val, Trp, or Tyr;
  j is Ala, Asp, Glu, Phe, Gly, Ile, Lys, Leu, Met, Asn, Gln, Arg, Ser, Thr, Val, Trp, or Tyr;
  k is Trp, Tyr, β-Napthylalanine, or Phe;
  l is Tyr, Phe, β-Napthylalanine, 4 methylphenylalanine, 3-(3,4-dihydroxyphenyl) alanine, meta-Tyr, or Trp;
  n is an amino acid; and
  o is Phe, Tyr, Trp, β-Napthylalanine, o-methyl Tyr, Norleucine, or meta-Tyr; and
  wherein the peptide binds FVIIa in an in vitro assay,
  wherein $X_i$ is absent or is a peptide between 1 and 100 amino acids; and $X_k$ is absent or a peptide between 1 and 100 amino acids.

2. The peptide of claim 1 having an $IC_{50}$ for FVIIa of less than 1 µM.

3. The peptide of claim 1 having an $IC_{50}$ for FVIIa of less than 1 nM.

4. The peptide of claim 1 which binds FVIIa and inhibits FVIIa activity.

5. The peptide of claim 4 which inhibits FVIIa activity selected from the group consisting of activation of FVII, activation of FIX and activation of FX.

6. The peptide of claim 5 having an $IC_{50}$ for FX activation of less than 10 µM.

7. The peptide of claim 6 having an $IC_{50}$ for FX activation of less than 100 nM.

8. The peptide of claim 7 having an $IC_{50}$ for FX activation of less than 5 nM.

9. The peptide of claim 1 which is a cyclic peptide.

10. The peptide of claim 1 wherein $X_i$ and $X_k$ are peptides of between 1 and 50 amino acids.

11. The peptide of claim 1 wherein $X_i$ and $X_k$ are peptides of between 1 and 10 amino acids.

12. The peptide of claim 1 wherein $X_i$ and $X_k$ are peptides of between 1 and 4 amino acids.

13. The peptide of claim 1 wherein;
  b is Leu, Ile, Val, or Ala;
  h is Ile, Val, Leu, or Ala;
  i is Asp, Glu, Ser, Thr, or Ala;
  k is Trp, or β-Napthylalanine;
  l is Tyr, or Phe;
  o is Phe, Tyr, o-methyl Tyr or meta-Tyr.

14. The peptide of claim 13 wherein
  h is Ile, Val, or Leu;
  i is Asp, Glu, or Ser;
  j is Arg, Lys, Gln, or Ala; and
  n is Gln, Met, Gly, Arg, Ser, Lys, Leu, Ala, Asn, or Thr.

15. The peptide of claim 14 wherein
  h is Ile, or Val;
  i is Asp;
  j is Arg;
  l is Tyr;
  n is Gln, or Met; and
  o is Phe, or o-methyl Tyrosine.

16. The peptide of claim 15 wherein:
  a is Asn, Arg, Phe, Gln, Gly, Pro, Thr, Ser, or Ala;
  f is Pro, Gly, or Ala.

17. The peptide of claim 1 wherein
  $X_i$ is a peptide of between 2 to 6 amino acids;
  a is Ala, Thr, or Ser;
  b is Leu;
  d is Asp, Glu, Ser, Ala, Arg, Thr, His, Met, Val, or Asn;
  e is Asn, Asp, Arg, Ala, or Glu;
  f is Pro;
  g is Arg, Ala, or Glu;
  h is Ile, Val, or Leu;
  i is Asp, Glu, or Ser;
  j is Arg, Lys, Gln, or Ala;
  n is Gln, Met, Gly, Arg, Ser, Lys, Leu, Ala, Asn, Tyr, or Thr; and
  $X_k$ is a peptide of between 2 and 6 amino acids.

18. The peptide of claim 17 having the following formula $X_i$-Ala-Leu-Cys-d-e-Pro-Arg-h-Asp-Arg-k-Tyr-Cys-n-Phe-$X_k$ (SEQ ID NO: 105) wherein
  $X_i$ is absent or is a peptide of between 1 to 4 amino acids;
  d is Asp, Glu, Ser, Ala, or Arg;
  e is Asn, Asp, Arg, or Ala;
  h is Ile, Leu, or Val;
  k is Trp, or β-Napthylalanine;
  n is Gln, Tyr, or Ala; and
  $X_k$ is a 3 amino acid peptide.

19. The peptide of claim 18 wherein the peptide is selected from the group consisting of:
  -ALCDDPRVDRWYCQFVEG—(SEQ ID NO:8)
  TF-74—VGALCDDPRVDRWYCQFVEG—(SEQ ID NO:6),
  TF151—ALCDNPRIDRWYCQFVEG—(SEQ ID NO:43),
  TF106—ALCDNPRVDRWYCQFVEG—(SEQ ID NO:18), and
  TF121—ALCDDPRIDRWYCQFVEG—(SEQ ID NO:30).

20. The peptide of claim 1 comprising the following amino acid sequence:

$$X_i\text{-a-b-Cys-d-Asp-Pro-Arg-h-Asp-Arg-Trp-Tyr-Cys-n-o-}X_k \text{ (SEQ ID NO: 106)}$$

wherein
  $X_i$ is absent or a peptide of between 1 and 4 amino acids;
  a is Ala, Asn, Arg, Phe, Gln, Gly, Thr, Ser, or Pro;
  b is Leu, Ala, Val, Ile, Arg, Gin, or Asn;
  d is an amino acid;
  h is Ile, Val, Leu, or Ala;
  n is an amino acid;

o is Phe, Tyr, Trp, meta-Tyr, or β-Napthylalanine; and $X_k$ is a peptide of between 1 and 4 amino acids.

21. The peptide of claim 20 having the following formula:

$X_i$-a-Leu-Cys-d-Asp-Pro-Arg-h-Asp-Arg-Trp-Tyr-Cys-n-o-$X_k$ (SEQ ID NO: 107)

wherein a is Ala, Thr, or Ser;

d is Asp, Glu, Ser, Ala, Arg, Thr, His, Met, Val, or Asn;

h is Ile, Val, or Leu;

n is Gln, Met, Gly, Arg, Ser, Lys, Ala, Asn, or Thr; and o is Phe, or Tyr.

22. The peptide of claim 20 wherein the peptide is selected from the group consisting of:
-ALCDDPRVDRWYCQFVEG—(SEQ ID NO:8)
TF-74—VGALCDDPRVDRWYCQFVEG—(SEQ ID NO:6),
TF121—ALCDDPRIDRWYCQFVEG—(SEQ ID NO:30), and
TF192—ALCDDPRVDRWYCQmYVEG—(SEQ ID NO: 114).

23. The peptide of claim 1 comprising the following amino acid sequence: $X_i$-Ala-Leu-Cys-d-e-Pro-Arg-h-i-j-k-Tyr-Cys-n-o-$X_k$ (SEQ ID NO: 108) wherein $X_i$ is absent or a peptide of between 1 and 4 amino acids;

d is Asp, Ala, or Arg;

e is Asp, Ala, Asn, or Arg;

h is Val, Ile, or Leu;

i is Asp, or Glu;

j is Lys, or Arg;

k is Trp, or β-Napthylalanine;

n is Gln, Tyr, or Ala;

o is Phe, meta-Tyr, or o-methyl Tyr; and $X_k$ is a 3 amino acid peptide.

24. A method of treating a disorder selected from the group consisting of deep venous thrombosis, arterial thrombosis, stroke, tumor metastasis, thrombolysis, arteriosclerosis, and restenosis following angioplasty in a host in need thereof comprising administering to the host a therapeutically effective amount of the peptide of claim 23.

25. A pharmaceutical composition comprising the peptide of claim 23 and a pharmaceutically acceptable carrier.

26. The peptide of claim 23 wherein the peptide is selected from the group consisting of:
-ALCDDPRVDRWYCQFVEG—(SEQ ID NO:8)
TF-74—VGALCDDPRVDRWYCQFVEG—(SEQ ID NO:6),
TF151—ALCDNPRIDRWYCQFVEG—(SEQ ID NO:43),
TF106—ALCDNPRVDRWYCQFVEG—(SEQ ID NO:18),
TF121—ALCDDPRIDRWYCQFVEG—(SEQ ID NO:30), and
TF192—ALCDDPRVDRWYCQmYVEG—(SEQ ID NO: 114).

27. The peptide of claim 26, wherein the peptide comprises ALCDDPRVDRWYCQmYVEG—(SEQ ID NO: 114).

28. The peptide of claim 26, wherein the peptide comprises—ALCDDPRVDRWYCQFVEG—(SEQ ID NO:8).

29. The peptide of claim 26, the peptide comprises VGALCDDPRVDRWYCQFVEG—(SEQ ID NO:6).

30. The peptide of claim 26, wherein the peptide comprises ALCDNPRIDRWYCQFVEG—(SEQ ID NO:43).

31. The peptide of claim 26, wherein the peptide comprises ALCDDPRIDRWYCQFVEG—(SEQ ID NO:30).

32. The peptide of claim 26, wherein the peptide comprises ALCDNPRVDRWYCQFVEG—(SEQ ID NO:18).

33. The peptide of claim 23, wherein a N terminal amino acid is modified, a C terminal amino acid is modified, or the N and C terminal amino acids are modified.

34. A method of inhibiting FVIIa activity comprising contacting FVIIa with the peptide of claim 1 in the presence of tissue factor and under conditions which allow binding of the peptide to FVIIa to occur.

35. The method of claim 34 wherein the peptide is a cyclic peptide.

36. The method of claim 35 wherein the peptide comprises the following amino acid sequence:

$X_i$-a-b-Cys-d-Asp-Pro-Arg-h-Asp-Arg-Trp-Tyr-Cys-n-o-$X_k$ (SEQ ID NO: 106), wherein $X_i$ is absent or a peptide of between 1 and 4 amino acids; wherein a is Ala, Asn, Arg, Phe, Gln, Gly, or Pro;

b is Leu, Ala, Val, Ile, Arg, Gln, or Asn;

d is an amino acid;

h is Ile, Val, Leu, or Ala;

n is an amino acid;

o is Phe, Tyr, Trp, or β-Napthylalanine;

$X_k$ is a peptide of between 1 and 4 amino acids.

37. The method of claim 35 wherein the peptide comprises the following amino acid sequence:

$X_i$-Ala-Leu-Cys-d-e-Pro-Arg-h-i-j-k-Tyr-Cys-n-o-$X_k$ (SEQ ID NO: 108), wherein $X_i$ is absent or a peptide of between 1 and 4 amino acids;

d is Asp, Ala, or Arg;

e is Ala, Asp, Asn, or Arg;

h is Ile, Val, Leu, or Ala;

i is Asp, or Glu;

j is Lys, or Arg;

k is Trp, Tyr, Phe, or β-Napthylalanine;

n is Gln, Tyr, or Ala;

o is Tyr, Phe, β-Napthylalanine, o-methyl Tyr, meta-Tyr, or Norleucine; and $X_k$ is a 3 amino acid peptide.

38. A method for selecting a compound which blocks FVII/FVIIa activation of FX comprising the steps of:
(1) contacting FVII/FVIIa with the peptide of claim 1 in the presence and absence of a candidate compound under conditions which allow specific binding of the peptide of claim 17 to FVII/FVIIa to occur;
(2) detecting the amount of specific binding of the peptide of claim 17 to FVII/FVIIa; and (3) identifying the candidate compound that inhibits the binding of the peptide of claim 17 to FVII/FVIIa, wherein the inhibition of binding of the peptide of claim 1 in the presence of the candidate compound relative to the binding in the absence of the candidate molecule is indicative of the ability of the candidate compound to block FVII/FVIIa activation of FX.

39. A method of treating a disorder selected from the group consisting of deep venous thrombosis, arterial thrombosis, stroke, tumor metastasis, thrombolysis, arteriosclerosis, and restenosis following angioplasty in a host in need thereof comprising administering to the host a therapeutically effective amount of the peptide of claim 1.

40. A pharmaceutical composition comprising the peptide of claim 1 and a pharmaceutically acceptable carrier.

41. The composition of claim 40 which is suitable for inhalation.

42. The composition of claim 41 which is dry powder.

43. The composition of claim 41 which is a liquid.

44. The composition of claim 41 which is a crystal.

45. The peptide of claim 1 which is a crystal.

46. The peptide of claim 1, wherein a N terminal amino acid is modified, a C terminal amino acid is modified, or the N and C terminal amino acids are modified.

47. A cyclic peptide comprising the following amino acid sequence:

Leu-Cys-d-e-Pro-g-h-i-j-Trp-Tyr-Cys-n-Phe wherein d is Glu, Asp or Ser;

e is Asn, Asp, Arg, Ala, or Glu;

g is Arg, Ala, or Glu;

h is Leu, Ile, or Val;

i is Asp, Glu, or Ser;

j is Arg, Lys, Gln, or Ala; and n is Gln, Tyr, or Ala, and wherein the peptide binds FVIIa in an in vitro assay.

48. The cyclic peptide of claim 47 wherein the peptide is selected from the group consisting of:

-ALCDDPRVDRWYCQFVEG—(SEQ ID NO:8)

TF-74—VGALCDDPRVDRWYCQFVEG—(SEQ ID NO:6),

TF115—ALCDNPRIDRWYCQFVEG—(SEQ ID NO:43),

TF106—ALCDNPRVDRWYCQFVEG—(SEQ ID NO:18), and

TF121—ALCDDPRIDRWYCQFVEG—(SEQ ID NO:30).

49. A method of inhibiting FVIIa activity comprising contacting FVIIa with the peptide of claim 47 in the presence of tissue factor and under conditions which allow binding of the peptide to FVIIa to occur.

50. A method for selecting a compound which blocks FVII/FVIIa activation of FX comprising the steps of:

(1) contacting FVII/FVIIa with the peptide of claim 47 in the presence and absence of a candidate compound under conditions which allow specific binding of the peptide of claim 47 to FVII/FVIIa to occur;

(2) detecting the amount of specific binding of the peptide of claim 45 to FVII/FVIIa; and (3) identifying the candidate compound that inhibits the binding of the peptide of claim 45 to FVII/FVIIa, wherein the inhibition of binding in the presence of the candidate compound relative to the binding in the absence of the candidate compound is indicative of the ability of the candidate compound to block FVII/FVIIa activation of FX.

51. A method of treating a disorder selected from the group consisting of deep venous thrombosis, arterial thrombosis, stroke, tumor metastasis, thrombolysis, arteriosclerosis, and restenosis following angioplasty in a host in need thereof comprising administering to the host a therapeutically effective amount of the peptide of claim 47.

52. A pharmaceutical composition comprising the peptide of claim 47 and a pharmaceutically acceptable carrier.

53. The composition of claim 52 which is suitable for inhalation.

54. The composition of claim 52 which is dry powder.

55. The composition of claim 52 which is a liquid.

56. The composition of claim 52 which is a crystal.

57. The peptide of claim 47 which is a crystal.

58. The peptide of claim 47, wherein the peptide comprises—ALCDDPRVDRWYCQFVEG—(SEQ ID NO:8).

59. The peptide of claim 47, wherein the peptide comprises VGALCDDPRVDRWYCQFVEG—(SEQ ID NO:6).

60. The peptide of claim 47, wherein the peptide comprises ALCDNPRIDRWYCQFVEG—(SEQ ID NO:43).

61. The peptide of claim 47, wherein the peptide comprises ALCDDPRIDRWYCQFVEG—(SEQ ID NO:30).

62. The peptide of claim 47, wherein the peptide comprises ALCDNPRVDRWYCQFVEG—(SEQ ID NO:18).

63. The peptide of claim 47, wherein a N terminal amino acid is modified, a C terminal amino acid is modified, or the N and C terminal amino acids are modified.

* * * * *

UNITED STATES PATENT AND TRADEMARK OFFICE
CERTIFICATE OF CORRECTION

PATENT NO.         : 7,084,109 B2
APPLICATION NO. : 10/202915
DATED                  : August 1, 2006
INVENTOR(S)       : Dennis et al.

It is certified that error appears in the above-identified patent and that said Letters Patent is hereby corrected as shown below:

Title Page, (56) References Cited, Davie reference, "Maitenance" should be --Maintenance--

Col. 5, line 22: "CH.sub.3CO" should read --$CH_3CO$--

Col. 5, line 22: "NH.sub.2" should read --$NH_2$--.

Col. 5, line 23: "NH.sub.2" should read --$NH_2$--.

Col. 5, line 24: ".beta.-napthylalanine" should read --β-napthylalanine--.

Col. 5, line 26: ".epsilon.-amino" should read --ϵ-amino--.

Col. 5, line 28: ".gamma.-curboxyglutamic" should read --γ-carboxyglutamic--.

Col. 5, line 31: "alan– ine" should read --alanine--.

Col. 26, line 32: "examiple" should read --example--.

Col. 26, line 33: "acedemic" should read --academic--.

Col. 26, line 36: "incorported" should read --incorporated--.

Col 26, line 48: "substituion" should read --substitution--.

Col. 31, line 67: "hydochlorofluorocarbon" should read --hydrochlorofluorocarbon--.

Col. 101, claim 29, line 66: "26, the" should read --26, wherein the--.

UNITED STATES PATENT AND TRADEMARK OFFICE
CERTIFICATE OF CORRECTION

PATENT NO. : 7,084,109 B2
APPLICATION NO. : 10/202915
DATED : August 1, 2006
INVENTOR(S) : Dennis et al.

It is certified that error appears in the above-identified patent and that said Letters Patent is hereby corrected as shown below:

Col. 104, claim 50, line 6: "claim 45" should read --claim 47--.

Col. 104, claim 50, line 8: "claim 45" should read --claim 47--.

Signed and Sealed this

Twenty-eighth Day of November, 2006

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 7,084,109 B2 |
| APPLICATION NO. | : 10/202915 |
| DATED | : August 1, 2006 |
| INVENTOR(S) | : Dennis et al. |

It is certified that error appears in the above-identified patent and that said Letters Patent is hereby corrected as shown below:

Title Page, Item (56) References Cited, Davie reference, "Maitenance" should be --Maintenance--.

Col. 5, line 22: "CH.sub.3CO" should read --$CH_3CO$--.

Col. 5, line 22: "NH.sub.2" should read --$NH_2$--.

Col. 5, line 23: "NH.sub.2" should read --$NH_2$--.

Col. 5, line 24: ".beta.-napthylalanine" should read --β-napthylalanine--.

Col. 5, line 26: ".epsilon.-amino" should read --ε-amino--.

Col. 5, line 28: ".gamma.-curboxyglutamic" should read --γ-carboxyglutamic--.

Col. 5, line 31: "alan- ine" should read --alanine--.

Col. 26, line 32: "examiple" should read --example--.

Col. 26, line 33: "acedemic" should read --academic--.

Col. 26, line 36: "incorported" should read --incorporated--.

Col. 26, line 48: "substituion" should read --substitution--.

Col. 31, line 67: "hydochlorofluorocarbon" should read --hydrochlorofluorocarbon--.

Col. 101, claim 29, line 66: "26, the" should read --26, wherein the--.

UNITED STATES PATENT AND TRADEMARK OFFICE
CERTIFICATE OF CORRECTION

PATENT NO. : 7,084,109 B2
APPLICATION NO. : 10/202915
DATED : August 1, 2006
INVENTOR(S) : Dennis et al.

It is certified that error appears in the above-identified patent and that said Letters Patent is hereby corrected as shown below:

Col. 104, claim 50, line 6: "claim 45" should read --claim 47--.

Col. 104, claim 50, line 8: "claim 45" should read --claim 47--.

Signed and Sealed this

Fifth Day of February, 2008

JON W. DUDAS
*Director of the United States Patent and Trademark Office*